US006482179B1

United States Patent
Chu et al.

(10) Patent No.: US 6,482,179 B1
(45) Date of Patent: Nov. 19, 2002

(54) APPARATUSES, METHODS AND COMPOSITIONS FOR CLOSING TISSUE PUNCTURE OPENINGS

(75) Inventors: George H. Chu, Cupertino, CA (US); Jeffrey E. Yeung, San Jose, CA (US); Frank A. DeLustro, Belmont, CA (US)

(73) Assignee: Cohesion Technologies, Inc., Palo Alto, CA (US)

(*) Notice: Subject to any disclaimer, the term of this patent is extended or adjusted under 35 U.S.C. 154(b) by 0 days.

(21) Appl. No.: 09/578,814

(22) Filed: May 24, 2000

Related U.S. Application Data

(60) Provisional application No. 60/136,546, filed on May 28, 1999.

(51) Int. Cl.[7] ............................................. A61M 5/178
(52) U.S. Cl. .................................. 604/164.09; 606/214
(58) Field of Search ........................ 604/164.09, 101; 606/114, 213, 214, 144

(56) References Cited

U.S. PATENT DOCUMENTS

| | | | |
|---|---|---|---|
| 4,295,464 A | | 10/1981 | Shihata |
| 4,445,892 A | * | 5/1984 | Hussein et al. ............. 604/101 |
| 4,469,100 A | | 9/1984 | Hardwick |
| 4,627,837 A | | 12/1986 | Gonzalo |
| 4,781,677 A | | 11/1988 | Wilcox |
| 4,911,163 A | | 3/1990 | Fina |
| 4,930,496 A | | 6/1990 | Bosley, Jr. |
| 5,024,617 A | | 6/1991 | Karpiel |
| 5,334,216 A | | 8/1994 | Vidal et al. |
| 5,370,660 A | | 12/1994 | Weinstein et al. |
| 5,383,849 A | | 1/1995 | Johlin, Jr. |
| 5,441,517 A | | 8/1995 | Kensey et al. |
| 5,643,199 A | | 7/1997 | Rowland et al. |
| 5,728,132 A | | 3/1998 | Van Tassel et al. |
| 5,989,266 A | | 11/1999 | Foster |
| 6,033,427 A | * | 3/2000 | Lee ........................... 606/213 |
| 6,045,570 A | * | 4/2000 | Epstein et al. .............. 606/214 |
| 6,053,934 A | | 4/2000 | Andrews et al. |
| 6,071,300 A | * | 6/2000 | Brenneman et al. ........ 606/213 |
| 6,090,130 A | * | 7/2000 | Nash et al. .................. 606/213 |
| 6,126,675 A | * | 10/2000 | Shchervinsky et al. ..... 606/213 |
| 6,245,079 B1 | * | 6/2001 | Nobles et al. ............... 606/114 |

FOREIGN PATENT DOCUMENTS

| | | |
|---|---|---|
| DE | 1069823 | 11/1959 |
| EP | 0139091 | 5/1985 |
| EP | 0200668 | 11/1986 |
| FR | 2380018 | 9/1978 |
| WO | 9741782 | 11/1997 |
| WO | WO 98/19605 | 5/1998 |
| WO | 9825656 | 6/1998 |

OTHER PUBLICATIONS

J.P. Williams; A Double–Balloon Ureteric–Stone Extrator; The Lancet, Oct. 4, 1969; p. 725.

Quantum TTC® Biliary Balloon Dialtors; Wilson–Cook Medical, Inc., Winston–Salem, NC; Catalog (date unknown).

Tri–ex™ Triple Lumen Extraction Balloon; Wilson–Cook Medical, Inc., Winston–Salem, NC; Catalog (1996).

The WEB™ Extraction Basket; Wilson–Cook Medical, Inc., Winston–Salem, NC; Catalog (date unknown).

* cited by examiner

*Primary Examiner*—Teresa Walberg
*Assistant Examiner*—L Fastovsky
(74) *Attorney, Agent, or Firm*—Reed & Associates; Dianne E. Reed; Louis L. Wu

(57) ABSTRACT

Medical devices, and more particularly, devices, methods and compositions for sealing tissue puncture openings of patients after surgical operations are provided. A puncture wound sealing apparatus includes a positioning device having a depth sensing mechanism capable of providing feedback to an operator for the precise placement of an implant that is preferably resorbable and swellable after implantation. Such an implant provides for efficient sealing of the tissue puncture opening thus avoiding complications after surgical procedures in which blood vessels are punctured.

56 Claims, 34 Drawing Sheets

APPARATUSES, METHODS AND COMPOSITIONS FOR CLOSING TISSUE PUNCTURE OPENINGS

This application claims the benefit of Provisional application Ser. No. 60/136,546, filed May 28, 1999.

FIELD OF THE INVENTION

The present invention generally relates to medical devices and tissue engineering compositions, and more particularly, to devices, methods and compositions for sealing tissue puncture openings of patients after surgical operations.

BACKGROUND OF THE INVENTION

Certain medical procedures require the invasion of a patient's artery by creating a puncture opening in a patient's skin and subcutaneous tissue. For example, in a percutaneous transluminal coronary angioplasty (PTCA), it is common practice to insert an introducer catheter into the patient's artery through the surface of the skin and the underlying tissue. Thereafter, a balloon catheter or other type of catheter is inserted into the artery to perform various medical tasks. After the procedure, bleeding through the puncture opening is unavoidable and must be stopped. Very often, continuous bleeding is prevented by applying digital pressure on the puncture site for a prolong duration until hemostasis occurs. This practice is riddled with various problems. To begin with, the pressure normally has to be applied in excess of 30 minutes under the intense care of a medical practitioner. Furthermore, the hemostasis closure thus formed is quite often unreliable and susceptible to rupture causing undesirable consequences. In addition, pressuring the artery yields the effect of thrombosis, which restricts the blood flow to a patient during the post surgical period and consequently may cause unwanted complications.

Devices that are useful for replacing the manual pressuring method described above have previously been described. For example, U.S. Pat. No. 4,744,364 to Kensey, entitled "Device for Sealing Percutaneous Puncture in a Vessel," which issued on May 17, 1988, describes a protocol that includes first deploying a flat and flexible sealing member into the patient's blood vessel. The sealing member is attached to a drawstring. At the end of the sealing procedure, the drawstring is tightened resulting in the flexible sealing member collapsing on the inner wall of the blood vessel at the puncture site. The sealing member and the drawstring are secured in place on the patient's skin surface with an adhesive tape.

There are several drawbacks associated with Kensey's approach. First, since the device is deployed inside the blood vessel, fragmentation or disintegration of the sealing member may result in foreign objects introduced into the patient's blood stream. As a consequence, embolism may develop in the patient's blood system. Furthermore, the sealing member and the puncture opening have to be in good alignment to be effective. Misalignment can leak blood into the patient's subcutaneous tissue leading to hematoma as a repercussion.

To avoid the aforementioned shortfalls, there have been suggestions to deploy swellable, resorbable materials in the subcutaneous tissue at the puncture sites outside the vessels for sealing the puncture wounds. For example, U.S. Pat. No. 5,437,631, to Jenzen, entitled "Percutaneous Introducer Set and Method for Sealing Puncture Wounds," which issued on Aug. 1, 1995, describes a device that is used to deliver a swellable, resorbable material to the puncture site atop the blood vessel to seal the puncture wound. To practice this method, a secondary dilator first has to be inserted into the original puncture wound for additional puncture opening enlargement. Second, the secondary dilator has to be attached with a blunt nose coated with a contrast medium. In addition, the contrast medium must be administered to the blood stream, so that during operation, the position of the blunt nose in respect to the blood vessel is visible under fluoroscopy. The reason for the elaborated steps involved as taught by Jenzen is because the implant material has to be delivered to the puncture site precisely atop the vessel puncture opening. Delivery of the implant material other than the intended location can result in any of the complications mentioned above in association with Kensey's device.

U.S. Pat. No. 5,571,181 to Li, entitled "Soft Tissue Closure Systems," which issued Nov. 5, 1996, discloses a device that needs no additional enlargement of the original puncture opening. The use of Li's device also does not require the introduction of a contrast medium in conjunction with the various fluoroscopy steps. However, the teaching of Li still does not provide a good way of ensuring that the implant material is delivered precisely to the desired targeted location. That is, to avoid the various consequential effects such as hematoma and embolism, the implant material has to be precisely seated atop the puncture opening of the blood vessel at the puncture site. Instead, Li teaches the delivery of the implant material midway in the tissue at a distance above the blood vessel puncture opening. The remainder of the void is sealed by the patient's own blood clot. Thus, the practice of Li's method may result in hematoma. This is especially true when the blood in the remainder of the void does not clot fast enough, because it is blocked off from any external exposure by the swollen implant material and further by the subsequent application of the sealing tape.

U.S. Pat. No. 5,868,778 to Gershony et al., entitled "Vascular Sealing Apparatus and Method," which issued on Feb. 9, 1999, is a method in which an attempt is made to seal the puncture site precisely above the blood vessel. The method of Gershony et al. involves the deployment of a deflated balloon housed in a reaccess sheath into the blood vessel through an introducer sheath. After deployment, the balloon is inflated and pulled proximally. The inflated balloon acts as a temporary hemostatic seal blocking the puncture opening of the blood vessel during normal operation. Then, liquid procoagulant is injected into the introducer sheath. While the procoagulant is in the process of coagulating, the balloon is deflated and then pulled out along with the reaccess sheath. The timing of pulling out the balloon in practicing Gershony et al.'s method is critical and is difficult to control. Pulling out the balloon and the reaccess sheath too soon may end up with the liquid procoagulant dripping into the patient's blood stream and consequently increasing the possibility of embolism. Pulling out the balloon and the reaccess sheath too late after the procoagulant substantially coagulates may leave a trail of void after withdrawal, which directly leads to the patient's blood stream and renders the sealing method ineffective.

The success of the aforementioned procedures also depends on the hemostatic efficiency of the biomaterials used to seal the puncture site. Various biomaterials such as collagen and synthetic polymers with hemostatic properties have previously been described and can be adapted for use in the present application. See, e.g., U.S. Pat. Nos. 3,742, 955; 4,066,083; 4,891,359; 4,412,947; 4,578,067; 4,515, 637; 4,271,070; 4,891,359; 4,016,877; 5,162,430; 5,324, 775; and 5,874,500. Expandable implant materials have also been described that are capable of rehydration after insertion, which causes the implant to swell and become affixed in place. See, e.g., U.S. Pat. Nos. 5,326,350; 5,571, 181; and PCT WO 98/30141.

In the practice of sealing puncture openings after surgical operations, complications associated with hematoma and embolism are real concerns. In a survey review publication edited by Lansky, et al., entitled "TCT X Factoids: A Comprehensive Review of the Interventional Cardiovascular Literature," page 344 (1997–1998), it is stated that the proportion of operations using existing puncture wound closure devices resulting in any complications is 16.8%, in comparison with relying on the conventional method of digital pressure as mentioned above with a corresponding number of only 10.9%. The proportions are even more skewed with respect to major complications, which is 4.0% when devices are relied on as compared to 2.5% when manual compression is used. Phrased differently, the use of existent closure devices in performing puncture wound closure may shorten the healing time but increase the danger of inflicting various serious complications on the patient. Accordingly, there has been a long felt need to provide puncture opening closure devices that shorten recovery time, minimize unwanted complications after operations, and are easy to use.

SUMMARY OF THE INVENTION

It is accordingly an object of the invention to provide a tissue puncture opening closure device and method that minimize post-surgical complications.

It is another object of the invention to provide a tissue puncture opening closure device and method that are simple to use and easy to operate without unnecessary intermediate steps.

It is yet another object of the invention to provide a tissue puncture opening closure device and method that are inexpensive to manufacture and operate.

It is still another object of the invention to provide compositions for use in sealing tissues puncture openings and methods for using such compositions.

The present invention accomplishes the foregoing objectives by providing the puncture wound sealing apparatus that includes a positioning device having a depth sensing mechanism capable of providing feedback to an operator for the precise placement of an implant. After a percutaneous transluminal coronary angioplasty (PTCA), for example, the introducer sheath remains inserted in the patient's artery. The operator retains the introducer sheath at the puncture wound site and accurately positions the sheath relative to the artery based on the feedback provided by the depth sensing mechanism as a prelude for precise implant placement. Via a novel approach relying on the natural elasticity of the patient's blood vessel, the feedback can be in the form of fluid monitoring between the gap space formed between the positioning device and the bore of the introducer sheath. Alternatively, the distal end of the positioning device can be made extendable and the feedback can be in the form of resistance force experienced by the operator when the extended distal end encounters obstacles. Once the introducer sheath is accurately positioned, an implant made of swellable, resorbable material is precisely delivered to the patient via the sheath sealing the puncture wound, thereby substantially minimizing occurrences of consequential complications such as embolism and hematoma.

The present invention also concerns an implant adapted for sealing a tissue puncture opening outside a blood vessel of a living being, wherein the implant is made from a dried, swellable, resorbable matrix of, e.g., polyethylene glycol and gelatin in a weight ratio of between 1:3 and 3:1. Such implants provide for enhanced expansion properties and are well adapted for the procedures described herein.

In addition, the present invention concerns methods for sealing puncture openings outside a blood vessel using biomaterials that are adapted for formation of an implant capable of sealing such a tissue puncture opening. These materials need not be predried before implantation, but can be applied in liquid or gel form (or a combination of a liquid/gel and dry material(s)) at the tissue puncture opening and thereafter form a matrix that is strong enough to seal the opening.

In yet another embodiment, the present invention provides a method of sealing a tissue puncture opening in a living being that extends from an external puncture opening in a skin surface percutaneously through the tissue to a depth X, comprising the steps of inserting an elongated implant having a length greater than X into said tissue puncture opening, wherein the implant comprises a dried, swellable, resorbable matrix, and removing that portion of the implant that extends outside the external puncture opening. Such a method can be used to seal any tissue puncture opening created surgically or otherwise.

These and other features and advantages of the invention will be apparent to those skilled in the art from the following detailed description, taken together with the accompanying drawings, in which like reference numerals refer to like parts.

DETAILED DESCRIPTION OF THE INVENTION

Figure 1:
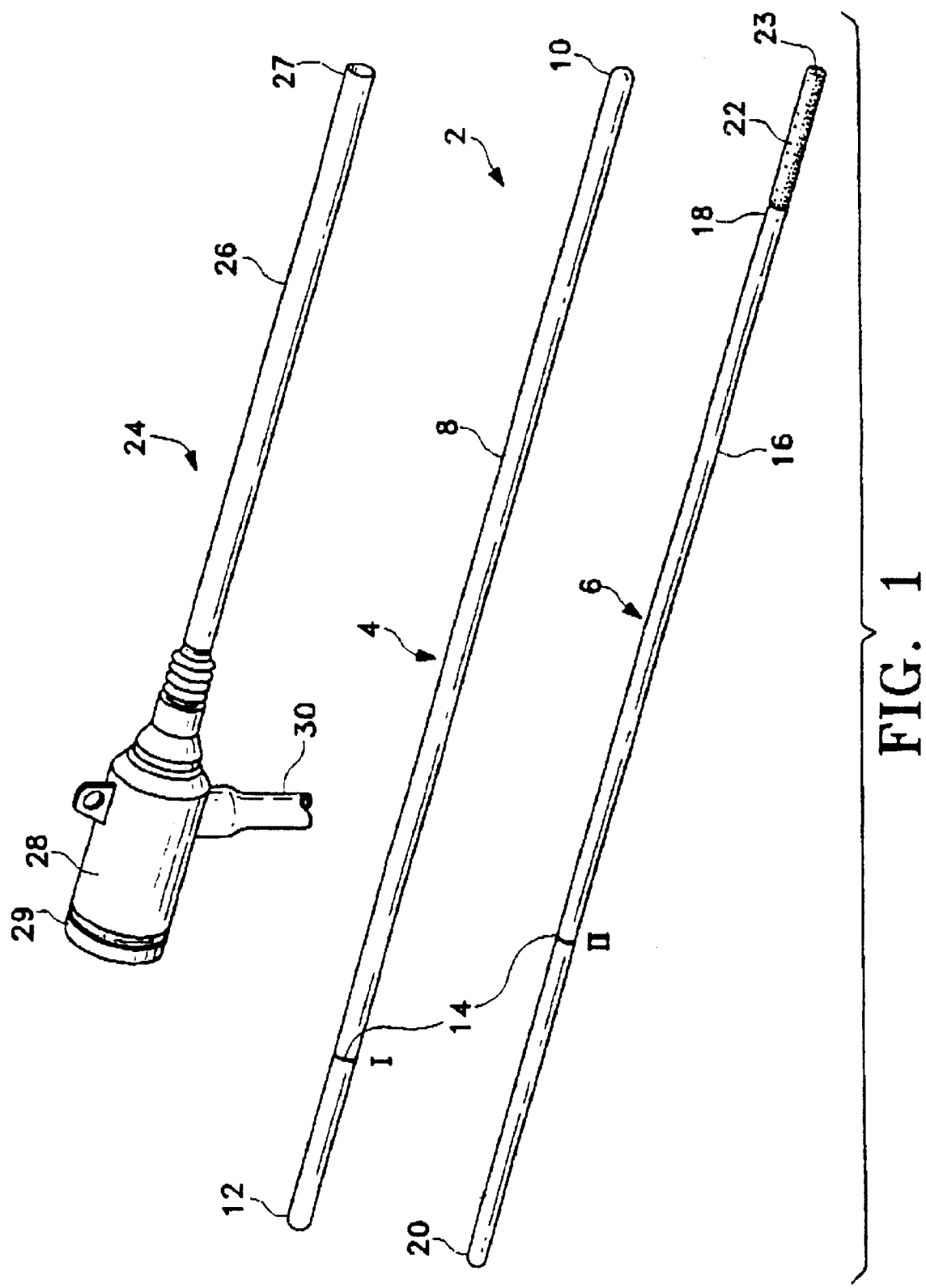
FIG. 1 is a perspective view of a first embodiment of the invention showing the various components.

As described herein, the present invention concerns apparatuses and methods for delivering an implant to a tissue puncture opening.

Definitions

The following definitions are provided to further describe various aspects of the preferred embodiments of the present invention.

The term "gel" refers to the state of matter between liquid and solid. As such, a "gel" has some of the properties of a liquid (i.e., the shape is resilient and deformable) and some of the properties of a solid (i.e., the shape is discrete enough to maintain three dimensions on a two dimensional surface.) Accordingly, "gelation time", also referred to herein as "gel time", refers to the time it takes for a composition to become non-flowable under modest stress. This is generally exhibited as achieving a gel strength, G', of greater than or equal to $10^2$ dynes/cm$^2$ in less than 1 minute.

The term "cohesive strength" refers to the ability of the compositions of the present invention to remain intact, i.e. not rupture, tear or crack, when subjected to physical stresses or environmental conditions. Cohesive strength is sometimes measured as a function of "burst strength".

The term "adhesive strength" refers to the ability of the compositions of the present invention to be able to remain attached to the tissues at the site of administration when subjected to physical stresses or environmental conditions.

The term "polymer" refers to a molecule consisting of individual chemical moieties, which may be the same or different, but are preferably the same, that are joined together. As used herein, the term "polymer" refers to individual chemical moieties that are joined end-to-end to form a linear molecule, as well as individual chemical moieties joined together in the form of a branched (e.g., a "multi-arm" or "star-shaped") structure.

The term "biocompatible" refers to the ability of the compositions of the present invention to be applied to tissues without eliciting significant inflammation and fibrosis or other adverse tissue responses.

The term "synthetic polymer" refers to polymers that are not naturally occurring and that are produced by chemical or recombinant synthesis. As such, naturally occurring proteins such as collagen and naturally occurring polysaccharides such as hyaluronic acid are specifically excluded. Proteins such as synthetic collagen, and carbohydrates such as synthetic hyaluronic acid, and their derivatives, are included.

The term "activated synthetic polymers" refers to synthetic polymers that have or have been chemically modified to have at least one functional group (e.g., a sulfhydryl group) that is capable of reacting with a corresponding reaction partner (e.g., a sulfhydryl-reactive group) to form a covalent bond. The term "multifunctionally activated" refers to synthetic polymers having two or more nucleophilic or electrophilic groups. Types of multifuctionally activated synthetic polymers include di-functionally activated, tri-functionally activated, tetra-functionally activated, and star-shaped activated polymers (that have four or more functional groups).

Implant Delivery Device Design and Use

Reference is now directed to FIG. 1 that shows a first embodiment of the invention generally designated by the reference numeral 2. The puncture wound closure device of this embodiment includes a positioning device 4 and an implant delivery device 6.

In this embodiment, the positioning device 4 is a position guide 8 that is a solid piece of elongated rod, which is part of a depth sensing mechanism that is more fully described below. The position guide 8 includes a distal end 10 and a proximal end 12, which are preferably rounded off so as to facilitate entry and minimize chances of injuries to a patient when the guide 8 is in use. Near the proximal end 12 is a marking 14, such as "I," as shown in FIG. 1. The marking 14 serves a purpose that will be more fully described below.

The implant delivery device 6 in this embodiment is another solid piece of elongated rod signified by the reference numeral 16. As with the position guide 8, the implant delivery rod 16 also has a distal end 18 and a proximal end 20 that are rounded off. Near the proximal end 20 there is also a marking 14. The distal end 18 of the delivery rod 16 is adapted to attach an implant 22. The method of a attachment can be gluing, clamping or crimping, for example. In this embodiment, the implant 22 is glued onto the distal end 18 of the delivery rod 16.

Shown in FIG. 1 is also an introducer 24, which comprises an introducer sheath 26 abuttingly attached to an introducer body 28. Affixed to the introducer body 28 is a sideport outlet 30. The introducer 24 has a distal end 27 at the introducer sheath 26 and a proximal end 29 at the introducer body 28. The introducer 24 is a common medical device and is frequently used with other medical procedures. For example, in a percutaneous coronary transluminal angioplasty (PCTA), the introducer 24 is first inserted into a patient's artery through the patient's surface skin and the subcutaneous tissue. A catheter carrying a balloon (not shown) is then inserted through the introducer sheath 26. The balloon (not shown) then travels through the artery and is inflated at the predetermined location for the purpose of compressing the plaques with the intended result of widening the artery caliber, for instance. After the operation, with most prior art puncture wound sealing devices, the introducer 24 is removed and the sealing process commences with the introduction of other instruments. However, in accordance with the present invention, the introducer 24 remains in its original place and the puncture sealing process starts with the continued use of the introducer 24. As such, considerable intermediate steps are eliminated.

Figure 2:
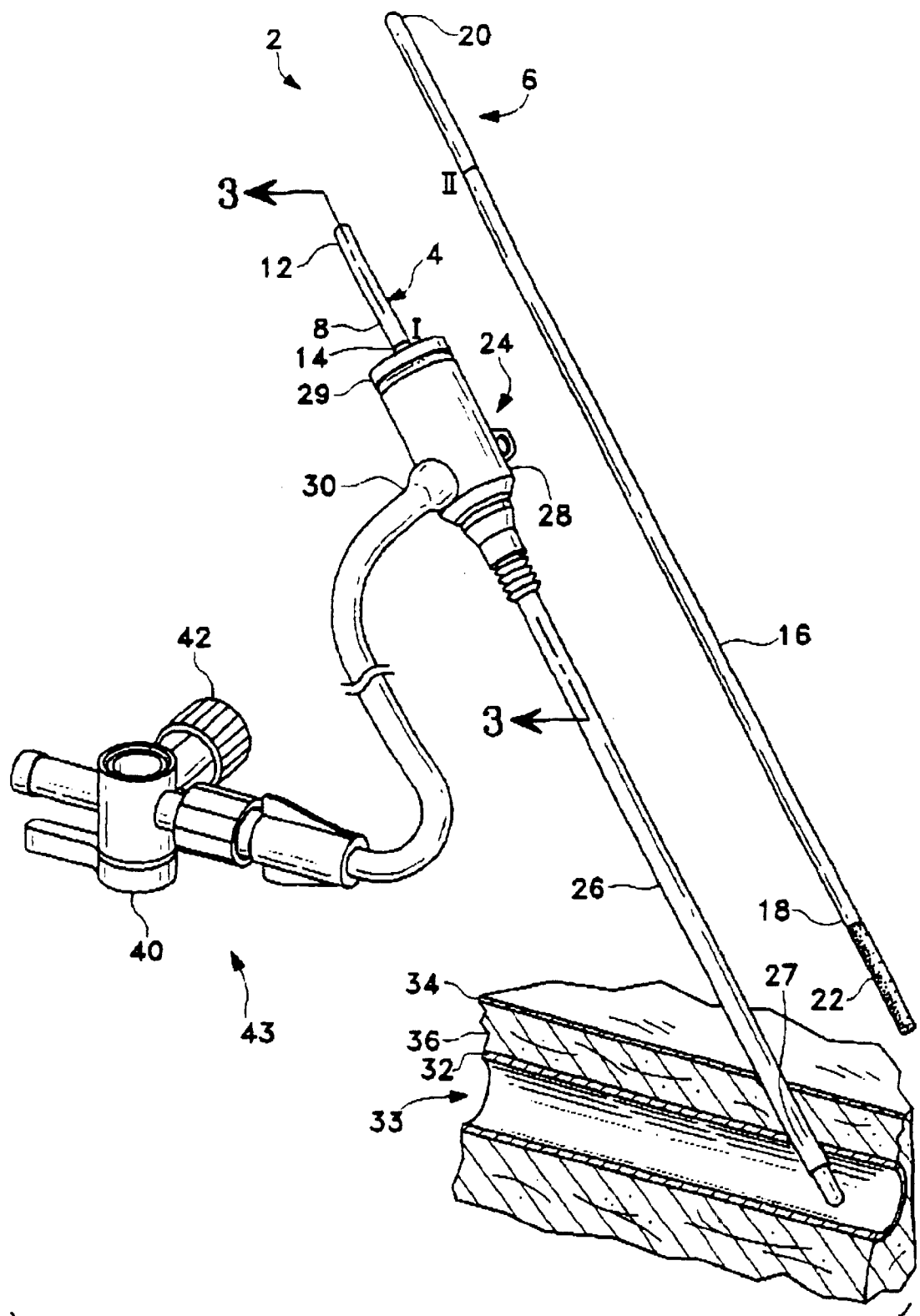
FIG. 2 is a perspective view of the first embodiment of the invention shown in applied.

FIG. 2 is a perspective view, which shows the arrangement of the different components of the first embodiment 2 with respect to the introducer 24. In FIG. 2, the introducer sheath 26 is illustrated as inserted into an artery 33 through the surface skin 34, the underlying tissue 36 and the artery wall 32. Placed inside the introducer sheath 26 is the positioning device 4, which is the position guide 8 in this case.

Figure 3:
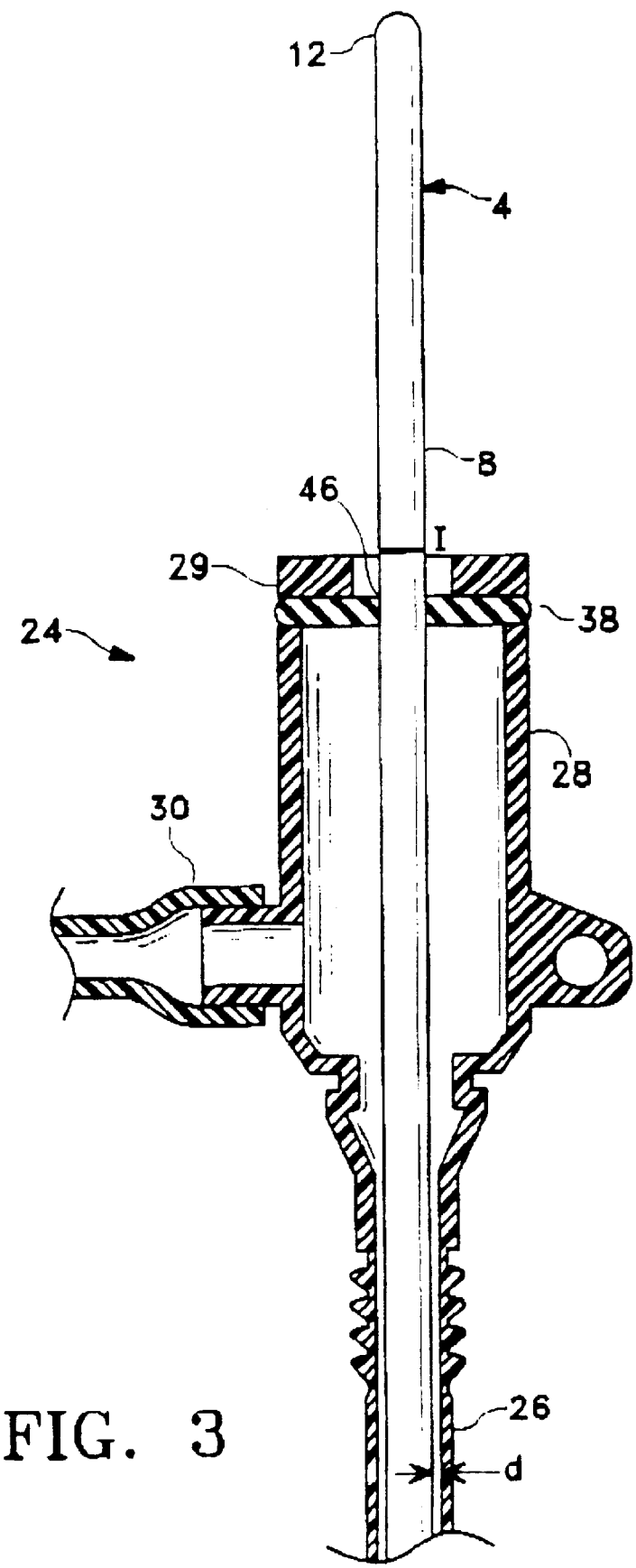
FIG. 3 is a cross-sectional view taken alone the line 3—3 of FIG. 2.

FIG. 3 is a cross-sectional view taken along the line 3—3 of FIG. 2, which shows the internal construction of the introducer body 28. At the proximal end of the introducer body 28 is a septum 38 having an orifice 46. The position guide 8 is shown inserted into the introducer 24 through the orifice 46 of the septum 38.

In accordance with the invention, the positioning device 4 and the introducer sheath 26 maintain a predetermined separation. Specifically, in this embodiment, the outermost surface of the position guide 8 and the inner wall of the introducer sheath 26 is spaced by a distance, d, as shown in FIG. 3. The value of d can range from 0.05 mm to 0.5 mm. In this embodiment, the dimension of the separation d is 0.2 mm.

Reference is now returned to FIG. 2. Attached to the side port outlet 30 of the introducer body 28 is a valve 40. The valve 40 is controlled by a turn knob 42. The valve 40 and the control knob 42 constitute part of a fluid monitoring section 43.

FIG. 2 also shows the implant delivery device 6, which is the delivery rod 16 in this embodiment. The implant 22 is also illustrated as attached to the distal end 18 of the delivery rod 16.

FIGS. 4A–4H illustrate the process of using the first embodiment in accordance with the invention. Reference is now made to FIGS. 4A–4H in conjunction with FIGS. 1–3. As mentioned before, after certain medical procedures, such as a PCTA, the introducer sheath 26 remains seated in the patient's artery 33 through the surface skin 34, the subcutaneous tissue 36 and the artery wall 32. With most prior art puncture wound sealing devices, the introducer sheath 26 is removed and other instruments are introduced to perform the sealing procedure. The present invention utilizes the introducer 26 and thus simplifies the sealing process and further curtails unnecessary bleeding.

Figure 4A:
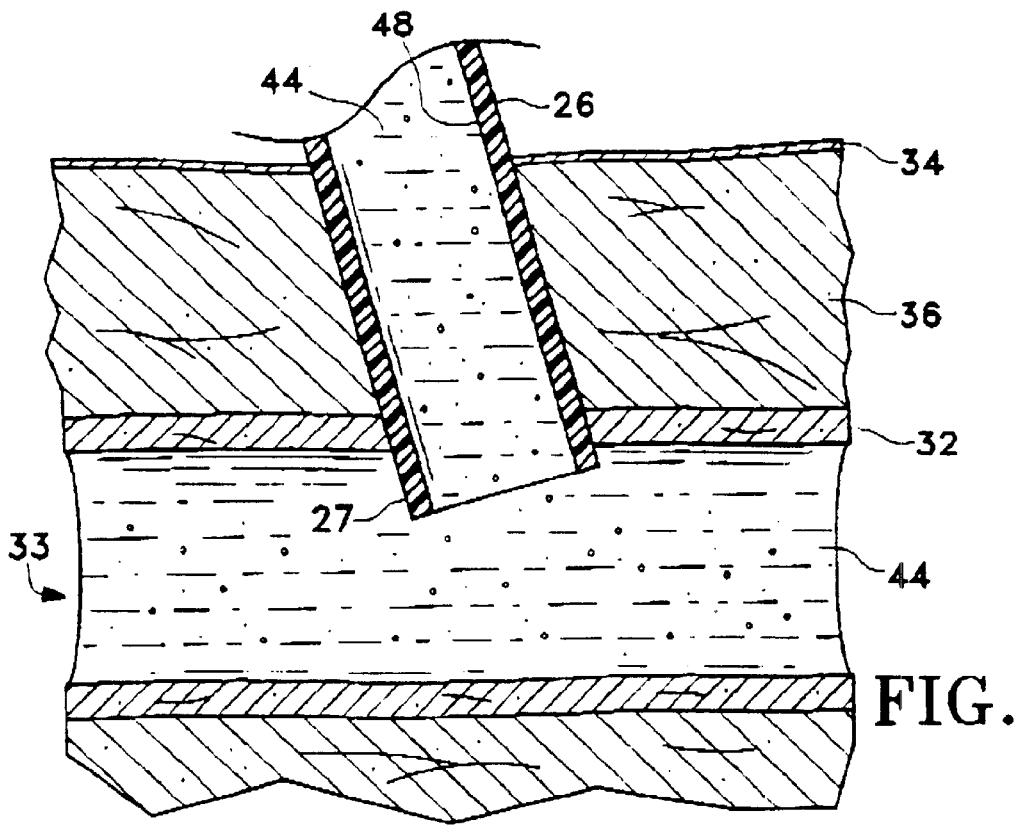
FIGS. 4A–4H are sequential views, shown in cross-section, the method of using the first embodiment of the invention.

As shown in FIG. 4A, the inside of the introducer sheath 26 is filled with blood 44. However, the blood 44 has no outlet in this instance because the orifice 46 of the septum 38, without any object inserted in the introducer 24, is closed (FIG. 3). Furthermore, the side valve 40 is also closed with the turn knob 42 (FIG. 2) turned to the closed position.

Figure 4B:
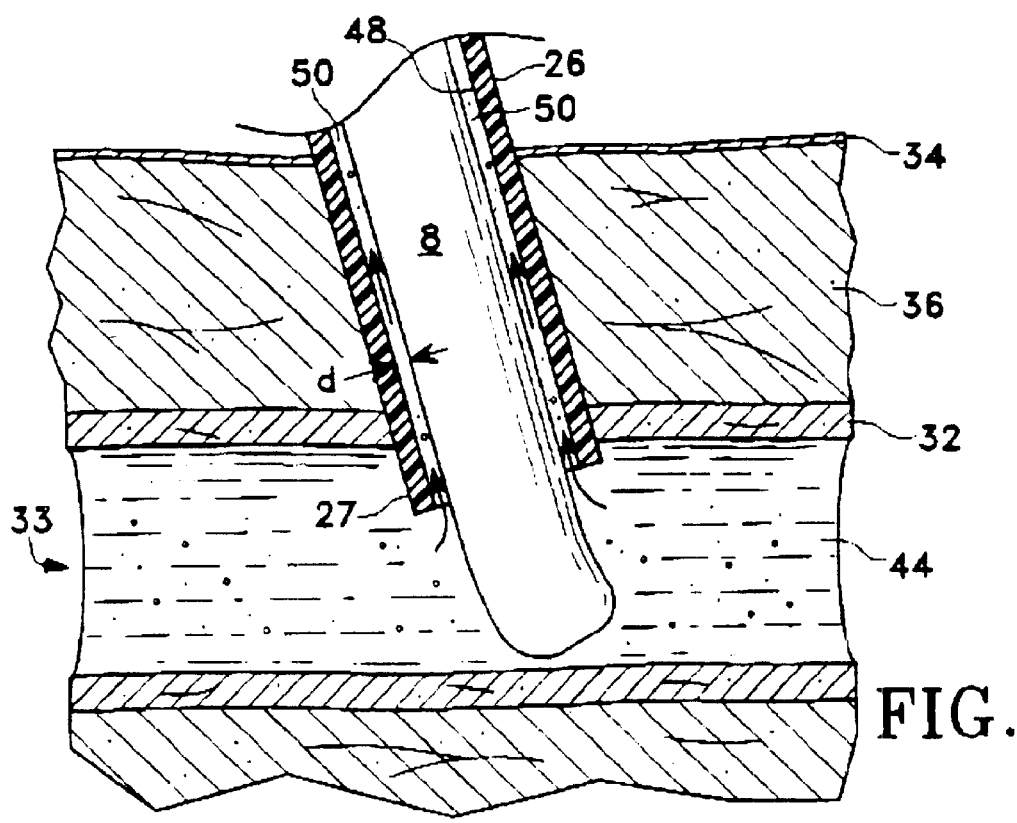

While the side valve 40 remains closed, the position guide 8 is inserted into the introducer sheath 26 through the orifice 46 of the septum 38 located inside the introducer body 28. The position guide 8 has to be inserted beyond the distal end 27 of the introducer sheath 26 as shown in FIG. 4B. The relative position of the position guide can be estimated by reading the marking 14 exposed outside the introducer body 28 (FIG. 2). For example, to extend the position guide 8 approximately 2.5 cm beyond the distal end 27 of the introducer sheath 26 as shown in FIG. 4B, the position guide 8 has to be inserted into the introducer body 28 until the marking I approximately coincides with the proximal end 29 of the introducer body 28, as shown in FIG. 3.

At this juncture, the valve 40 is intermittently turned on and off via the manipulation of the control knob 42 for the purpose of fathoming the position of the introducer sheath 26 with respect to the artery 33 as hereinafter described.

As mentioned before, the introducer sheath 26 has a bore 48 (FIGS. 4A and 4B). The cross-sectional dimension of the position guide 8 is slightly smaller than the corresponding cross-sectional dimension of the sheath bore 48. Thus, when the position guide 8 is inserted into the introducer sheath 26 as shown in FIG. 4B, a volume of gap space 50 separates the position guide 8 from the introducer sheath 26. The separation of the guide 8 to the sheath 26 is labeled "d" in FIG. 4B. With the introducer sheath 26 still inserted into the artery 33, blood 44 flows through the gap space 50. Thus, when the valve 40 is turned on via the knob 42 (FIG. 2), blood 44 can be seen flowing through the valve 40.

Figure 4C:
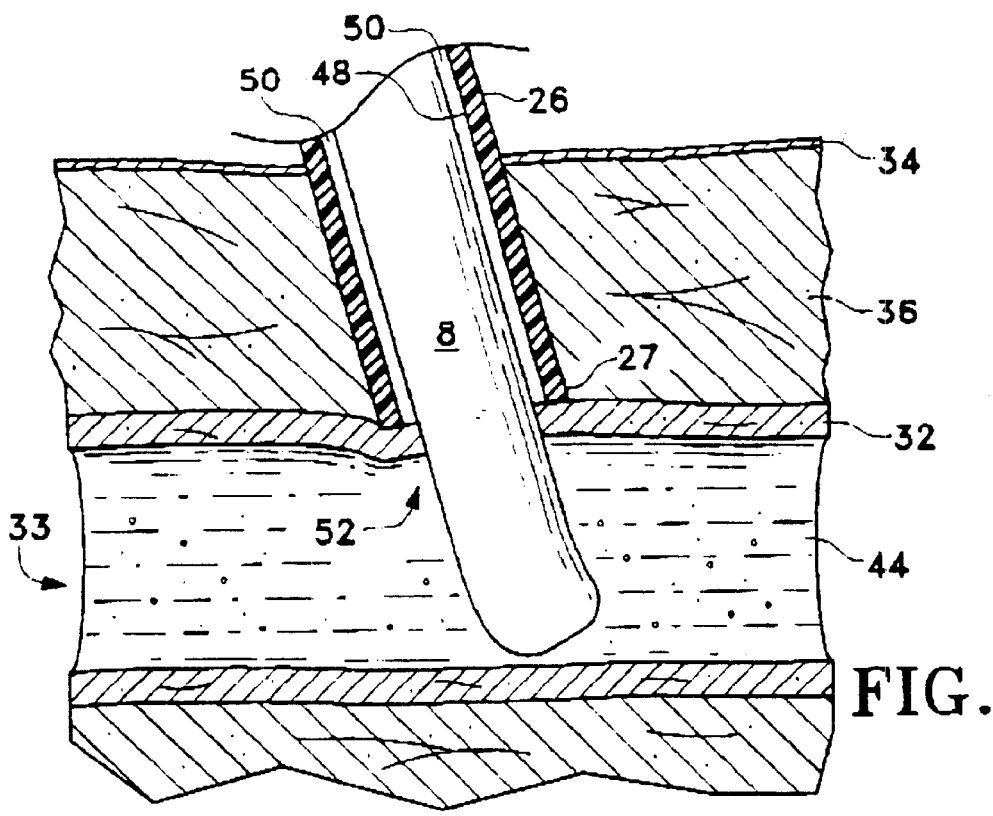

The position guide 8 is then held stationary. The introducer sheath 26 is slowly retracted away from the artery 33. With the valve 40 (FIG. 2) turned on and the introducer 24 gradually pulled away from the artery 33, there is a point in time in which the blood flow through the valve 40 suddenly ceases. The position of the distal end 27 of the introducer sheath 26 at this juncture is barely out of the artery 33 and is still in contact with the artery wall 32, as shown in FIG. 4C.

The reason for the cessation of blood flow is because the introducer sheath 26 has been pulled out of the artery 33. The natural elasticity of the artery wall 32 at the puncture opening of the artery 33 allows the puncture opening to shrink and grip onto the position guide 8. As such, blood is stopped from flowing into the gap space 50 resulting in the lack of blood flow even with the valve 40 turned on via the knob 42 (FIG. 2).

The position guide 8 in conjunction with monitoring of blood flow in the gap space 50 constitute a depth sensing mechanism. Specifically, monitoring of blood flow in the gap space 50 provides feedback to the operator (not shown) in determining the depth of the introducer sheath 26 with respect to the artery 33. Accurate positioning of the introducer sheath 26 is a prelude for precise implant placement as will be seen later.

Figure 4D:
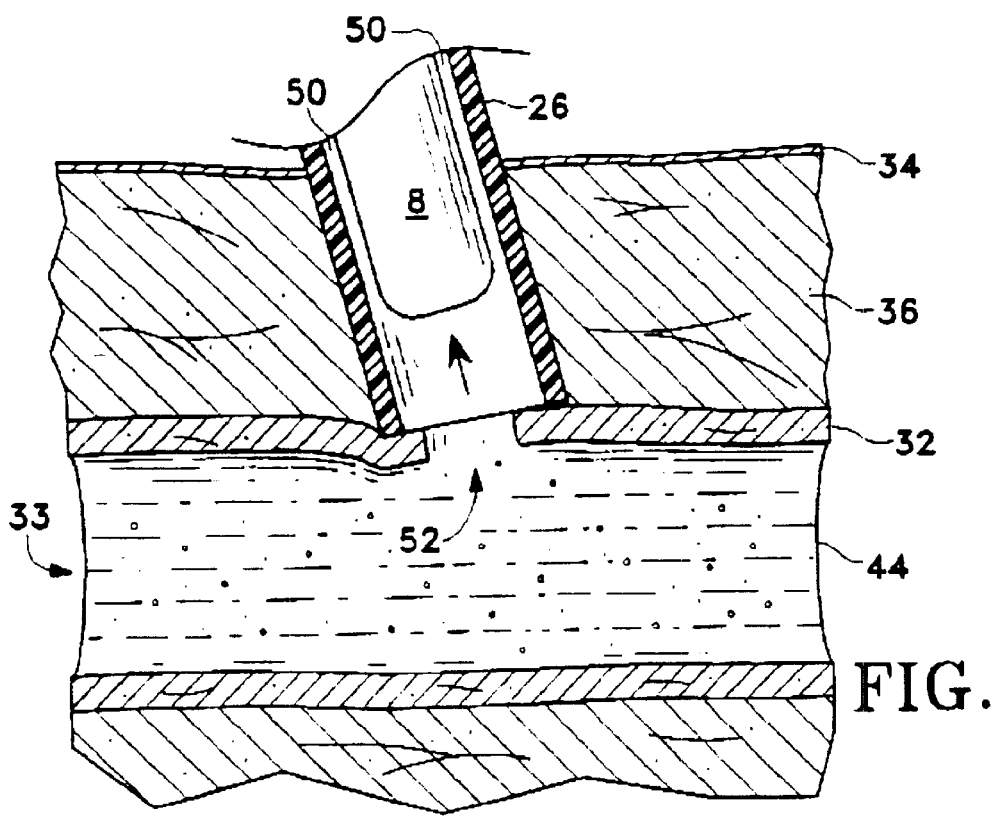

The blood monitoring valve 40 is then turned off. The next step is the complete withdrawal of the position guide 8 from the patient. FIG. 4D illustrates the position guide 8 as being in the middle of the withdrawing process.

Figure 4E:
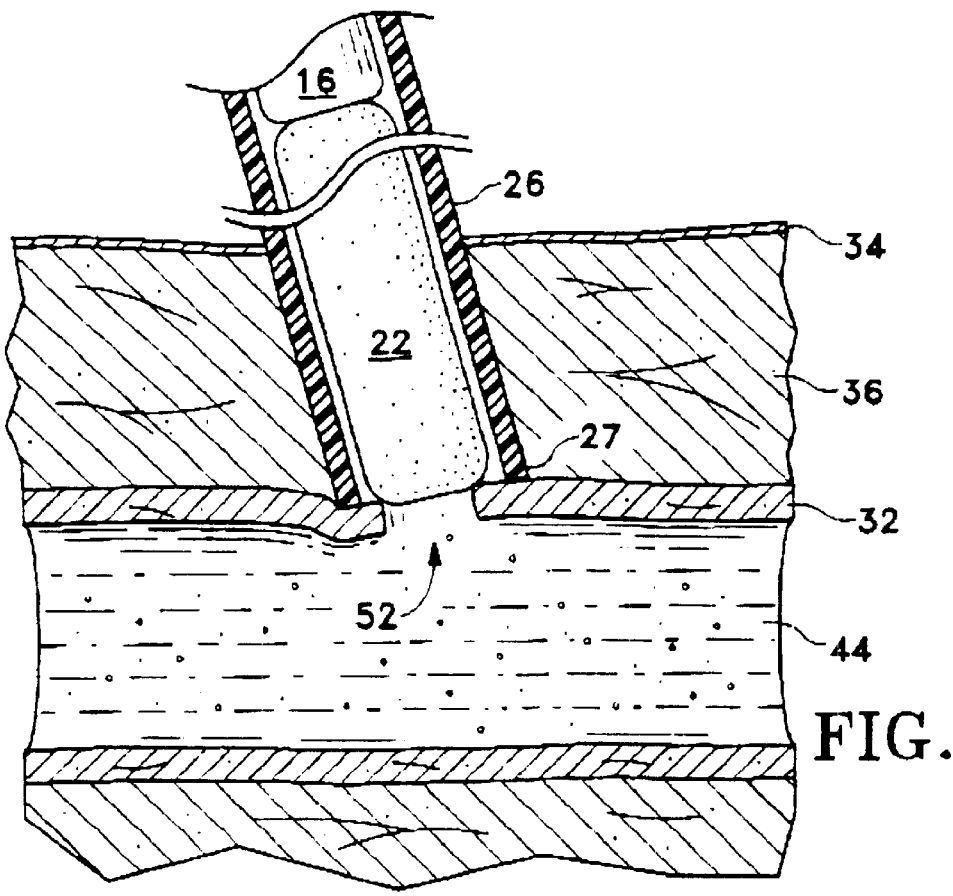

What follows is the step of deploying the implant 22. Reference is now directed to FIGS. 2 and 3. After the complete withdrawal of the position guide 8 from the introducer 24, the delivery rod 16 with the implant 22 attached thereto or associated therewith is inserted into the introducer 24 through the orifice 46 of the septum 38. The insertion process continues until the mark "II" is barely above the proximal end 29 of the introducer sheath 26. The position of the delivery rod 16 with the implant 22 at the distal end 27 of the introducer sheath 26 at this step is as shown in FIG. 4E. Specifically, the implant 22 is delivered at and sits atop the puncture opening of the artery wall 32 at the puncture site 52, no further and no closer. The reason the implant 22 can be precisely delivered is because the length between the mark "II" to the distal end 23 of the delivery rod 16 is equal to the length of the introducer 24 from the distal end 27 to the proximal end 29. As explained before, if the implant 22 is delivered beyond the puncture opening of the artery wall 32 into the blood stream 44, embolism may result. On the other hand, if the implant 22 is delivered midway in the tissue 36 without reaching the puncture opening of the artery 32, hematoma may be the consequence. The puncture wound sealing method of the invention allows the implant 22 to be accurately deployed as intended.

Figure 4F:
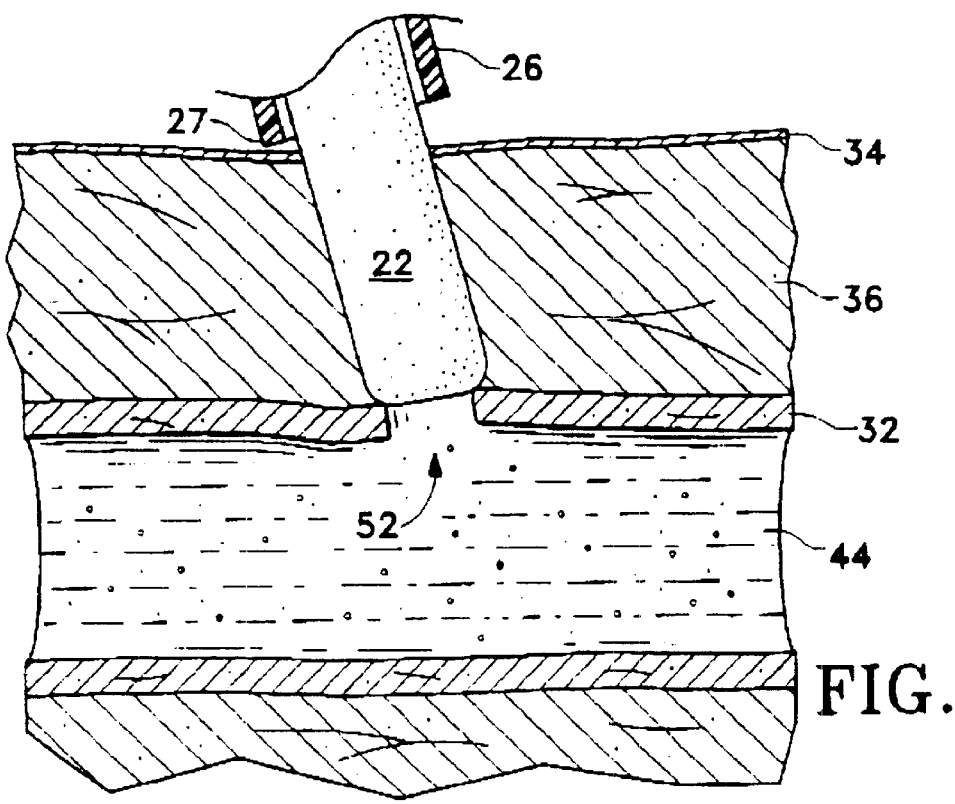

Thereafter, the introducer sheath 26 is completely withdrawn. FIG. 4F shows the introducer sheath 26 as in the process of being withdrawn.

Figure 4G:
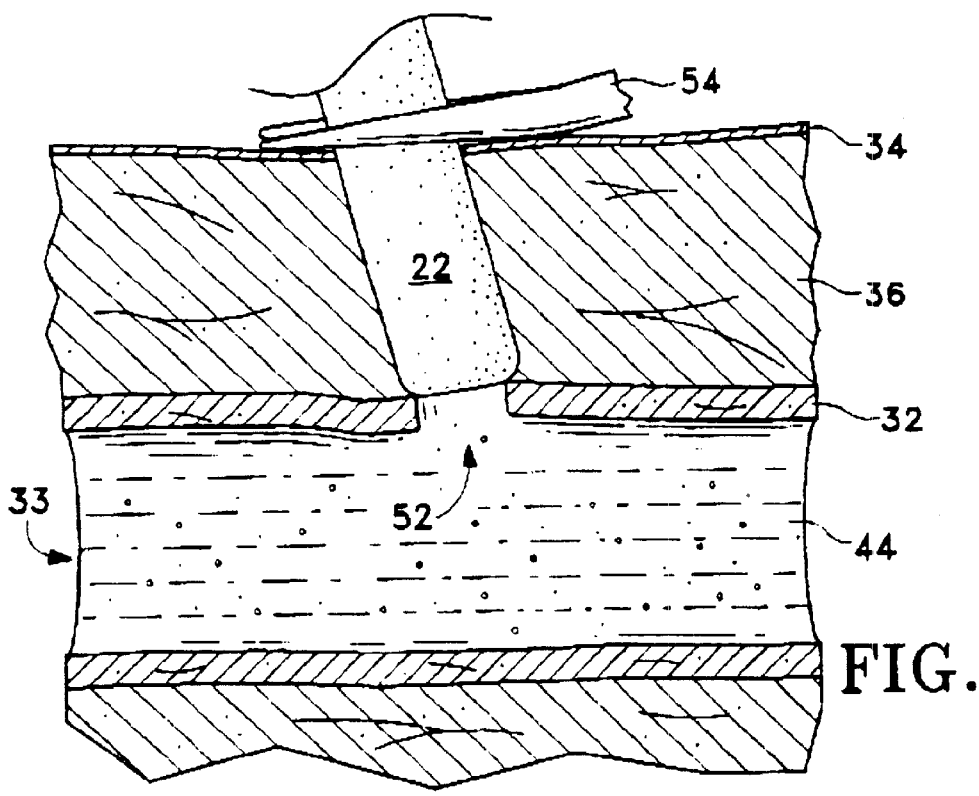

The excess length of the deployed implant 22 needs to be trimmed. For example, excess length of the implant 22 can be trimmed by a trimming tool 54, as shown in FIG. 4G.

Figure 4H:
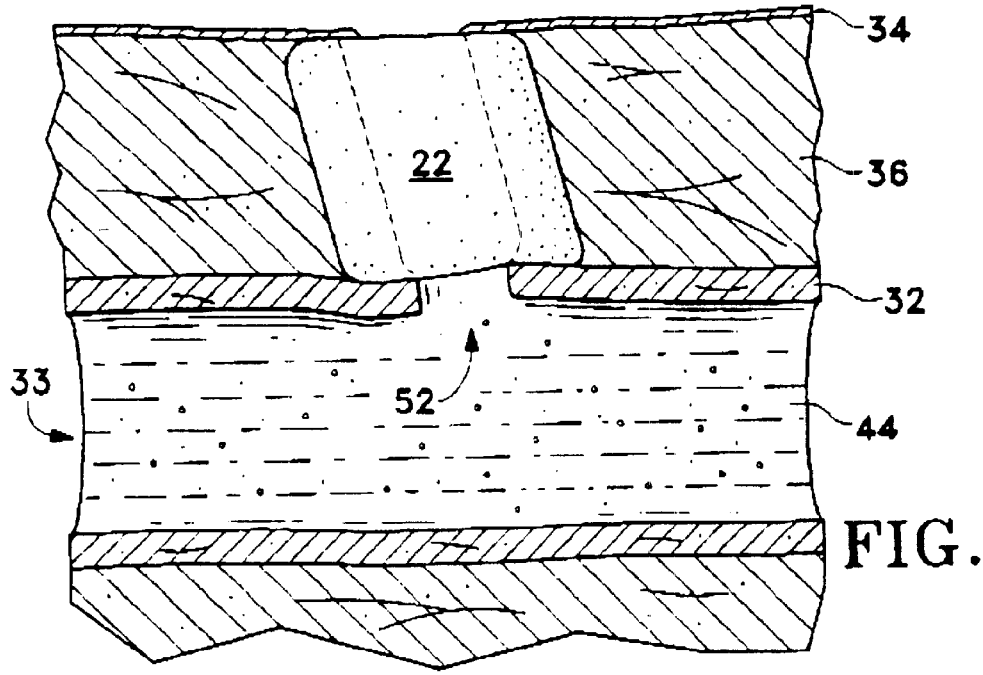

In a matter of minutes, very often in approximately 2 to 3 minutes, the implant swells by itself resulting in a tight seal of the tissue 36 at the puncture wound site 52 as shown in FIG. 4H.

Preformed Implant Design and Materials

Figure 5:
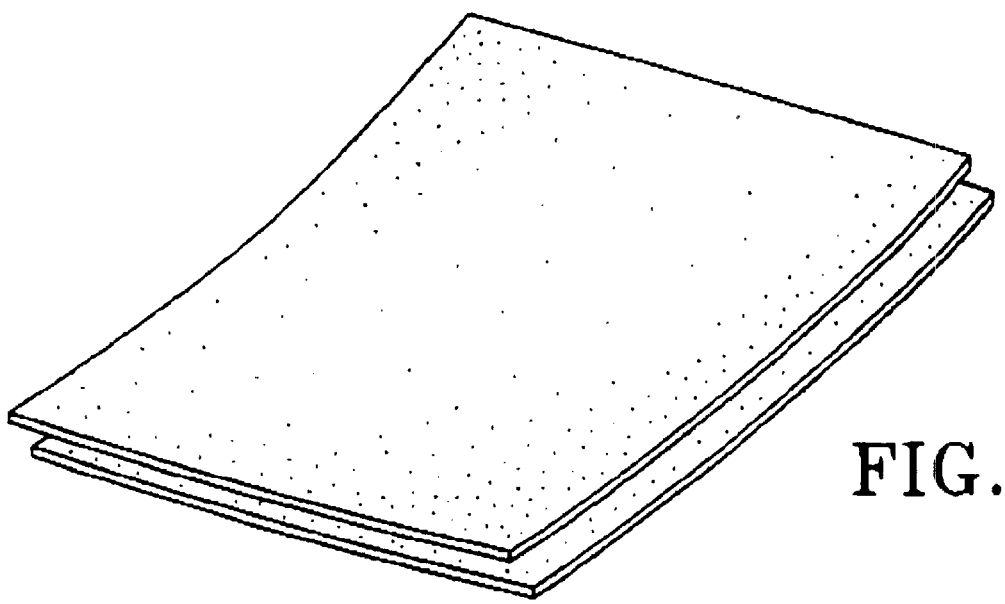
FIG. 5 is a perspective view of the base layers made of different materials which are foldable into an implant.
Figure 6:
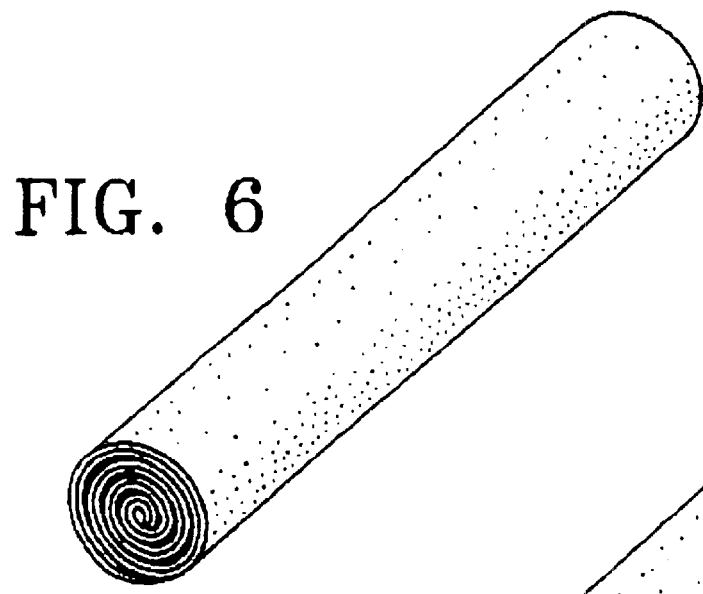
FIG. 6 is a perspective view of the implant folded from the layers shown in FIG. 5.
Figure 7:
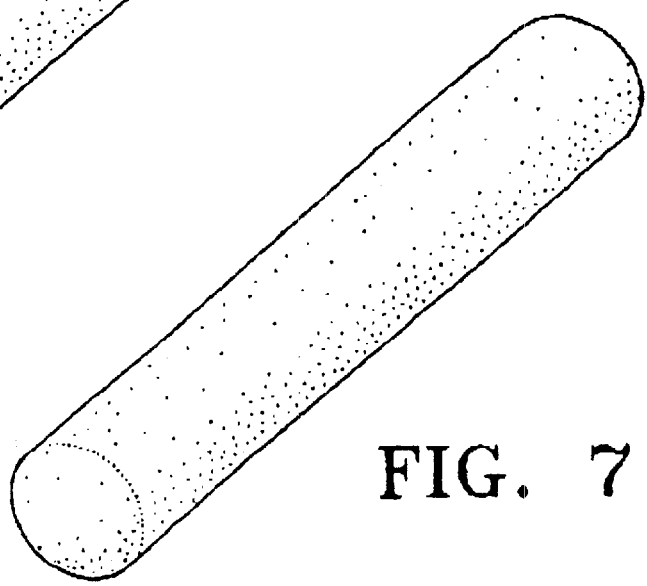
FIG. 7 is a perspective view of another implant made of a homogenous material.

Reference is now directed to FIGS. 5–7. The preferred implant 22 comprises a biocompatible, swellable, resorbable and preferably essentially non-porous biodegradable matrix. By "preformed", it is meant that the implant matrix is essentially already locked in place, i.e. covalent bonds between various implant materials have already been formed, and the implant is generally preformed and dried. Similar implants for use in another application have previously been generally described in the literature. See, for example, Published PCT Application No. 98/30252. Prior to administration, the implant 22 is in a nonexpanded state. As more fully described hereinafter, once the implant 22 is delivered to the site of administration, it swells in size.

Matrix materials that are suitable for producing the implants described herein include natural or synthetic polymers, proteins, polysaccharides, lipids, carbohydrates, and mixtures thereof. A preferred implant matrix comprises at least some (>10% by weight) synthetic hydrophilic polymer, such as polyalkalene oxide, and more preferably polyethylene glycol. See U.S. Pat. No. 5,874,500 for a description of such synthetic hydrophilic polymers. These types of polymers have good rehydration properties which facilitates swelling after implantation. In a particularly preferred embodiment, the implant comprises a mixture of a synthetic hydrophilic polymer and: a protein, which can be any naturally occurring or synthetic protein, but is preferably collagen, gelatin or fibrin; or a carbohydrate, such as glycosaminoglycan, or the like. In a particularly preferred embodiment, the implant comprises a mixture of polyethylene glycol and gelatin in a weight ratio of polyethylene glycol:gelatin of between .1:9.9 to 9.9:.1, and more preferably from 1:9 to 9:1, and most preferably from 3:1 to 1:3. Such composite matrices have the unexpected property of improved expansion characteristics and pressure resistance when compared to matrices consisting of polyethylene glycol alone. See Examples 1 and 2 below.

As depicted in FIG. 5, the implant may be formed from two (or more) layers having differing compositions. For example, one of layers may comprise a dried collagen sheet as prepared according to well know procedures for preparing collagen-based implantable materials of various shapes and configurations. The other layer may comprise a dried synthetic hydrophilic polymer in the form of a sheet. Such hydrophylic polymers have been described previously in the scientific literature for use in preparing implantable materials having different shapes. It would be easy for one of skill in the art to adapt these procedures for the preparation of sheets of collagen and synthetic polymers, that are then rolled together as depicted in FIG. 6 to prepare the implants described herein. This multilayered format may result in enhanced expansion due to the increased surface area.

In another embodiment as depicted in FIG. 7, the implant comprises a uniform matrix of a biomaterial. It should be pointed out that as depicted in FIGS. 6 and 7, the implant is cylindrical in shape, although it should be readily apparent that alternative implant designs and devices can easily be fashioned based on the teachings herein to deliver a non-cylindrical implant (e.g. an implant having a cross section that is oval, square, pentagonal, star-shaped, as opposed to being spherical.)

The implant is generally formed in a two-step process comprising the steps of matrix formation and drying. During the step of matrix formation, the biomaterial from which the implant will be formed is shaped or molded into the desired configuration. In a preferred embodiment, matrix formation is accomplished by mixing the biomaterial(s) with a suitable crosslinking agent to effect crosslinking of the biomaterial(s) into a three dimensional matrix. Crosslinking can also be accomplished using other methods, such as heat, irradiation, and the like. In some instances, the biomaterial becomes mechanically crosslinked merely upon drying of the implant.

In most instances, the matrix will shrink upon drying. It is also possible to facilitate shrinkage and compress the matrix by applying pressure to the matrix, either before or after drying. In any event, in order to be "swellable" after implantation, it is generally the case that the matrix shrinks after formation, and/or before or after drying to result in a nonexpanded implant that is ready for administration that will swell, preferably to at least twice its original (pre-dryed and pre-compressed) diameter upon contact with bodily fluids after implantation. The nonexpanded implant is preferably essentially nonporous, which intends that the average pore size is less than 500 nm. As such, the implant is capable of maintaining is structural integrity throughout preparation, shipping and handling, and administration, as opposed to more porous implants that may become cracked or flaked, which increases the risk of introduction of foreign bodies into the bloodstream during implantation. Implants that comprise mixtures of synthetic hydrophilic polymers and proteinaceous materials also generally have the property of being somewhat more flexible than implants that consist of a single component, such as the collagen implants described in U.S. Pat. No. 5,571,181 to Li.

Other optional matrix materials may also be included, such as biologically active agents, clotting factors and the like. Such optional matrix materials are described generally in PCT Published Application No. WO 98/30252.

In-situ Matrix Forming Implant Design and Materials

Although the preferred implant is preformed prior to administration, in an alternate embodiment, the implant may also be in a liquid or gel state at the time of administration and form or continue to form a matrix after administration. Accordingly, any biocompatible matrix-forming biomaterials or combination of biomaterials may be used, so long as the matrix formed after administration has sufficient strength to remain in-tact for a desirable period of time. Such materials are well know in the literature, and are also described herein as starting materials for formation of a preformed implant.

In general, when the implant is in liquid form, it usually comprises two or more separate liquid components that are capable of reacting to form a covalently crosslinked matrix after administration. Such two-component compositions are described in U.S. Pat. Nos. 5,752,974; and 5,874,500. These compositions can be premixed and delivered using the apparatus described herein. Alternatively, compositions that do not require premixing but that remain in liquid or gel form prior to exposure to tissues can also be delivered using the apparatus described herein and thereafter form a matrix due to a change in pH, exposure to clotting factors, etc.

A preferred characteristic of in situ matrix forming biomaterials for use in the practice of the present invention is that they be capable of rapidly forming a matrix after administration. Two-part compositions are particularly well suited for such use. The two-part compositions that are useful for formation of in situ matrix forming implants comprise two different compounds, each within a separate part of the composition and at least one of which is a polymer, that react with one another to form a covalently crosslinked gel matrix. As such, they can easily be administered separately, and rapidly form gels at the site of administration.

In the compositions of the in situ matrix forming implants, each component is present in one of the two separate parts, or "components", of the composition, along with other optional ingredients as described elsewhere herein. The two reactive compounds and the gel matrix that forms when they are mixed together can be represented by Formula I as follows:

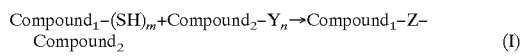

$$\text{Compound}_1\text{-(SH)}_m + \text{Compound}_2\text{-Y}_n \rightarrow \text{Compound}_1\text{-Z-Compound}_2 \quad (I)$$

Compound$_1$ has multiple (m≧2) sulfhydryl groups (SH) that react with Compound$_2$, which has multiple (n≧2) sulfhydryl-reactive groups (Y). It should be understood that sulfhydryl groups are also "sulfhydryl reactive groups", since it is well known that sulfhydryl groups will react with one another under certain conditions. When mixed together, the two compounds become interconnected via a covalent bond (Z). When m+n>5, and appropriate ratios of the two components are utilized as described elsewhere herein, the two compounds form multiple attachments to one another resulting in a three-dimensional polymer matrix. Preferably, both compounds contain four or more functional groups, since such multifunctionality results in a gel matrix with greater overall cohesive strength. In a particularly preferred embodiment, each of the compounds is tetrafunctionally activated.

In another preferred embodiment, the compounds each have 12 functional groups. Such compounds are formed from reacting a first tetrafunctionally activated polymer with a second tetrafunctionally activated polymer, wherein the functional groups of each of the two compounds are a reaction pair, and react together to form "12-arm" functionally activated polymers. An example of such a "12-arm" compound is dodeca-sulfhydryl-PEG, 50,000 mol. wt., which is constructed from a core tetra-functional succinimide ester PEG coupled to four (exterior) tetra-functional sulfhydryl-PEG molecules. Such polymers range in size from over 10,000 mol. wt. to greater than 100,000 mol. wt. depending on the molecular weight of the tetra-functionally activated polymer starting materials.

Other types of multifunctional polymers can easily be synthesized using routine synthesis. However, care should be taken to produce multi-arm products with consistent arm lengths to avoid stearic hindrance of the reactive groups. Accordingly, activated polymers that are suitable for use to form implants in situ may have a variety of geometric shapes and configurations.

a. Compound Core

As described above, each of the compounds has multiple functional groups, either sulfhydryl groups or sulfhydryl-reactive groups. The non-reactive remainder of the compound is considered to be its "core". At least one of the two compounds must have a polymer core in order to form an efficient gel matrix. When one of the compounds contains a polymer core, the other compound can be a small organic molecule with multiple sulfhydryl-reactive groups. However, for most applications, it is preferred for both compounds to have the same or a different polymer core.

The polymer core may be a synthetic polyamino acid, a polysaccharide, or a synthetic polymer. A preferred polymer core material is a synthetic hydrophilic polymer. Suitable synthetic hydrophilic polymers include, inter alia, polyalkylene oxide, such as polyethylene oxide (($CH_2CH_2O)_n$), polypropylene oxide (($CH(CH_3)CH_2O)_n$) or a polyethylene/polypropylene oxide mixture (($CH_2CH_2O)_n$–($CH(CH_3)CH_2O)_n$). A particularly preferred synthetic hydrophilic polymer is a polyethylene glycol (PEG) having a molecular weight within the range of about 100 to about 100,000 mol. wt., more preferably about 1,000 to about 20,000 mol wt. More preferably still, when the polymer core is polyethylene glycol, it generally has a molecular weight within the range of about 7,500 to about 20,000 mol. wt.. Most preferably, the polyethylene glycol has a molecular weight of approximately 10,000 mol. wt.

Multifunctionally activated polyalkylene oxides, such as polyethylene glycol, are commercially available, and are also easily prepared using known methods. For example, see Chapter 22 of *Poly(ethylene Glycol) Chemistry: Biotechnical and Biomedical Applications,* J. Milton Harris, ed., Plenum Press, NY (1992); and Shearwater Polymers, Inc. Catalog, *Polyethylene Glycol Derivatives,* Huntsville, Ala. (1997–1998). A preferred combination of activated polymers is as follows: the sulfhydry-reactive group-containing compound is the tetrafunctional PEG, pentaerythritol poly(ethylene glycol) ether tetra-succinimidyl glutarate (10,000 mol. wt.); and the sulfhydryl group-containing compound is the tetrafunctional PEG, pentaerythritol poly(ethylene glycol) ether tetra-sulfhydryl (10,000 mol. wt.). In both cases, these "four-arm" PEGs are formed by ethoxylation of pentaerythritol, where each of the four chains is approximately 2,500 mol. wt., and then derivatized to introduce the functional groups onto each of the four arms. Also preferred are analogous poly(ethylene glycol)-like compounds polymerized from di-glycerol instead of pentaerythritol.

When only one of the reactive compounds comprises a polymer core, the other reactive compound can be a multifunctionally active small organic molecule. Such compounds include the di-functional di-succinimidyl esters and di-maleimidyl compounds, as well as other well known commercially available compounds (Pierce Chemical Co., Rockford, Ill.). In addition, one of skill in the art could easily synthesize a low molecular weight multi-functional reactive compound using routine organic chemistry techniques. On such compound is shown in FIG. 2, which is a pentaerythritol coupled to four glutarates, with each arm capped with N-hydroxy-succinimidyl esters (NHS). Analogous compounds can be synthesized from inositol (radiating 6 arm), lactitol (9 arm) or sorbitol (linear 6-arm). The end-capped reactive group can just as easily be sulfhydryl, maleimidyl, vinyl-sulfone, etc., instead of NHS. The polymer or the small molecule can carry either reactive end group as long as there are reactive pairs in the composition such as NHS and SH, maleimidyl and SH, etc.

b. Reactive Groups and Matrix Linkages

In the in situ matrix forming implant compositions, the linkage, Z, comprises a covalent bond between the sulfur atom in the sulfhydryl group-containing compound and, e.g., the carbon or sulfur atom in the sulfhydryl-reactive group-containing compound. Accordingly, the linkage may be a thioester, a thioether, a disulfide, or the like. A wide variety of sulfhydryl-reactive groups and the types of linkages they form when reacted with sulfhydryl groups are well known in the scientific literature. For example, see Bodanszky, M., *Principles of Peptide Synthesis,* 2nd ed., pages 21 to 37, Springer-Verlog, Berlin (1993); and Lundbland, R. L., *Chemical Reagents for Protein Modification,* 2nd ed., Chapter 6, CRC Press, Boca Raton, Fla. (1991).

For most applications, sulfhydryl reactive groups that react with sulfhydryl groups to form thioester linkages are preferred. Such compounds include, inter alia: mixed anhydrides, such as PEG-glutaryl-acetyl-anhydride, PEG-glutaryl-isovaleryl-anhydride, PEG-glutaryl-pivalyl-anhydride and related compounds as presented in Bodanszky, supra, p. 23; Ester derivatives of phosphorus; ester derivatives of p-nitrophenol, pentafluorophenol, and related active esters as presented by Bodanszky, supra, pp. 31–32, esters of substituted hydroxylamines, such as those of N-hydroxy-phthalimide, N-hydroxy-succinimide, and N-hydroxy-glutarimide, as well as related structures in Bodanszky, supra, Table 3; esters of 1-hydroxybenzotriazole, 3-hydroxy-3,4-dihydrobenzotriazine-4-one and 3-hydroxy-3,4-dihydroquinazoline-4-one; derivatives of carbonylimidazole; and isocyanates. With these compounds, auxiliary reagents can also be used to facilitate bond formation, such as 1-ethyl-3-[3-dimethylaminopropyl] carbodiimide can be used to facilitate coupling of carboxyl groups (i.e., glutarate and succinate) with sulfhydryl groups.

In addition to the sulfhydryl reactive compounds that form thioester linkages, various other compounds can be utilized that form other types of linkages. For example, compounds that contain methyl imidate derivatives form imido-thioester linkages with sulfhydryl groups. Alternatively, sulfhydryl reactive groups can be employed that form disulfide bonds with sulfhydryl groups, such as ortho pyridyl disulfide, 3-nitro-2-pyridenesulfenyl, 2-nitro-5-thiocyanobenzoic acid, 5,5'-dithio-bis(2-nitrobenzoic acid), derivatives of methane-thiosulfate, and 2,4-dinitrophenyl cysteinyl disulfides. In such instances, auxiliary reagents, such as the hydrogen peroxide or di-tert-butyl ester of azodicarboxylic acid, can be used to facilitiate disulfide bond formation.

Yet another class of sulfhydryl reactive groups form thioether bonds with sulfhydryl groups. Such groups include, inter alia, iodoacetamide, N-ethylmaleimide and other maleimides, including dextran maleimides, monobromo-bimane and related compounds, vinylsulfones, epoxides, derivatives of O-methyl-isourea, ethyleneimines, aziridines, and 4-(aminosulfonyl-)7-fluoro-2,1,3-benzoxadiazole.

c. Chain Extenders

Functional groups may be directly attached to the compound core, or they may be indirectly attached through a chain extender. Such chain extenders are well known in the art. See, for example, PCT WO 97/22371, which describes "linking groups" that would be suitable for use as chain extenders in the compositions of the present invention. Chain extenders are useful to avoid stearic hindrance problems that are sometimes associated with the formation of direct linkages between molecules. Alternatively, chain extenders may be used to link several multifunctionally activated compounds together to make larger molecules. In a particularly preferred embodiment, the chain extender can also be used to alter the degradative properties of the compositions after administration and resultant gel formation. For example, chain extenders can be incorporated into one or both of the multifunctionally activated polymers to promote hydrolysis, to discourage hydrolysis, or to provide a site for enzymatic degradation. Chain extenders can also activate or suppress activity of sulfhydryl and sulfhydryl-reactive groups. For example, electron-withdrawing groups within one or two carbons of the sulfhydryl group would be expected to diminish its effectiveness in coupling, due to a lowering of nucleophilicity. Double-bond carbon and carbonyl carbon would be anticipated to have this effect. Bulky nearby groups for either partner are anticipated to diminish coupling rates, due to steric hindrance. Electron-withdrawing groups adjacent to the reactive carbonyl of glutaryl-N-hydroxysuccinimidyl would be anticipated to make this carbonyl carbon even more reactive with the sulfhydryl partner.

Chain extenders may provide sites for degradation, i.e., hydrolysable sites. Examples of hydrolysable chain extenders include, inter alia, alpha-hydroxy acids such as lactic acid and glycolic acid; poly(lactones) such as caprolactone, valerolactone, gamma butyl lactone and p-dioxanone; poly (amino acids); poly(anhydrides) such as glutarate and succinate; poly(orthoesters); poly(orthocarbonates) such as trimethylene carbonate; and poly(phosphoesters). Examples of non-degradable chain extenders include, inter alia, succinimide, propionic acid and carboxymethylate. See, for example, PCT WO 99/07417. Examples of enzymatically degradable chain extenders include Leu-Gly-Pro-Ala, which is degraded by collagenase; and Gly-Pro-Lys, which is degraded by plasmin.

d. Gel Strength and Gel Time

The compositions of the in situ matrix forming implants are formulated to exhibit adequate strength and rapid gel time. The elastic modulus, G', is the preferred measure of gel strength. Preferred compositions for use as tissue sealants can achieve a gel strength of about $10^3$ to $10^8$ dynes/cm$^2$, and more preferably $10^5$ to $10^8$ dynes/cm$^2$.

The gel time of preferred formulations is less than 60 seconds, more preferably less than 30 seconds, and most preferably less than 15 seconds. The fast gel time ensures maximum material at the site to be treated and sufficient mechanical properties.

e. Optional Composition Constituents

In addition to the reactive compounds, the compositions of the in situ matrix forming implants may also contain other compounds, which may be included in one or both of the components of the two-component compositions, or may be separately administered. In one embodiment, these compounds may become covalently incorporated into the matrix itself by becoming crosslinked to one or both of the reactive compounds after they are mixed together. In another embodiment, such as would be the case if the compound was unreactive with either of the reactive compounds, the compound may be administered in such a way that it become physically or ionically associated with the matrix-forming compounds after mixing, and thus become part of the matrix itself.

Additional compounds that may be added are glycosaminoglycans and proteins. Suitable glycosaminoglycans include, inter alia, hyaluronic acid, chitin, chondroitin sulfate A, B, or C, keratin sulfate, keratosulfate and heparin, and derivatives thereof. In another embodiment, proteins can be added for a variety of purposes. For example, collagen may improve biocompatibility of the matrix, including the potential colonization by cells, promotion of would healing, etc. Collagen and any amino group-containing proteins would also contribute to the structural integrity of the matrix by becoming crosslinked thereto along with the other matrix components. In particular, if PEG-succinimidyl esters are used, the amide bonds formed with collagen will be more stable to hydrolytic degradation than the bonds formed by the reaction of succinimidyl esters and sulfhydryls.

Suitable proteins include, inter alia, collagen, fibronectin, gelatin and albumin, as well as peptide fragments thereof. Particularly preferred is collagen, which may be in the form of afibrillar, microfibrillar or fibrillar collagen. Types I and III collagen isolated from bovine corium or human placenta, or prepared by recombinant DNA methods, are suitable. See PCT WO 90/05755 for a description of suitable collagens and collagen derivatives. It should be understood that when adding collagen to the composition, it is important to adjust the concentration of the other composition components to avoid precipitation.

Additional constituents which may be added to the composition include antibiotics, growth factors, hemostatic proteins (such as thrombin, fibrin, fibrinogen, the blood factors, etc.), cells, genes, DNA, etc.

f. Composition Formulation

The compositions of the in situ matrix forming implants of the present invention generally comprise two separate parts, or "components". Both components can be mixed together in a single aqueous medium in which they are both unreactive, i.e. such as in a low pH buffer. Thereafter, they can be sprayed onto the tissue site along with a high pH buffer, after which they will rapidly react and form a gel. This embodiment is described in Example 9.

The concentration of the reactive compounds in each of the composition components necessarily depends on a number of factors. For example, if the composition components are each 4-arm PEGs (i.e. PEG-PEG compositions), a concentration of 20–25% by weight in each of the two components before mixing results in a gel after mixing with an elastic modulus, G', of approximately $10^5$–$10^6$ dynes/cm$^2$, which is adequate for use as a surgical sealant. Using methylated collagen and 4-arm succinimidyl PEG, concentrations of 2–4% and 0.2–0.4%, respectively, result in gels with cohesive strengths that are comparable to PEG-PEG gels at 10–15%. Using albumin as one of the components, concentrations of 30% or more achieve a similar cohesive strength. The appropriate concentration of the compound, and other optional ingredients, in each component, and thus the relative concentration of the matrix components in the final gel matrix, can easily be optimized to achieve the desired gelation time and gel strength using routine experimentation. Using the preferred four-arm PEGs described above, the synthetic polymer is generally present at a concentration of 2 to 50% (w/v), and more preferably 10–25%.

The liquid components of the compositions are each separately prepared by adding the activated synthetic polymer (in dry form or as a concentrated solution) to a liquid medium. Suitable liquid media include aqueous buffer solutions, such as monobasic sodium phosphate/dibasic sodium phosphate, sodium carbonate/sodium bicarbonate, glutamate or acetate, at a concentration of 0.5 to 300 mM. In general, the sulfhydryl-reactive PEG is prepared in water or a dilute buffer, with a pH of between around 5 to 6. Buffers with pKs between about 8 to 10.5 for preparing the sulfhydryl-PEG component are useful to achieve fast gelation time of compositions containing mixtures of sulfhydryl-PEG/SG-PEG. These include carbonate, borate and AMPSO (3-[(1,1-dimethyl-2-hydroxyethyl)amino]2-hydroxypropane-sulfonic acid). In contrast, using a combination of maleimidyl PEG and sulfhydryl-PEG, a pH of around 5 to 9 is preferred for the liquid medium used to prepare the sulfhydryl PEG. A particularly preferred composition comprises a mixture of maleimidyl and succinimidyl PEG as the first component, and sulfhydryl PEG as the second component. Such compositions produce gels with enhanced biodegradability and superior gel times when compared to compositions having only maleimidyl PEG or succinimicyl PEG alone.

g. High Strength Alternative Formulations

In addition to the formulations described above, high cohesive ("tensile") strength matrix-forming compositions are also well suited for use in the present invention, which contemplates that the matrix has a tensile strength of at least 10% and more preferably 20% of that of cyanoacrylate. Such high-strength compositions comprise at least one multi-functional synthetic polymer that, along with other composition constituents, can form a high strength matrix at the site of administration. Such compositions are designed to become anchored in place by mechanical and/or chemical means to seal tissue puncture openings. To achieve a "hight strength", it is preferred to also include a "filler" in the composition to enhance the strength of the matrix, as will be more fully described below.

In addition to the core materials described above, other polymers are also useful as core materials to form high strength in situ matrix forming implants. For example, polyesters, polymethacrylates, polycaprolactones, polyalkenes (such as polybutadiene) are also considered useful. Many of these materials have wide usage in the medical industry. For example, polycaprolactans are elements of Nylon-6; polypropylene is a constituent of medical implants; polymethacrylate is found in polymethyl-methacrylates and poly-hydroxy-methyl-methacrylates, which are constituents of medical implants; and polybutadiene is present in commercial rubber.

An exemplary non-polyalkylene oxide based composition is comprised of two different components, each comprising a different penta-erythritol based compound, such that the two compounds react with one another when mixed together to form a strong matrix. The first compound is penta-erythritol tetrakis (3-mercapto-proprionate) ("PESH-P"), and the second compound is pentaerythritol tetra-acrylate ("PETA"). A large variety of similar molecular structures (4-armed and radially symmetrical) can be synthesized based on penta-erythritol. The length of the molecular chains can be extended, preferably using non-alkyoxyl segments, such as polyester, polymethylene, polyamides, or other materials that are constituents of known biocompatible polymers.

Other radially branching molecules, such as glycerol or lactitol, can be utilized to construct gel-forming materials. The desired structures may be water-immiscible and low molecular weight (350 to about 12,000 mol. wt.) so as to remain liquid. Higher molecular weight gel-forming structures are also contemplated. It is preferred that such compositions are water miscible or water dispersable to be compatible with the use of water as the liquid medium for delivery.

In addition to the branched molecules described above, the compositions of the present invention can be formed from linear molecules. Such linear molecules can have molecular weights as high as 100,000 mol. wt., so long as they have biodegradable elements and sufficient functional groups.

As described above, in order to enhance matrix strength, it is generally desirable to add a "filler" to the composition. Fillers are described in the Encyclopedia of Polymer Science and Technology as, "Plastics, Resins, Rubbers, Fibers", Vol.

6, John Wiley & Sons, Inc., ed. (1970). Suitable fillers for use in the present invention include, inter alia, certain collagen fibers, polyglycolide and polylactide fibers, as well as other organic fillers and inorganic fillers. It is well-known that fillers can enhance the tensile strength of polymer compositions. For example, "silicone gums, when cross-linked with peroxides, are weak and cheesy, with tensile strengths on the order of only 50 lb/in$^2$ [1 lb/in$^2$=0.68 n/cm$^2$]. When suitably compounded with reinforcing fillers, the tensile strength of these gums may increase as much as fifty-fold." Lichtenwalner, H. K. and Sprung, M. N., in Mark, H. F., Gaylord, N. G., and Bikales, N. M., Eds., Encyclopedia of Polymer Science and Technology, Vol. 12, p. 535, John Wiley, N.Y., 1970. Suitable fillers are those that have inherent high tensile strength and also can interact by covalent or non-covalent bonds with the polymerized gel network. The filler should bond to the gel, either mechanically or covalently, in order to provide tensile support. Tensile strengths of polyglycolide resorbable sutures are approximately 89,000 N/cm$^2$; that of collagen fibers is 5000–10,000 N/cm$^2$ (Hayashi, T., in Biomedical Applic. of Polym. Mater., Tsuruta, T. et al., Eds., CRC Press, Boca Raton, Fla., 1993).

Alternative Apparatus Designs

Figure 8:
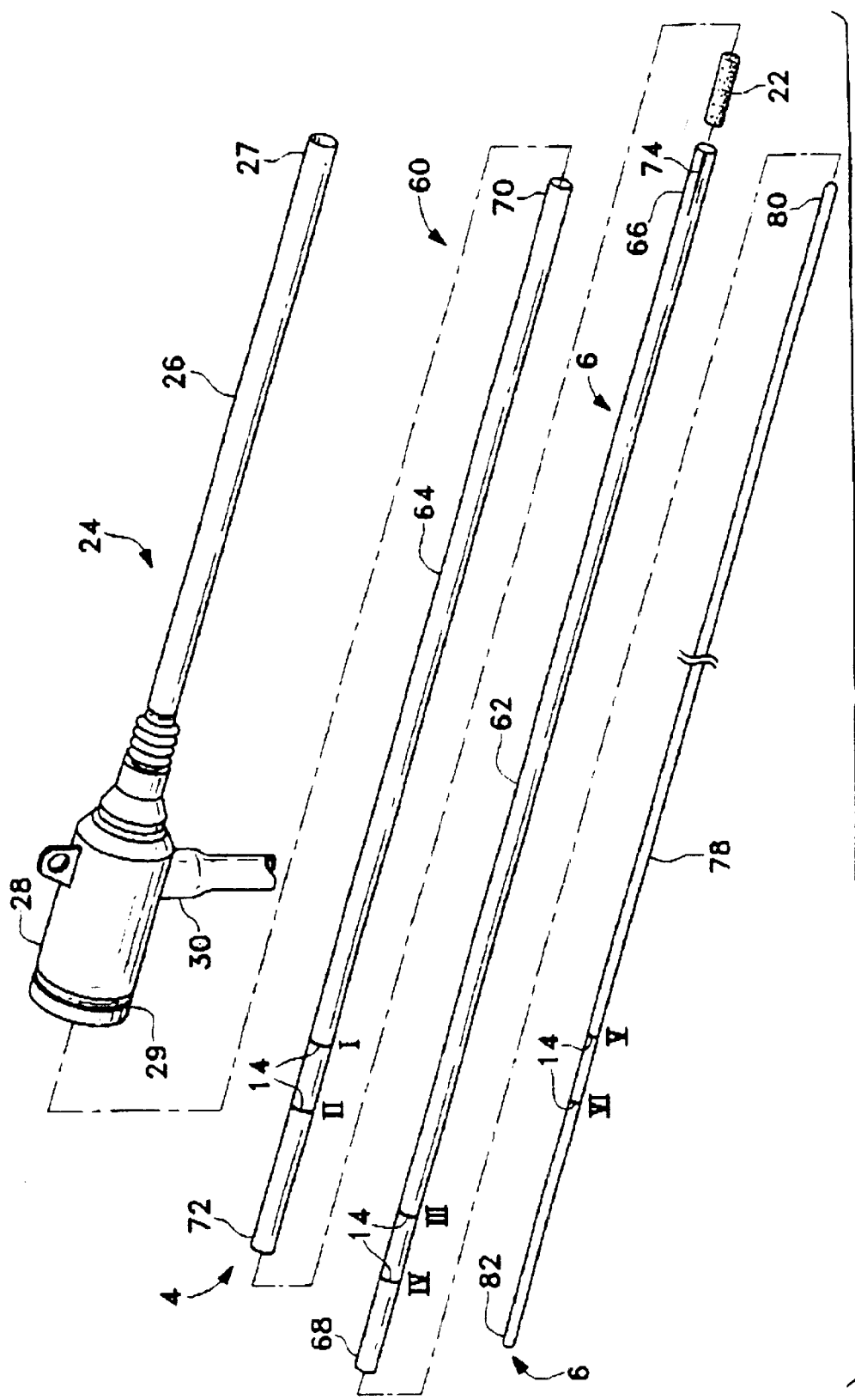
FIG. 8 is a perspective view of a second embodiment of the invention showing the various components.
Figure 9:
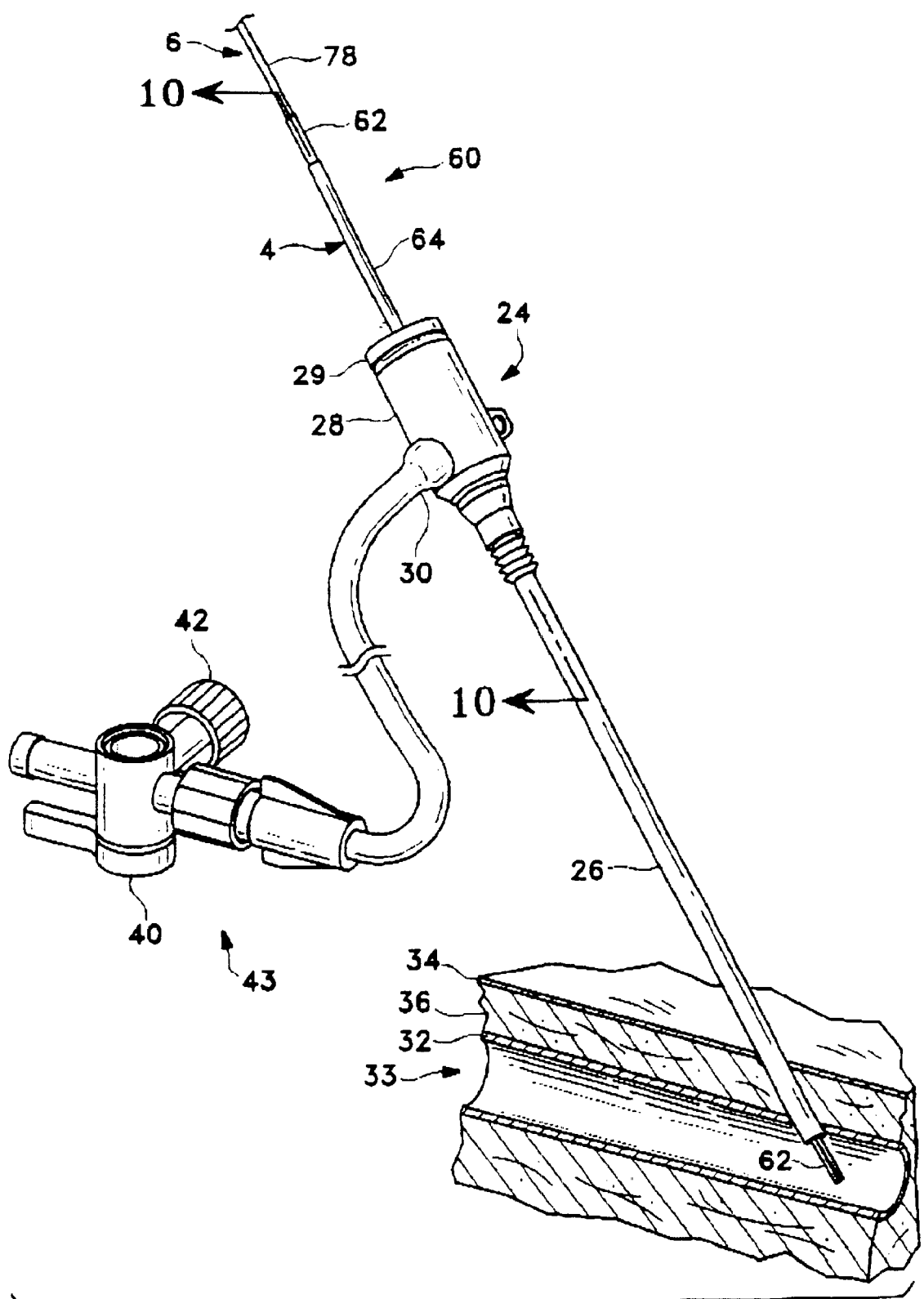
FIG. 9 is a perspective view of the second embodiment of the invention shown in application.
Figure 10:
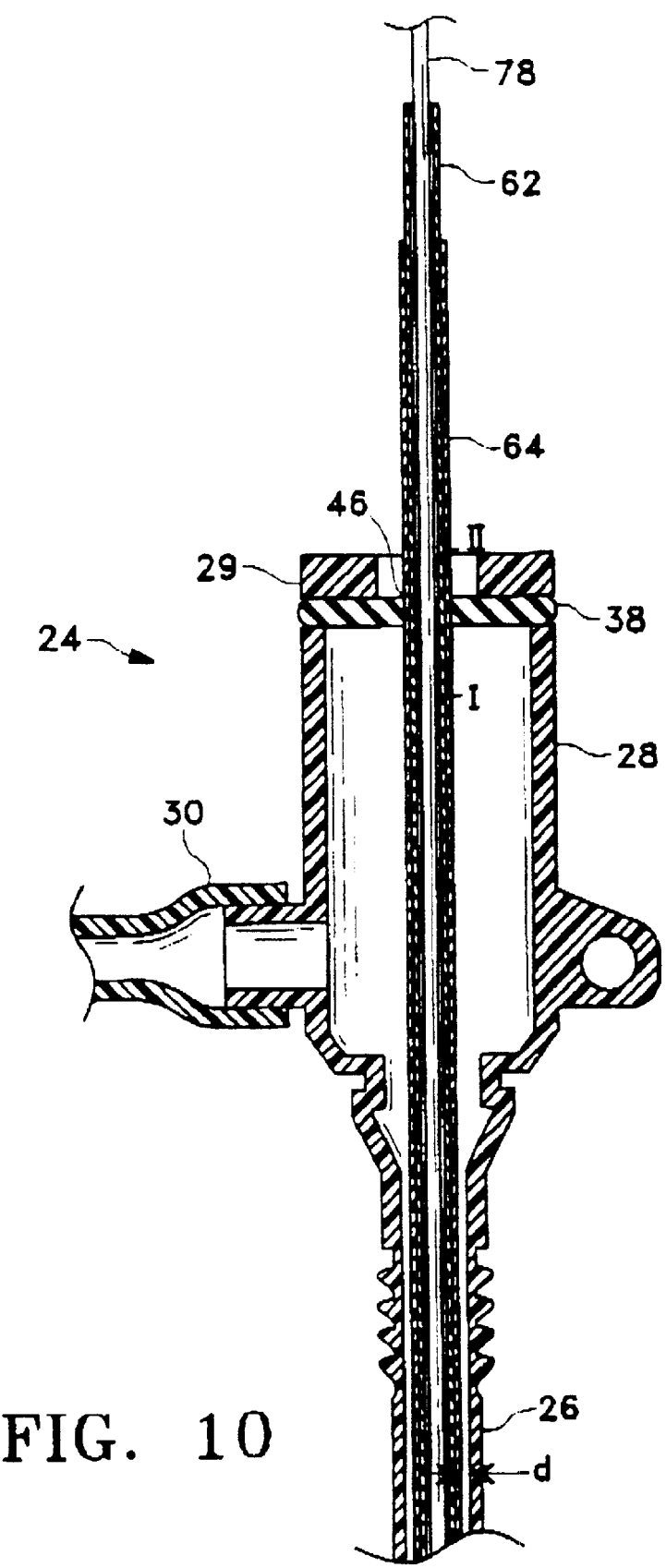
FIG. 10 is a cross-sectional view taken alone the line 10—10 of FIG. 9.

FIGS. 8–10 shows a second embodiment of the invention which is generally signified by the reference numeral 60. As with the previous embodiment, the puncture wound closure device of this embodiment includes a positioning device 4 and an implant delivery device 6.

In this embodiment, the positioning device 4 includes a sleeve 64 which is part of a depth sensing mechanism as will be explained later. The sleeve 64 comprises a distal end 70 and a proximal end 72.

The implant delivery device 6 of this embodiment includes an implant holder 62, and a plunger 78. The implant holder 62 having a distal end 66 and a proximal end 68. Similarly, the plunger 78 includes a distal end 80 and a proximal end 82. The plunger 78 in this embodiment is a solid piece of elongated rod with round-off ends 80 and 82. The plunger 78 is insertable into the holder 62 which in turn is insertable into the sleeve 64. Located at the distal end 66 of the implant holder 62 is a slit 74 which is present to facilitate entry of the implant 22 prior to use.

Figure 11:
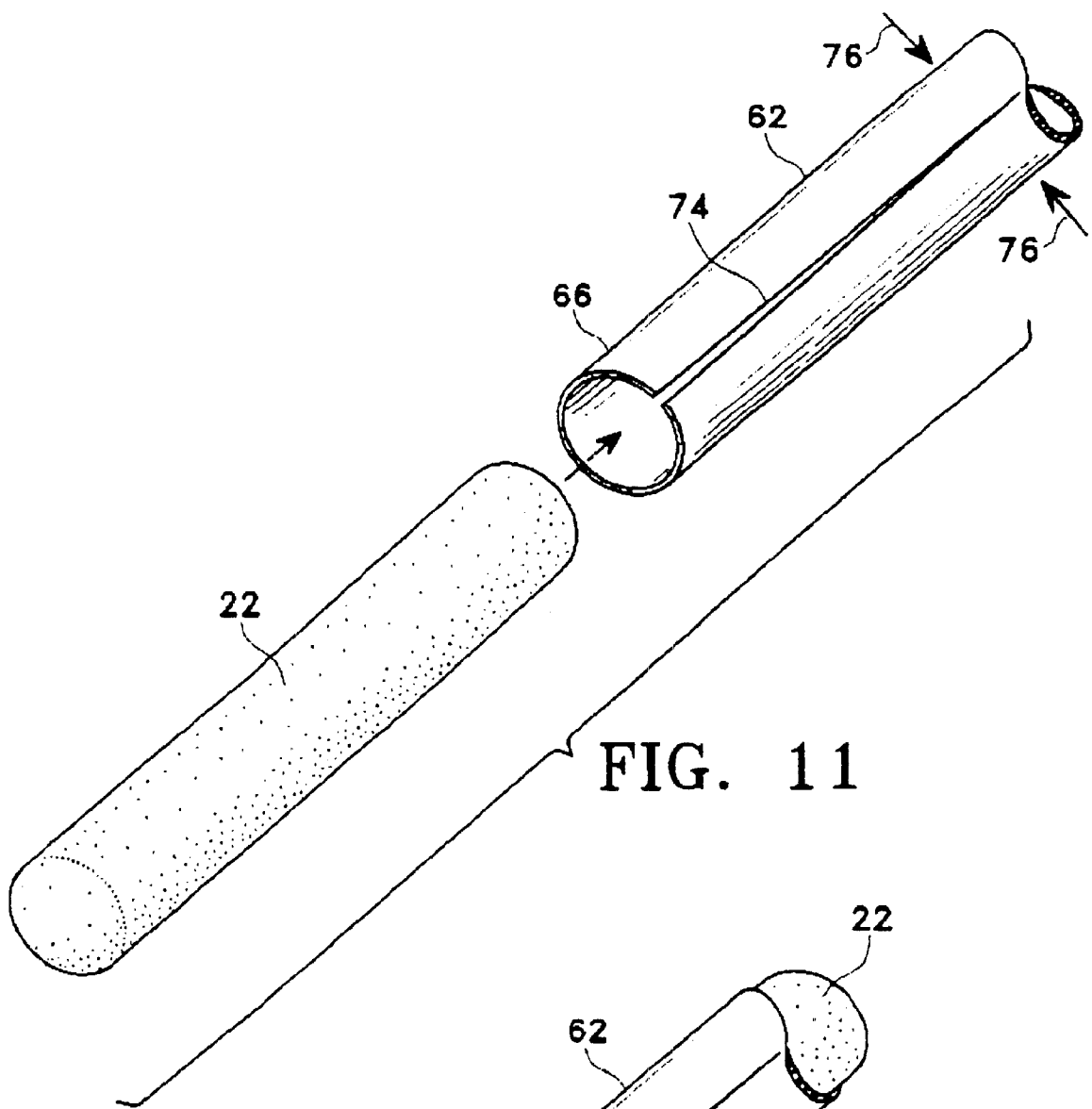
FIGS. 11 and 12 are sequential views showing the mounting of an implant in accordance with second embodiment of the invention prior to deployment.
Figure 12:
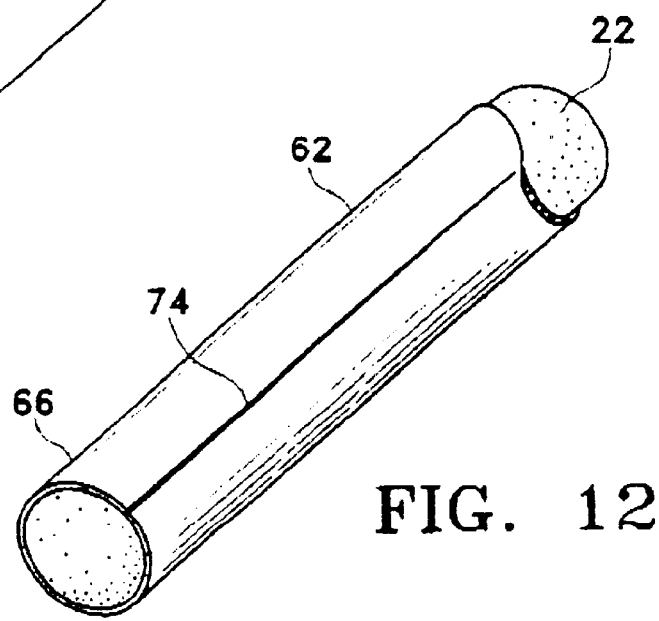

FIGS. 11 and 12 depict how the implant 22 can be inserted into the distal end 66 of the holder 62 expeditiously with the aid of the slit 74. The holder 62 is made of flexible material such as polyethylene. Prior to entry, digital pressure can be exerted in the directions 76 at a location on the holder 62 where the slit ends, for example, as shown in FIG. 11. As a consequence, the opening at the distal end 66 of the holder 62 enlarges allowing the implant 22 to be slid in easily. After entry, digital pressure is withdrawn, the implant 22 is confined by the holder 62 at the distal end 66 by the closing of the slit 74 and is as shown in FIG. 12.

Reference is now returned to FIG. 8. Near the proximal ends 72, 68 and 82 of the sleeve 64, holder 62 and plunger 78, respectively, is a plurality of markings 14, such as "III" and "IV" as shown in FIG. 8. The markings 14 are relied upon to approximately estimate the depths of the sleeve 64, holder 62 and plunger when inserted inside the tissue of the patient as hereinafter described.

Shown in FIG. 8 is also an introducer 24, which is substantially similar to the introducer used in the previous embodiment and is therefore not further elaborated in here.

FIG. 9 is a perspective view, which shows the arrangement of the different components of the second embodiment 60 with respect to the introducer 24. In FIG. 9, the introducer sheath 26 is illustrated as inserted into an artery 33 through the surface skin 34, the underlying tissue 36 and the artery wall 32. Inserted into the introducer sheath 26 is both the positioning device 4 and the implant delivery device 6.

FIG. 10 is a cross-sectional view taken along the line 10—10 of FIG. 9 that shows the introducer body 28 in cross-section. The internal structure of the introducer body 28 is substantially similar to the previous description and is thus not repeated. Shown in FIG. 10 is the sleeve 64, the implant holder 62 and the plunger 78 all as passing through the orifice 46 of the septum 38 located inside the introducer body 28.

In a similar manner with the previous embodiment, the positioning device 4 and the introducer sheath 26 maintain a predetermined separation. Specifically, in this embodiment, the outermost surface of the sleeve 64 and the inner wall of the introducer sheath 26 is spaced by a distance d as shown in FIG. 10. In this embodiment, the dimension of the separation d is 0.2 mm.

Furthermore, as shown in FIG. 9, attached to the side port outlet 30 of the introducer body 28 is a valve 40. The valve 40 is controlled by a turn knob 42. The valve 40 and the control knob 42 is part of a fluid monitoring section 43.

FIGS. 13A–13H in conjunction with FIGS. 8–10 illustrate the process of using the puncture wound sealing apparatus of this embodiment. After certain medical procedure, such as a PCTA, the introducer sheath 26 remains inserted in the patient's artery 33 through the surface skin 34, the subcutaneous tissue 36 and the artery wall 32, for example. Instead of removing the introducer 26 as practiced by most prior art counterparts, the present invention utilizes the introducer 26 in the puncture wound sealing process.

Figure 13A:
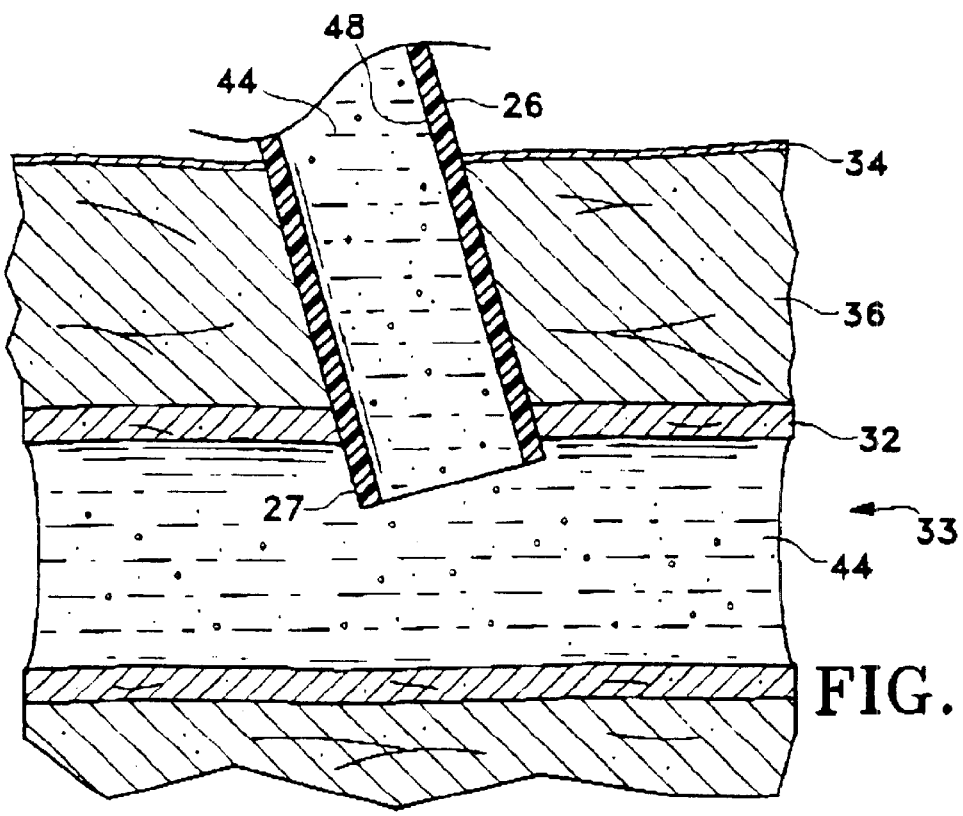
FIGS. 13A–13H are sequential views, shown in cross-section, the method of using the second embodiment of the invention.

As shown in FIG. 13A, the introducer sheath 26 remains seated in the artery 33 from the previous medical procedure. As described previously, the sheath 26 has a bore 48 and is filled with blood 44 which has no outlet because the orifice 46 of the septum 38 at the proximal end 29 of the introducer 24, without any object inserted in the introducer 24, is close (FIG. 10). Furthermore, the side valve 40 is also close with the turn knob 42 (FIG. 9) turned to the close position.

Reference is now directed back to FIG. 8. The implant 22 is inserted into the holder 62 through the distal end 74 having the slit 74 as described above. The plunger 78 is then inserted into the holder 62 through the proximal end 68. Thereafter, the holder 62 with the plunger 78 and the implant 22 inside, is inserted into the sleeve 64.

Figure 13B:
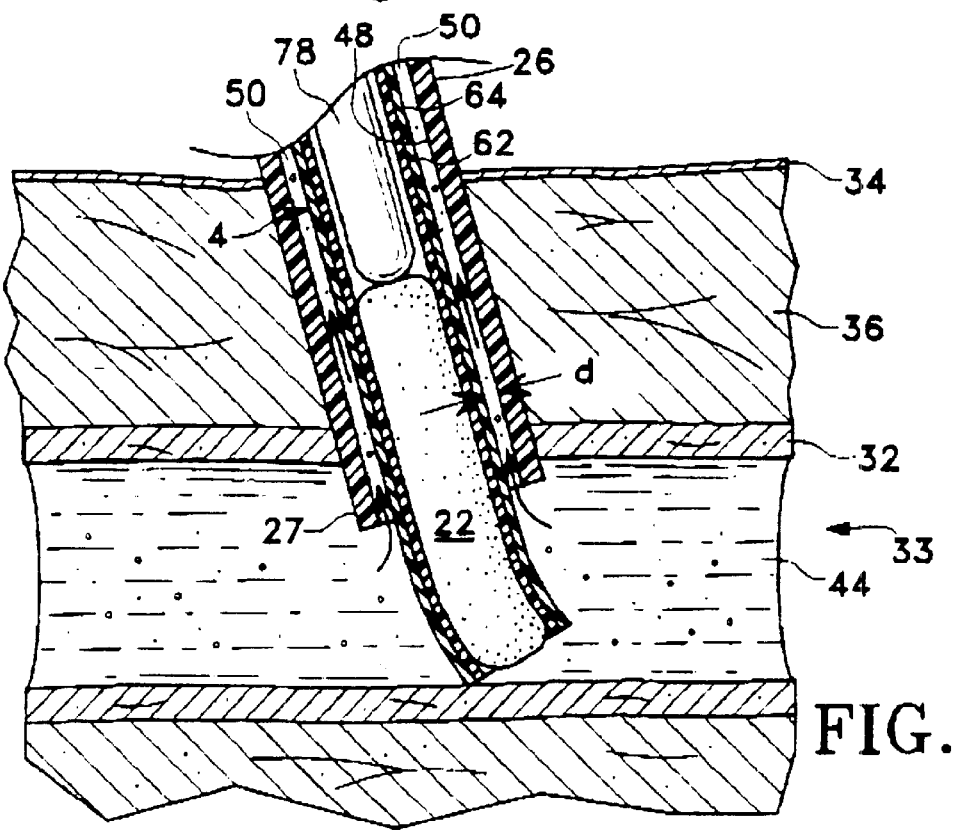

While the turn knob 42 remains turned to the closed position, the entire combination, that is, the sleeve 64 with the holder 62, the plunger 78 and the implant 22 is inserted into introducer sheath 26 through the septum 38 (FIG. 10) of the introducer body 28. The combination has to be inserted beyond the distal end 27 of the introducer sheath 26 as shown in FIG. 13B. To accomplish this task, the combination has to be inserted into the introducer 24 until the mark "II" is barely above the proximal end 29 of the introducer body 28, as shown in FIG. 10.

At this juncture, the valve 40 is intermittently turned on and off via the manipulation of the valve 42 for the purpose of sensing and determining the position of the introducer sheath 26 within the artery 32.

As mentioned before, the introducer sheath 26 has a bore 48 (FIGS. 13A and 13B). The cross-sectional dimension of the positioning device 4, the sleeve 64 in this case, is slightly smaller than the corresponding cross-sectional dimension of the sheath bore 48. Thus when the sleeve 64 is inserted into the introducer sheath 26 as shown in FIG. 13B, a volume of gap space 50 separates the sleeve 64 from the introducer sheath 26. The separation of the sleeve 64 to the sheath 26 is labeled d in FIG. 13B. With the introducer sheath 26 still inserted into the artery 33, blood 44 flows into the gap space 50. Thus, when the valve 40 is turned on via the knob 42, blood 44 can be seen flowing through the valve 40 (FIG. 9).

Figure 13C:
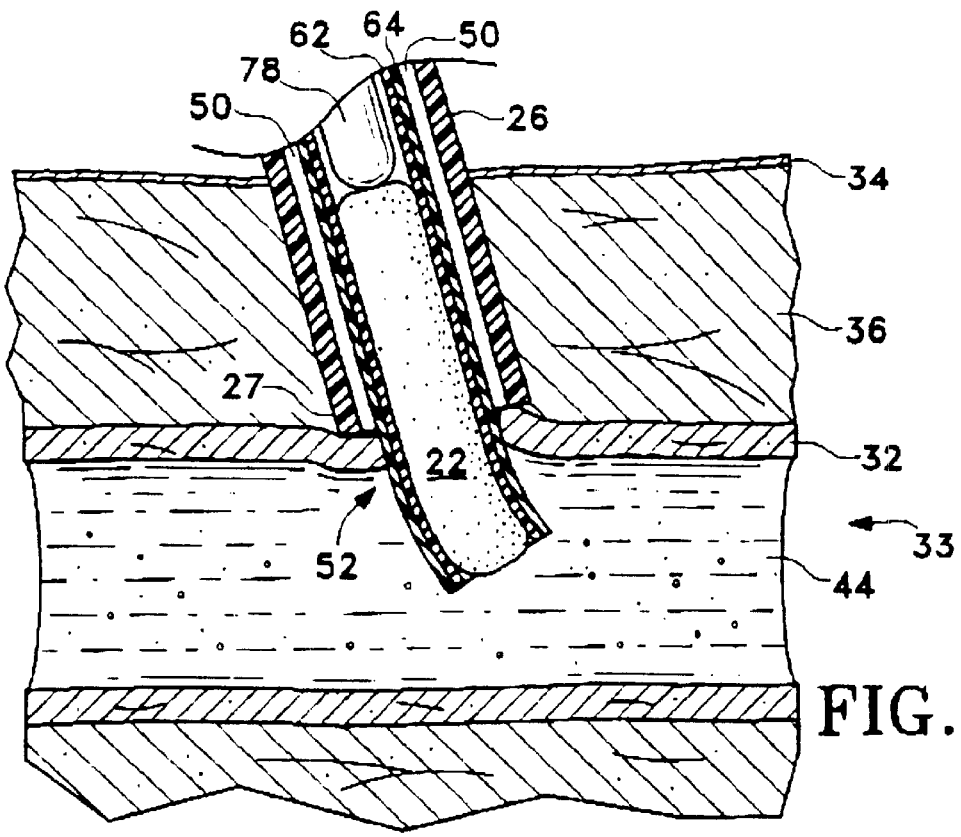

What follows is the simultaneous withdrawal of the sheath 26 and the combination that includes the sleeve 64, holder 62, plunger 78 and the implant 22. The withdrawal process should be slow and gradual. With the valve 40 (FIG. 9) turned on and with the introducer 24 gradually pulled away from the artery 33, there is a point in time in which the blood flow through the valve 40 suddenly ceases. The position of the introducer sheath 26 at this juncture is as shown in FIG. 13C. Specifically, the position of the distal end 27 of the sheath 26 is barely out of the artery 33 and is still in contact with the artery wall 32.

The reason for the cease of blood flow is because the introducer sheath 26 has been pulled out of the artery 33. The natural elasticity of the artery wall 32 at the puncture wound site 52 allows the puncture opening of the artery 33 to shrink and grip onto the sleeve 64. As such, blood is stopped from flowing into the gap space 50 resulting in the lack of blood flow even with the valve 40 turned on via the knob 42 (FIG. 9).

Figure 13D:
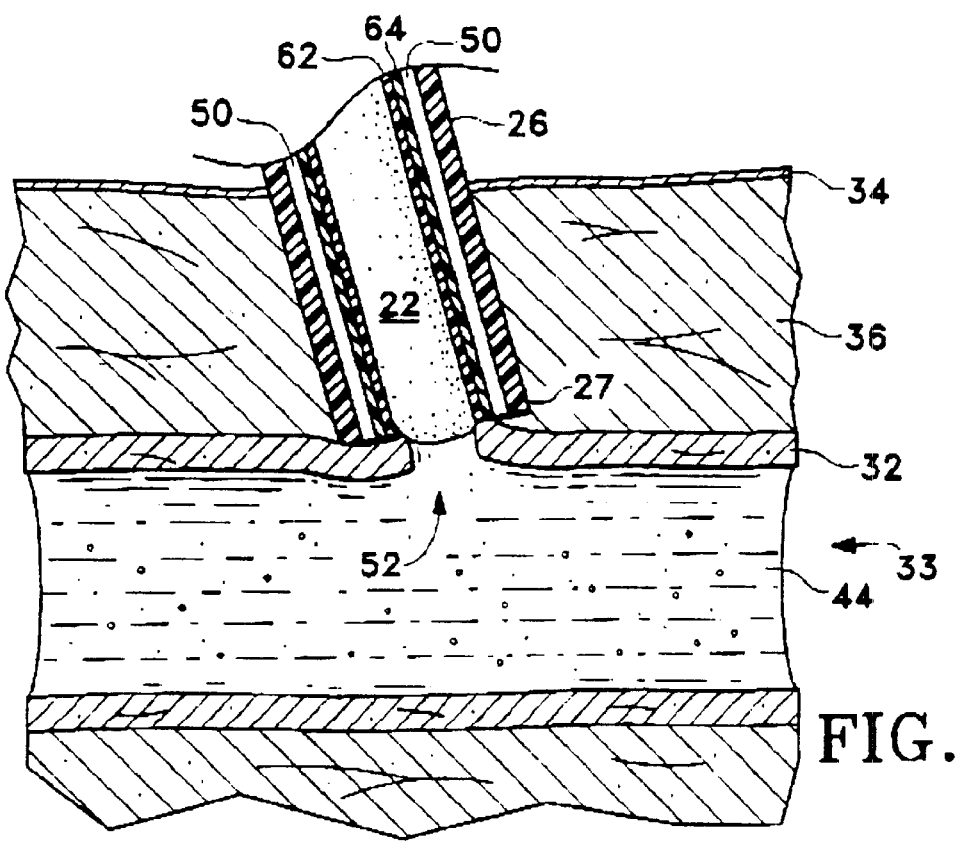

With the introducer sheath 26 held steady, the combination which includes the sleeve 64, the holder 62, and the implant 22 is slowly retracted away from the artery 32. The retraction should stop when the mark "I" on the sleeve 64 is barely above the distal end 29 of the introducer body 28 (FIG. 10). The position of the implant 22 carried by the holder 62 at the distal end 27 of the sheath 26 at this juncture is as shown in FIG. 13D.

Figure 13E:
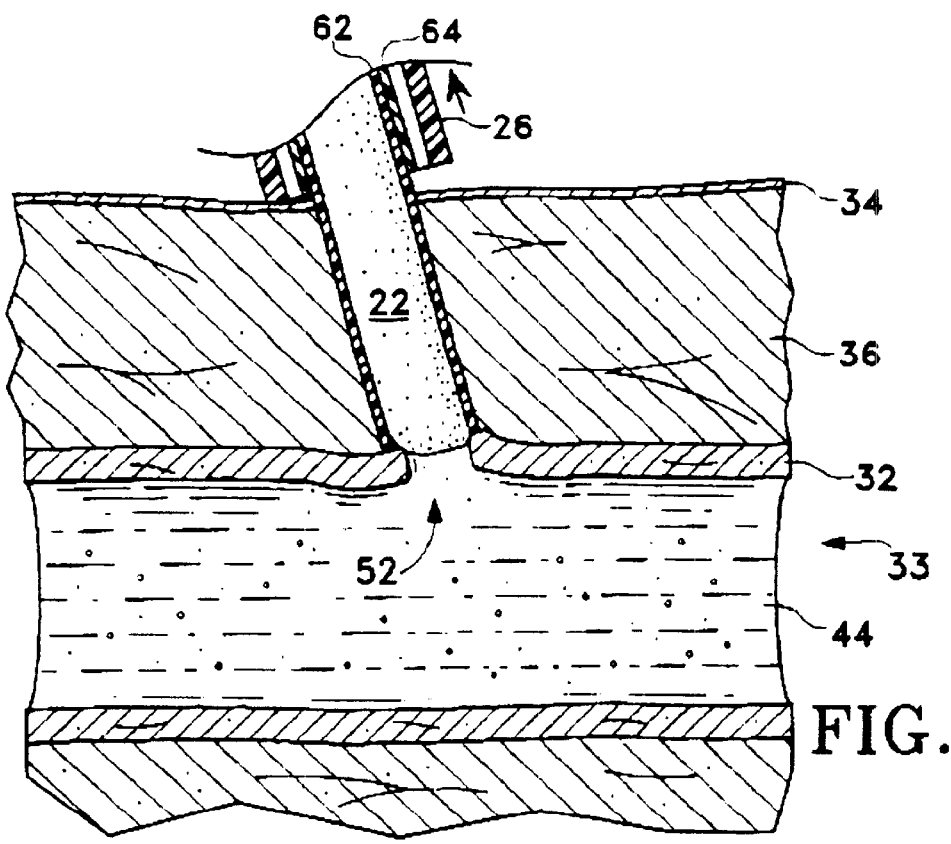

The blood monitoring valve 40 is then turned off. The next step is the complete withdrawal of the introducer sheath 26 and the sleeve 64. FIG. 13E shows the introducer sheath 26 and the sleeve 64 as in the process of withdrawing.

The following step is the deployment of the implant 22. First, the plunger 78 is held stationary. Then, the implant holder 62 is slipped from the plunger 78. After the complete withdrawal of the implant holder 62, the implant 22 is left in the tissue 36 at the puncture site 52 precisely above the puncture opening of the artery wall 32. As explained before, precise delivery of the implant 22 avoids many undesirable consequences such as hematoma and embolism.

Figure 13F:
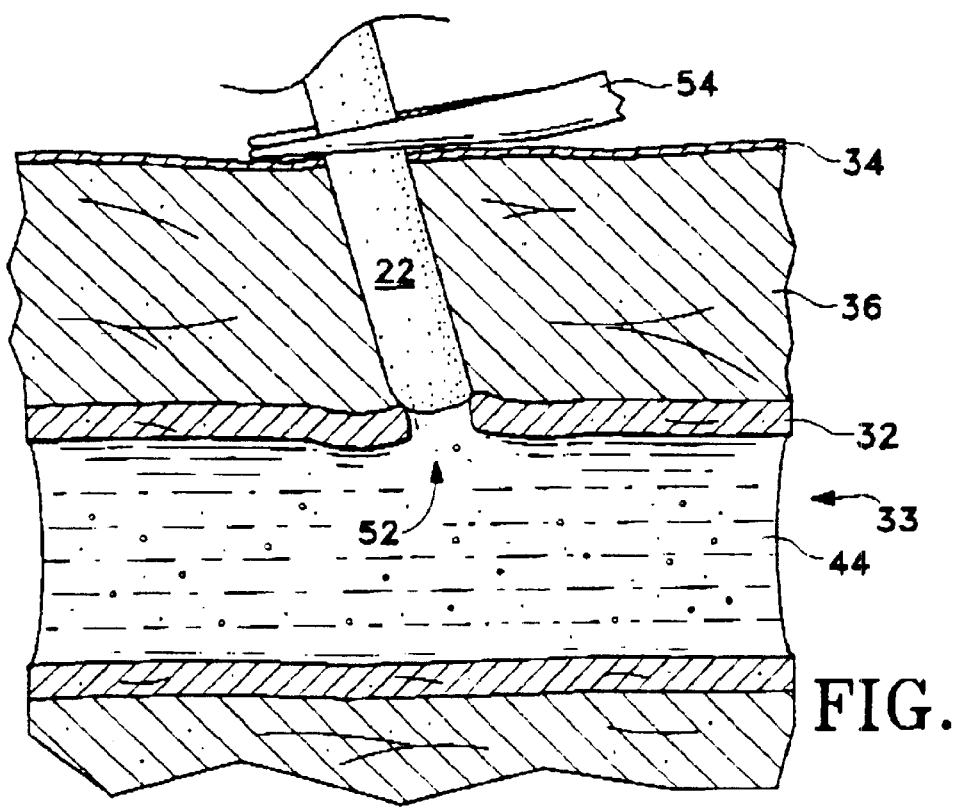
Figure 13G:
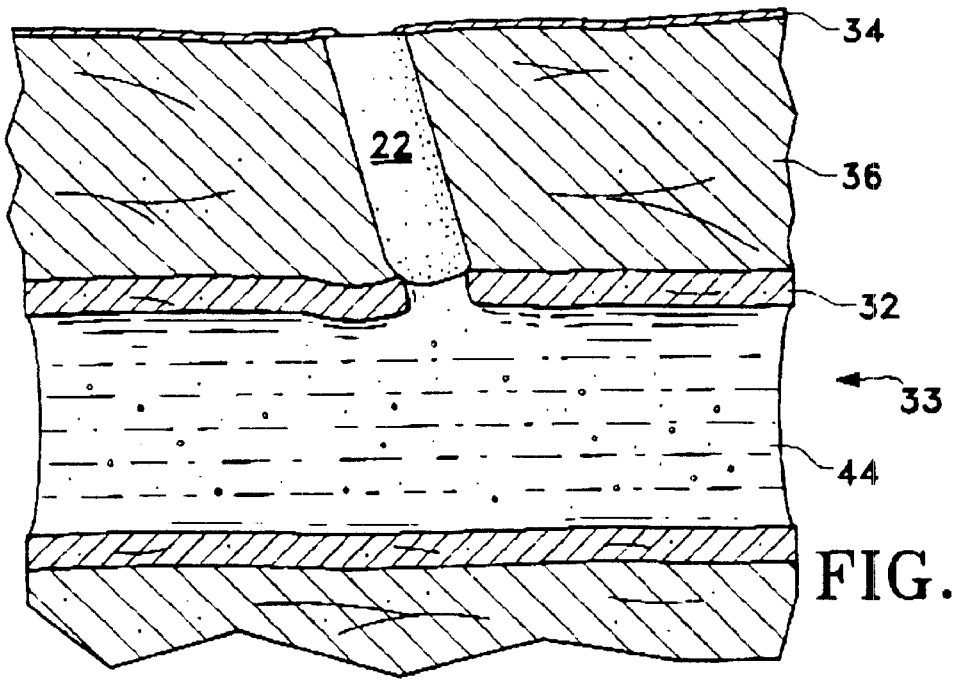

What follows is the trimming of the excess length of the implant 22 by a trimming tool 54, for example, as shown in FIG. 13F. The trimmed implant 22 left in the tissue 36 is as shown in FIG. 13G.

Figure 13H:
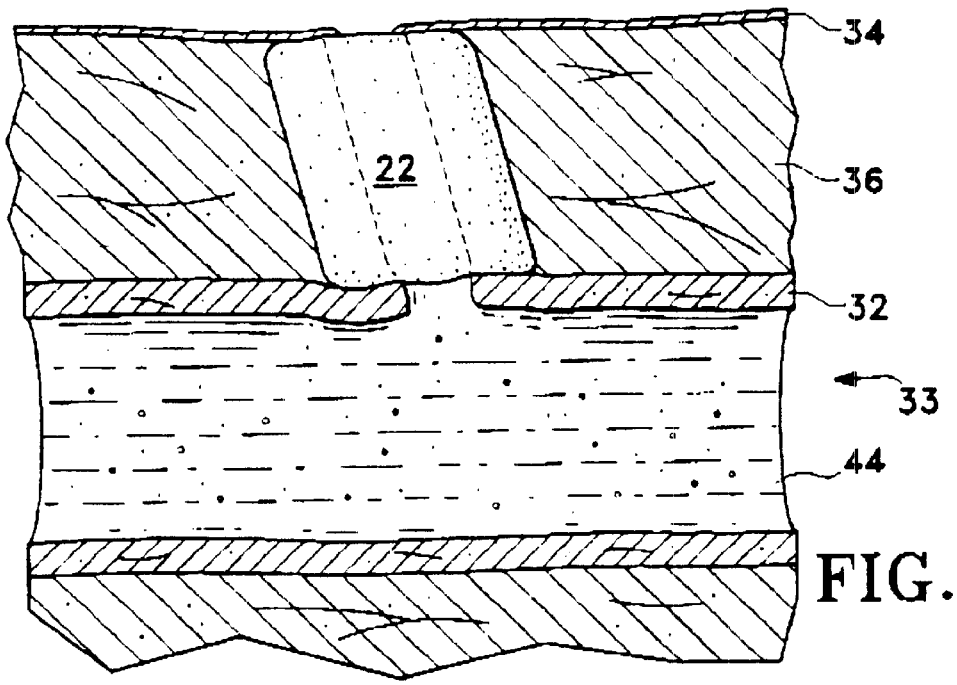

In a matter of minutes, preferably less than three minutes, the implant swells by itself to reach an equilibrium state in which it is no longer increasing in size. This results in a tight seal of the tissue 36 at the puncture wound site 52 as shown in FIG. 13H.

Figure 14:
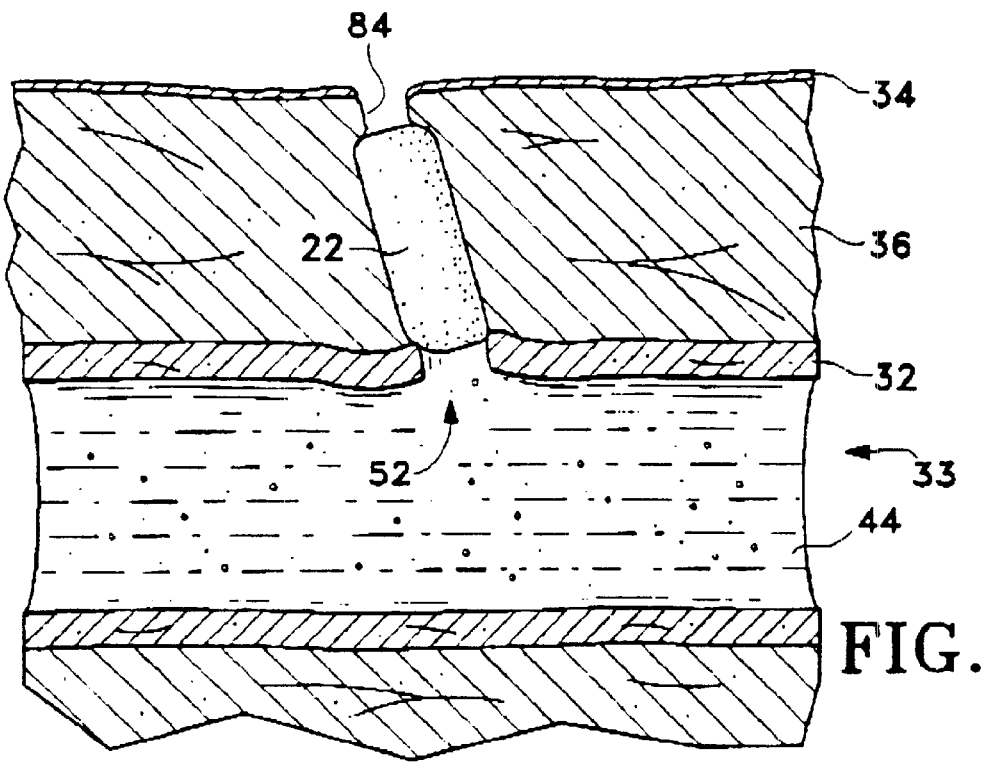
FIG. 14 is a cross-sectional view showing the tissue void above a short implant immediately after implant delivery process.
Figure 15:
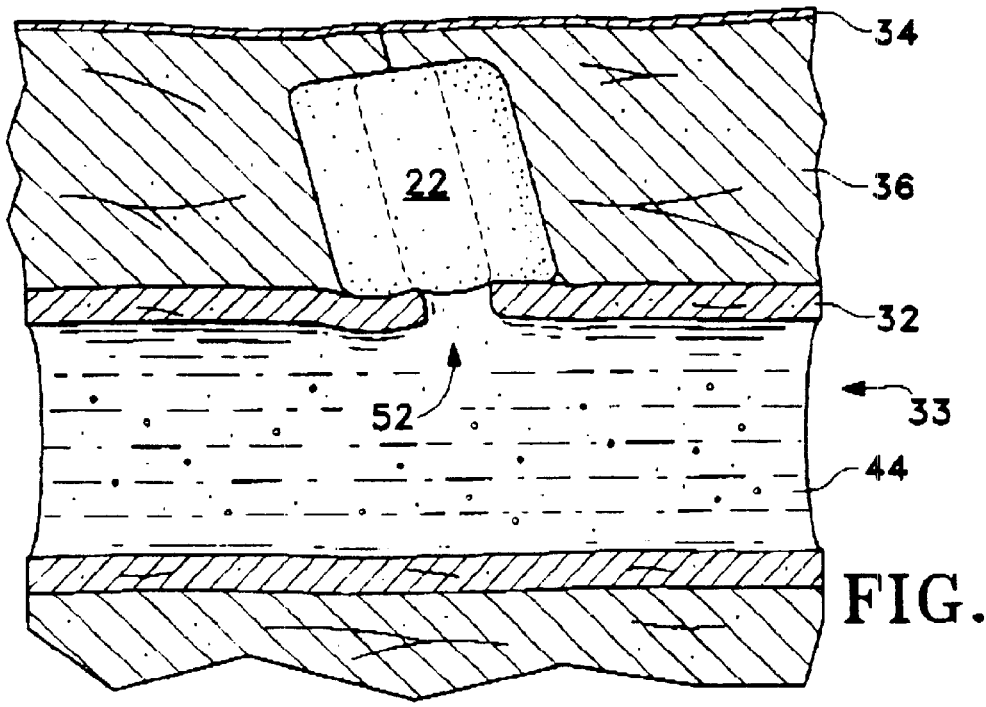
FIG. 15 is a cross-sectional view showing the closing of the tissue and the swelling of the implant after the implant delivery process.
Figure 16:
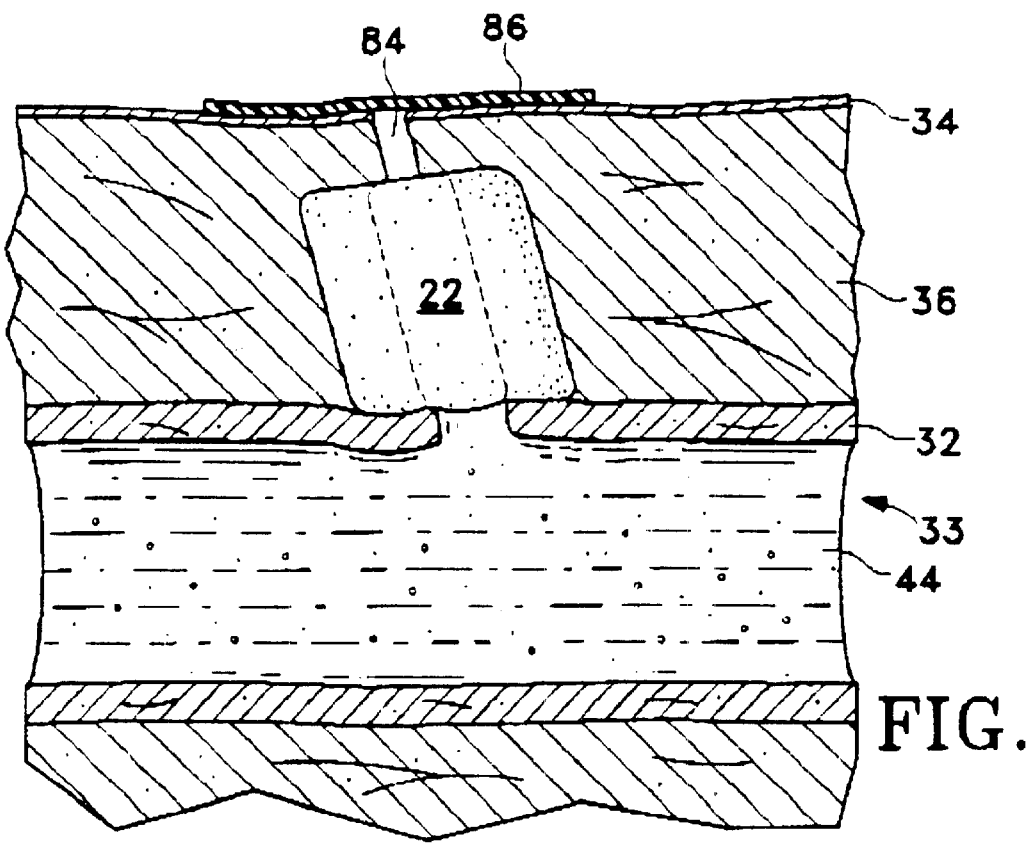
FIG. 16 is a cross-sectional view showing the use of a tape to close the void above a short implant which seals a puncture wound having a large surface area.

In an alternative embodiment, the trimming step as shown and described in FIG. 13F can be dispensed with. In this case, the implant length has to be shorter than the depth of the tissue 36 as shown in FIG. 14. After delivery of the implant 22, a void 84 is left over on the top of the implant 22 as shown in FIG. 14. If the dimension of the puncture wound site 52 is small, the natural elasticity of the tissue 36 closes by itself. After the implant 22 is swollen, the result is as shown in FIG. 15. However, if the dimension of the puncture wound site 52 is sufficiently large, a tape 86 may be needed to cover the void 84 as shown in FIG. 16.

Figure 17:
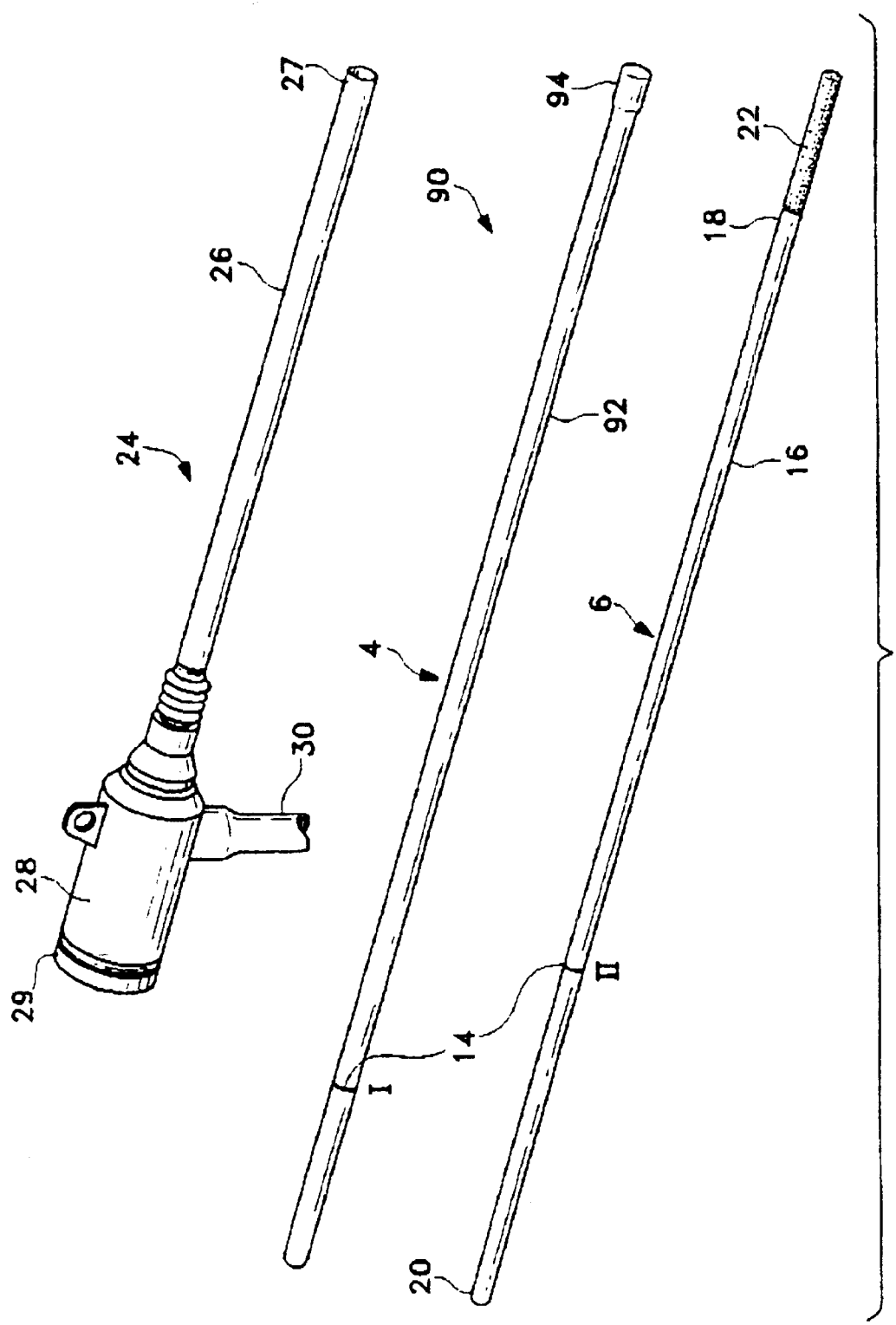
FIG. 17 is a perspective view of a third embodiment of the invention showing the various components.

FIG. 17 shows a third embodiment of the invention generally signified by the reference numeral 90. The configuration of this embodiment is somewhat similar to the first embodiment with the differences in the positioning device 4. In this embodiment, the positioning device 4 comprises a position guide 92 having an enlarged distal end 94. The position guide 92 having the enlarged distal end 94 constitutes part of a depth sensing mechanism as hereinafter described. This embodiment is ideal to be used on a patient with blood vessel walls having insufficient elasticity.

Figure 18A:
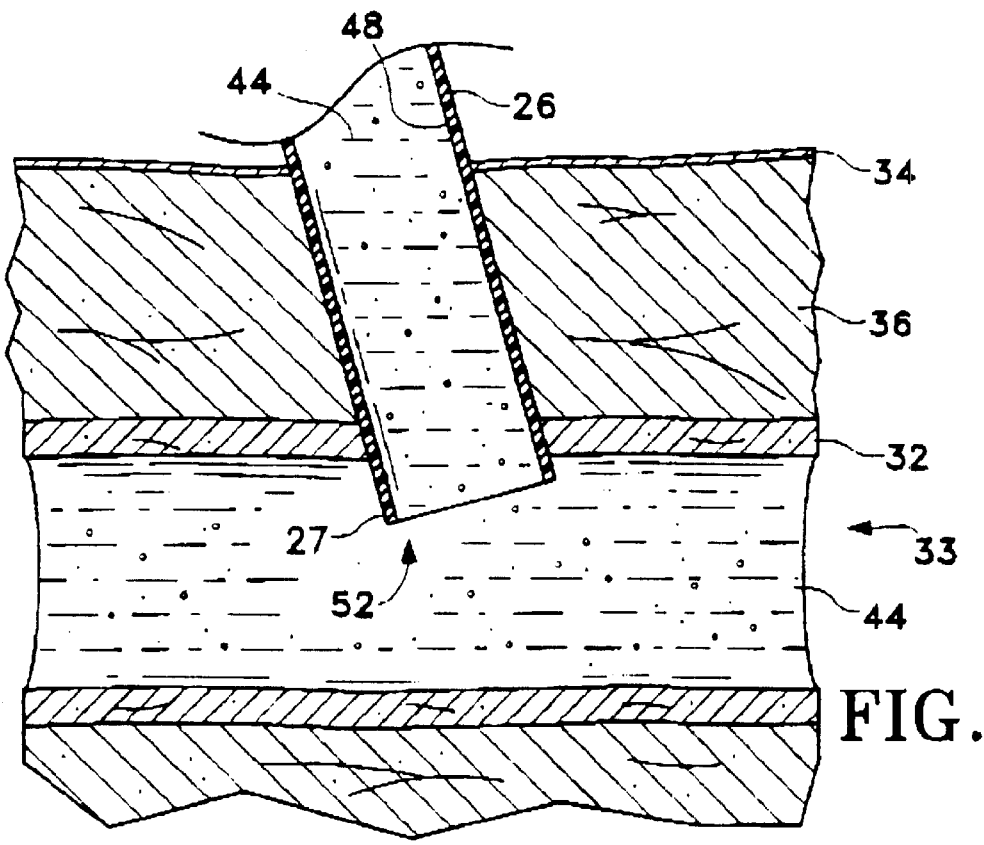
FIGS. 18A–18E are sequential views, shown in cross-section, the method of using the third embodiment of the invention.

FIGS. 18A–18 in conjunction with FIG. 17 illustrated the method of using this embodiment of this invention.

As described before, after certain medical procedures, the introducer sheath 26 remains seated in the tissue 36 at the puncture wound site 52 as shown in FIG. 18A.

Figure 18B:
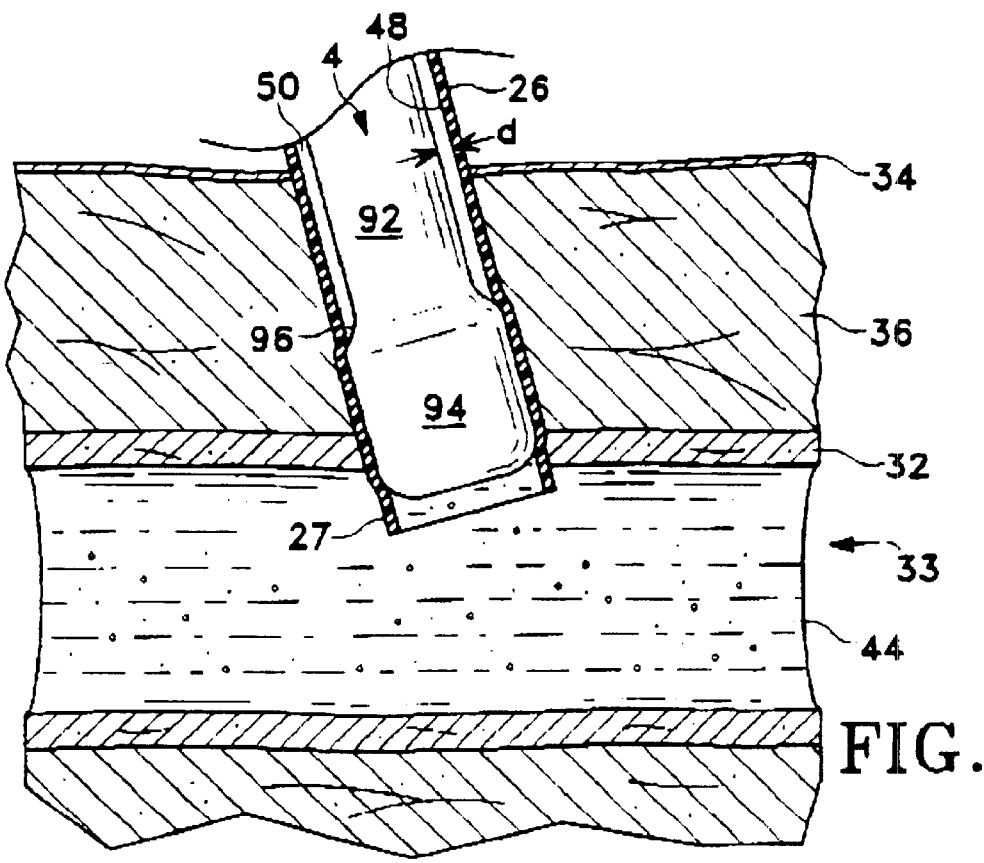

The positioning device 4, the position guide 92 with an enlarged distal end 94 in this case, is inserted into the introducer sheath 26, as shown in FIG. 18B.

As with the previous embodiments, the cross-sectional dimension of the bore 48 of the introducer sheath 26 is slightly larger than the corresponding cross-sectional dimension of the position guide 92. As shown in FIG. 18B, the position guide 92 is spaced from the bore 48 by a separation d. The value of d in this embodiment is 0.2 mm. However, the cross-sectional dimension of the enlarged distal end 94 is equal to the corresponding cross-sectional dimension of an expander (not shown) which is used to place the introducer sheath 26 prior to the PCTA procedure, for instance. Depending on the material that the sheath 26 is made of, the introducer sheath 26 may bulge out slightly when the enlarged distal end 94 is slid into the bore 48. In any event, the cross-sectional dimension of the enlarged distal end 48 is substantially equal to the corresponding cross-sectional dimension of the bore 48 such that the distal end 94, when inserted into the bore 48, is sealingly fit into the bore 48. The body of the position guide 92 is joined to the enlarged distal end 94 by a step section 96 as shown in FIGS. 18B–18E.

Figure 18C:
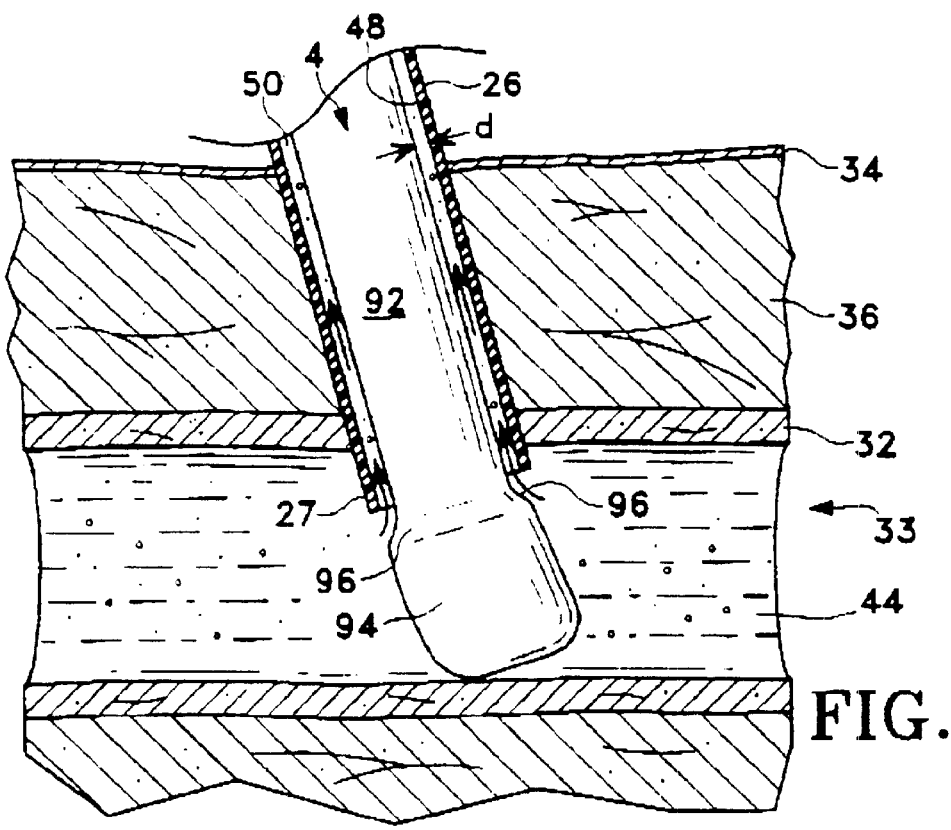

Reference is now directed to FIG. 18B. Because the enlarged distal end 94 is tightly fit into the bore 48, there is no blood flow in the gap space 50 when the enlarged end 94 is inside the bore 48. Then the position guide 92 continues to be slowly pushed toward the artery 33. When the enlarged end 94 exists the distal end 27 of the introducer sheath 26, bloods immediately flows over the enlarged distal end 94 through space between the step section 96 and the distal end 27 of the sheath 26 into the gap space 50, as shown in FIG. 18C.

Figure 18D:
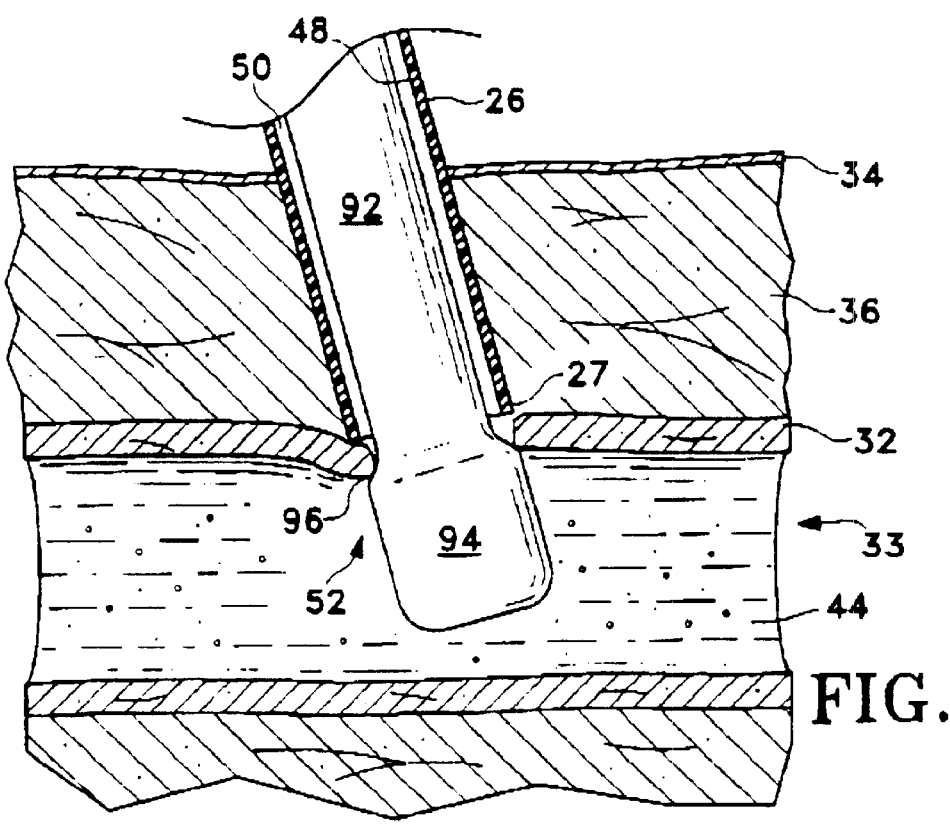

At this juncture, the introducer sheath 26 and the position guide 92 are slowly and simultaneously withdrawn together away from the artery 33. During the withdrawal process, there is a point in time in which the blood flow in the gap space 50 suddenly reduces substantially. For a patient with insufficient elasticity of the artery wall 32, the artery wall 32 may not be capable of gripping onto the position guide 92 as previously described. However, the position guide 92 with the enlarged distal end 94 compensates for the lack of elasticity of the vessel wall 32 in this embodiment. Specifically, during the simultaneous withdrawal of the sheath 26 and the positioning device 4, at some point in time, the opening of the vessel wall 32 intercepts the enlarged distal end 94 at the step junction 96. As a consequence, blood flow in the gap space 50 suddenly ceases. The cease of blood flow provides feedback to the operator (not shown) that the introducer sheath 26 is properly positioned atop the puncture opening of the vessel wall 32 at the wound site 52, as shown in FIG. 18D. The accurate positioning of the introducer sheath 26 at the puncture wound site 52 is a prelude for subsequent implant placement.

Figure 18E:
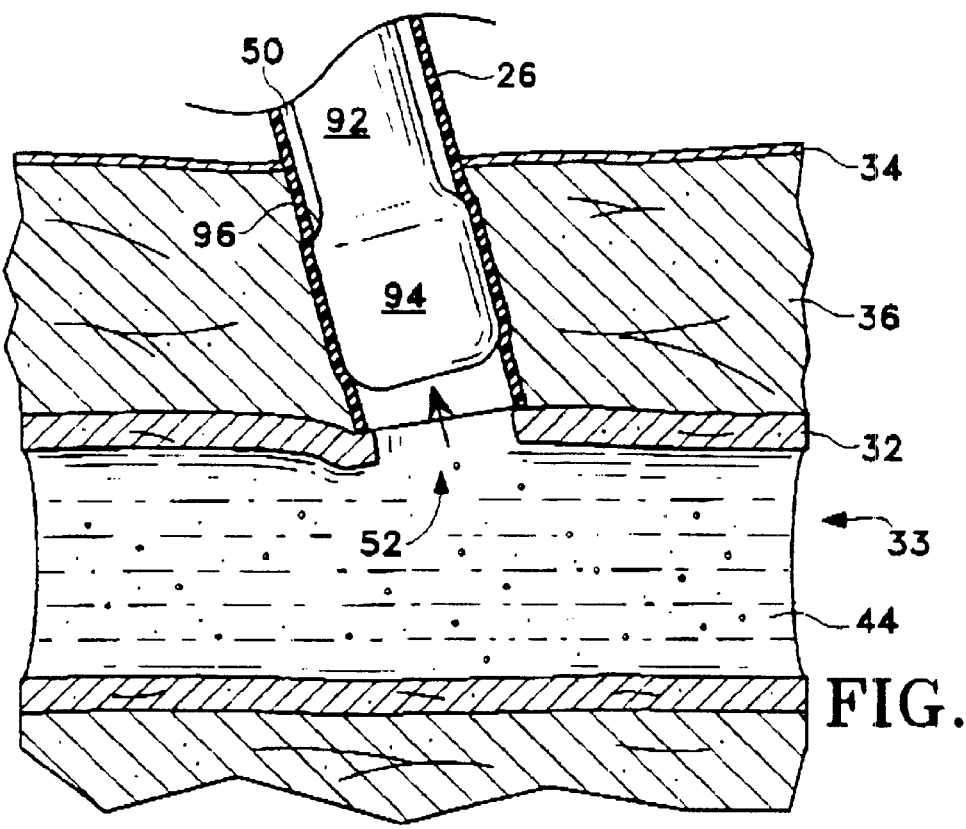

Thereafter, the sheath 26 is kept stationary and the position guide 92 is withdrawn relative to the introducer sheath 26, as shown in FIG. 18E.

The implant delivery step is similar to that as described in the first embodiment. For the sake of clarity and conciseness, the implant delivery step is not further repeated.

Figure 19:
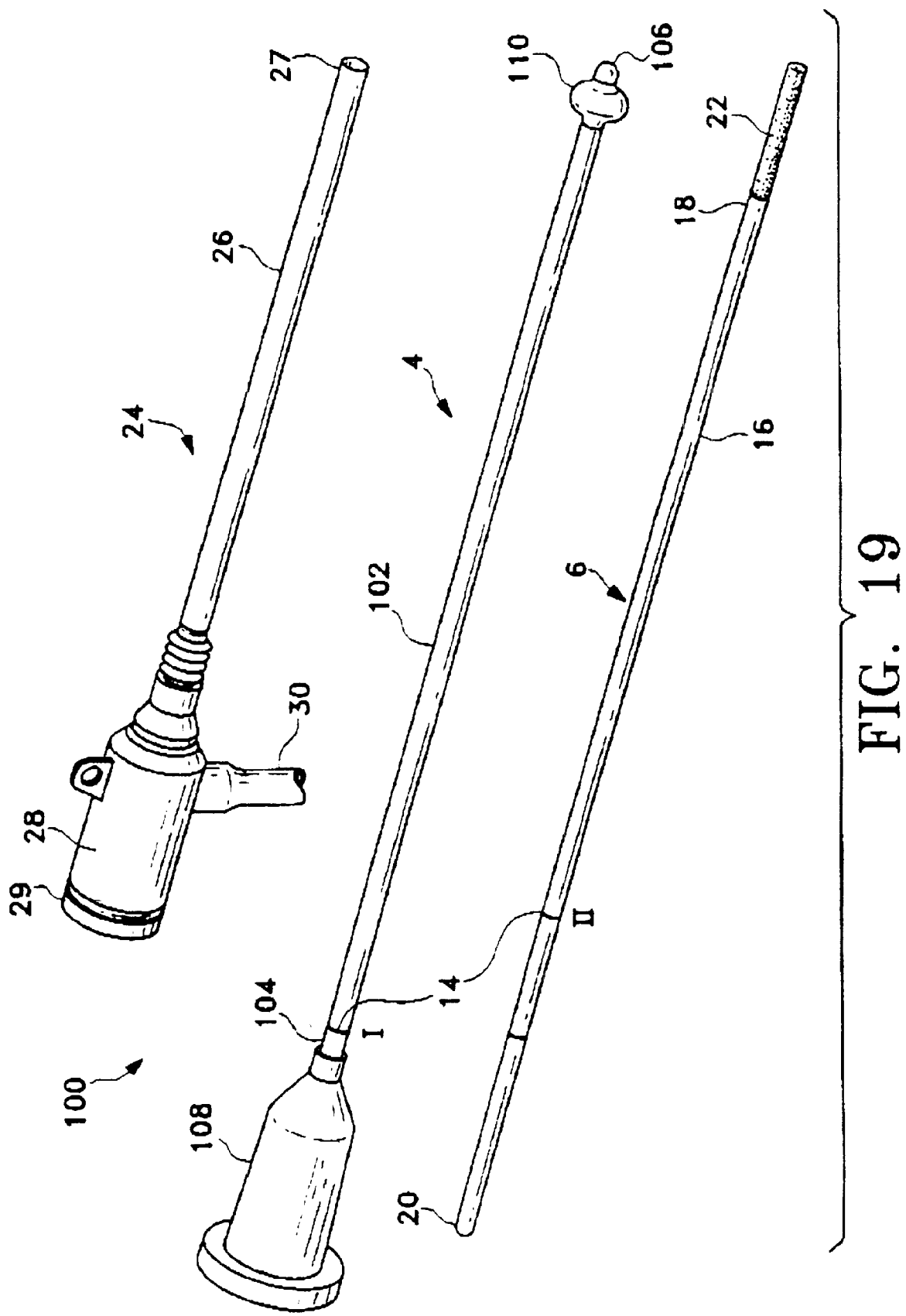
FIG. 19 is a perspective view of a fourth embodiment of the invention showing the various components.

FIG. 19 shows a fourth embodiment of the invention generally designated by the reference numeral 100. The positioning device 4 in this embodiment comprises an elongated tubular member 102 having a proximal end 104 and a distal end 106. Attached to the proximal and distal ends 104 and 106, respectively, are a fluid port 108 and a balloon 1 10. The tubular member 102 is designed to be in fluid communication with the fluid port 108 and the balloon 110 which is shown as inflated in FIG. 19. The tubular member 102 in cooperation with the balloon 110 act as part of a depth sensing mechanism which will be described later.

Figure 20A:
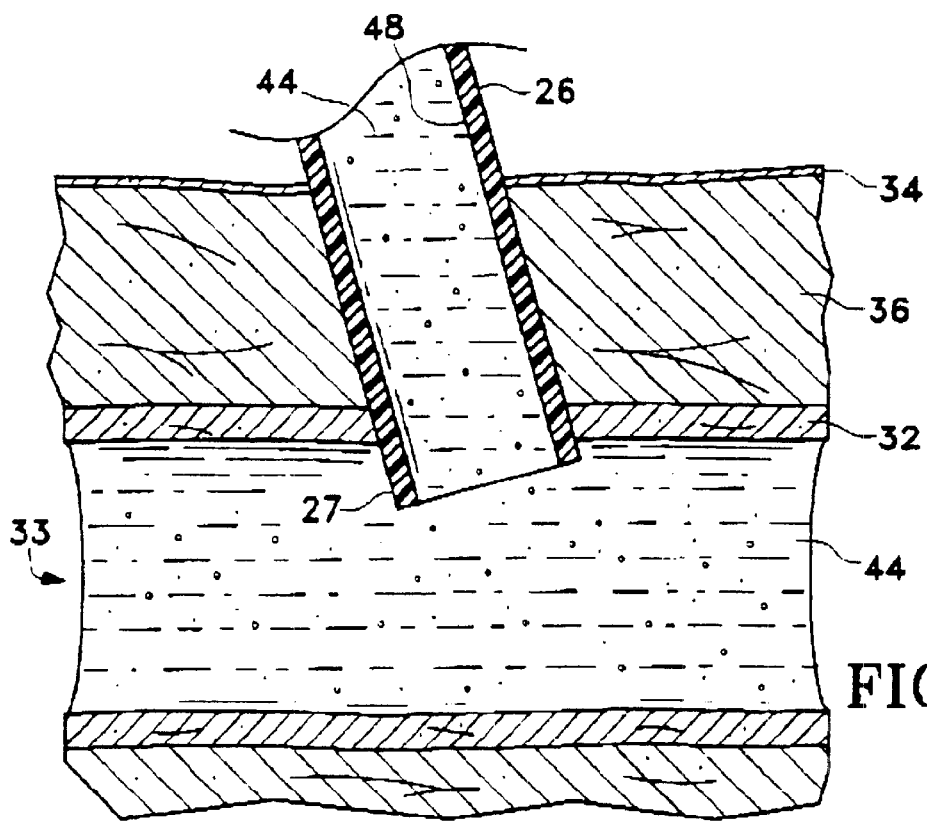
FIGS. 20A–20I are sequential views, shown in cross-section, the method of using the fourth embodiment of the invention.

FIGS. 20A–20I in conjunction with FIG. 19 illustrate the process of using the puncture wound sealing apparatus of this embodiment. After a PTCA procedure, for instance, the introducer sheath 26 remains inserted in the patient's artery 33 through the surface skin 34, the subcutaneous tissue 36, and the artery wall 32, as shown in FIG. 20A. Instead of removing the introducer 26 as practiced by most prior art counterparts, the present invention utilizes the introducer 26 in the puncture wound sealing process, thereby eliminating considerable intermediate steps and preventing unnecessary bleeding of the patient.

Figure 20B:
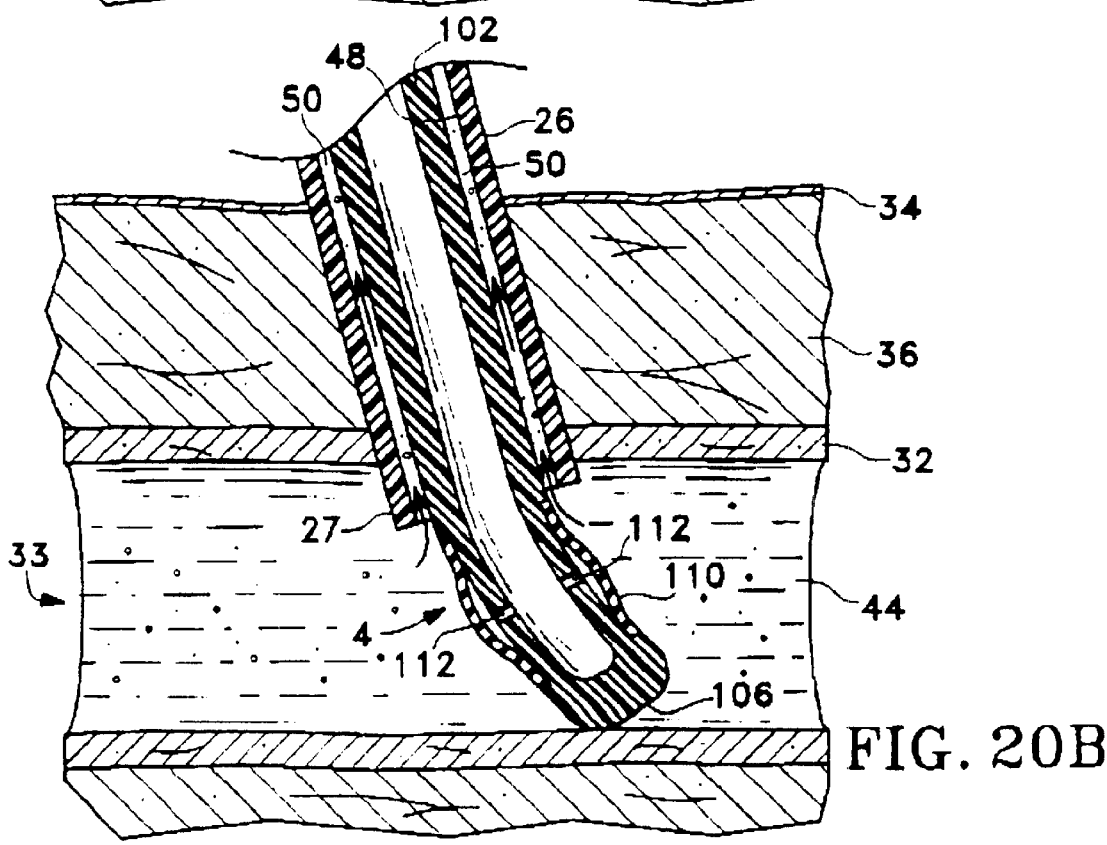

The positioning device 4, the tubular member 102 with the distal end 106 attached to a balloon 110 in this case, is inserted into the introducer sheath 26, as shown in FIG. 20B. The positioning device 4 in this embodiment is characterized by a storage mode and an extended mode. In this embodiment, the storage mode and the extended mode correspond to the balloon 110 at its deflated state and inflated state, respectively. With the balloon deflated, the positioning device 4 is inserted into the sheath 26 as shown in FIG. 20B. The initial depth of insertion of the positioning device 4 with respect to the sheath 6 can be approximately estimated by reading the marking 14 (FIG. 19) at the proximal end 104 of the tubular member 102 with respect to the distal end 29 (FIG. 3) of the introducer 28 in a substantially similar manner as previously described.

Shown in FIG. 20B is the cross-sectional dimension of the bore 48 of the introducer sheath 26 as slightly larger than the corresponding cross-sectional dimension of the tubular member 102. In this embodiment, this requirement is not necessary but it is helpful in several aspects. First, the tubular member 106 with a small cross-sectional dimension facilitates ingress and egress of the positioning device 4 through the sheath 26. Second, the gap space 50 formed as previously described is also helpful in confirming the position of the introducer sheath 26 with respect to the artery 33 as will be explained later.

Figure 20C:
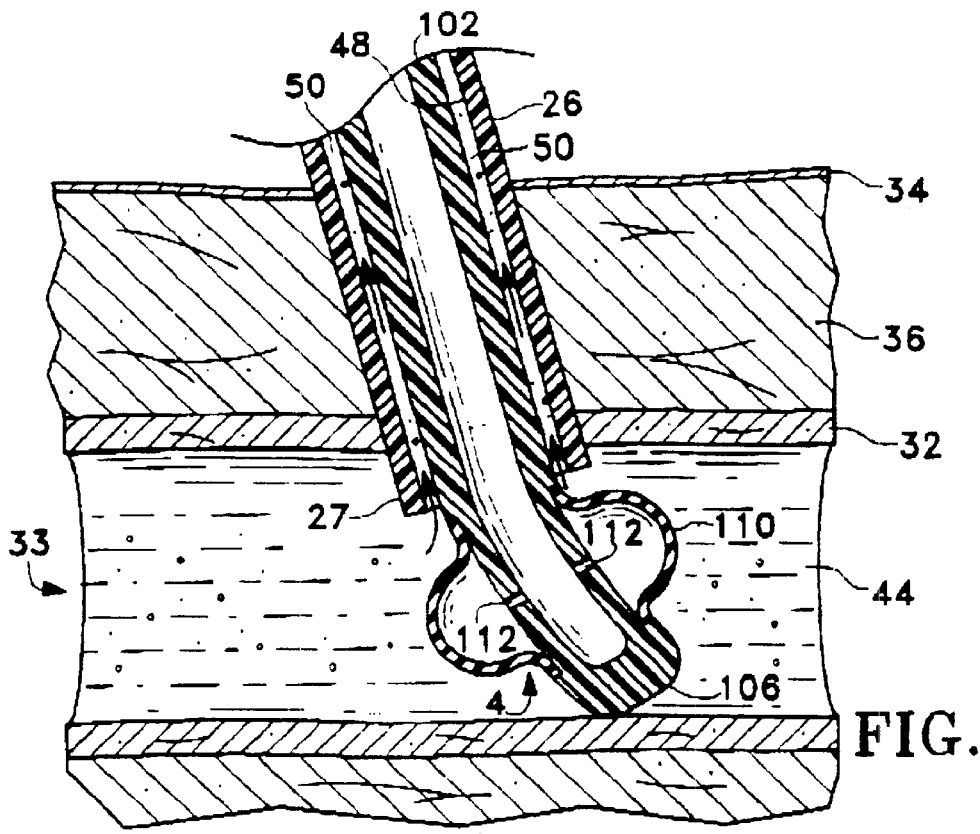

Next, the balloon 110 is injected with a fluid, air in this embodiment, through the fluid port 108 (FIG. 19). The injected fluid passes through the passageways 112 located adjacent to the distal end 106 of the tubular member 102. The balloon 110 after inflation is as shown in FIG. 20C.

Figure 20D:
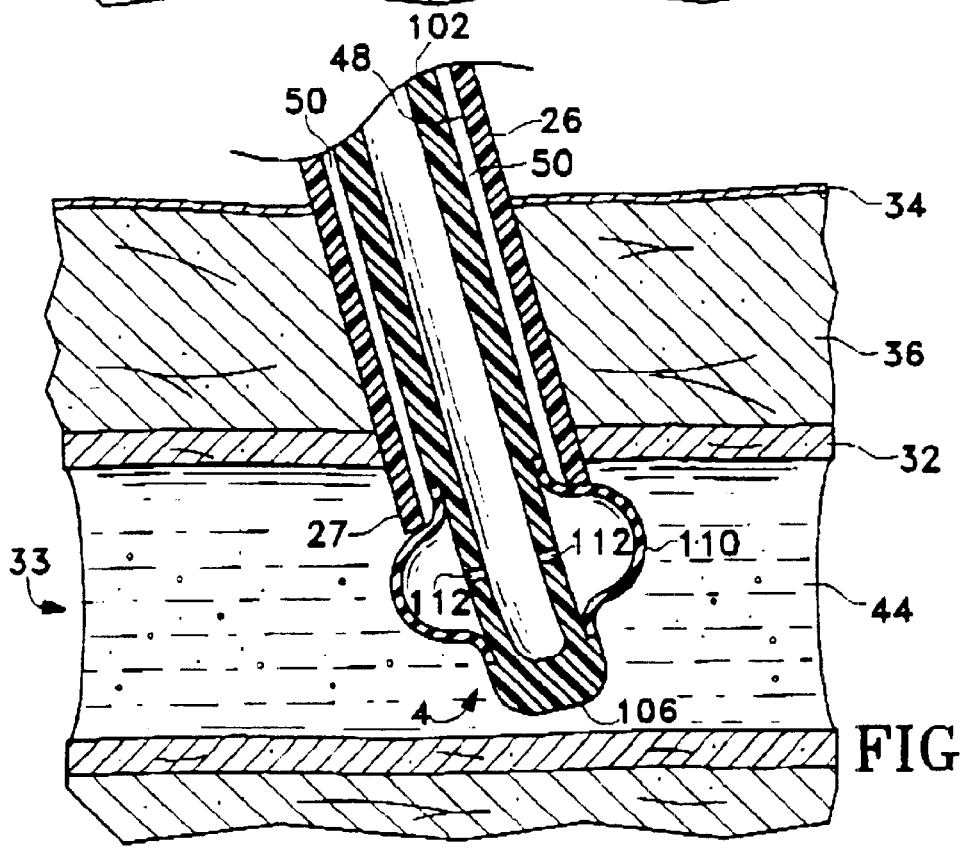

With the sheath member 26 held reasonably stationary, the tubular member 102 carrying the inflated balloon 110 is gradually retracted away from the artery 33. During the retracting process, the operator (not shown) at the distal end 104 (FIG. 19) of the tubular member should feel a slight resistance when the balloon 110 is stopped by the distal end 27 of the introducer sheath 26 as shown in FIG. 20D. As a further confirmation, the blood 44 in the gap space 50 can be monitored. When the inflated balloon 110 is in contact with the distal end 27 of the introducer sheath 26, blood flow in the gap space 50 suddenly stops. As mentioned before, the monitoring of blood flow in the gap space 50 as feedback for confirmation is helpful but is not essential.

Figure 20E:
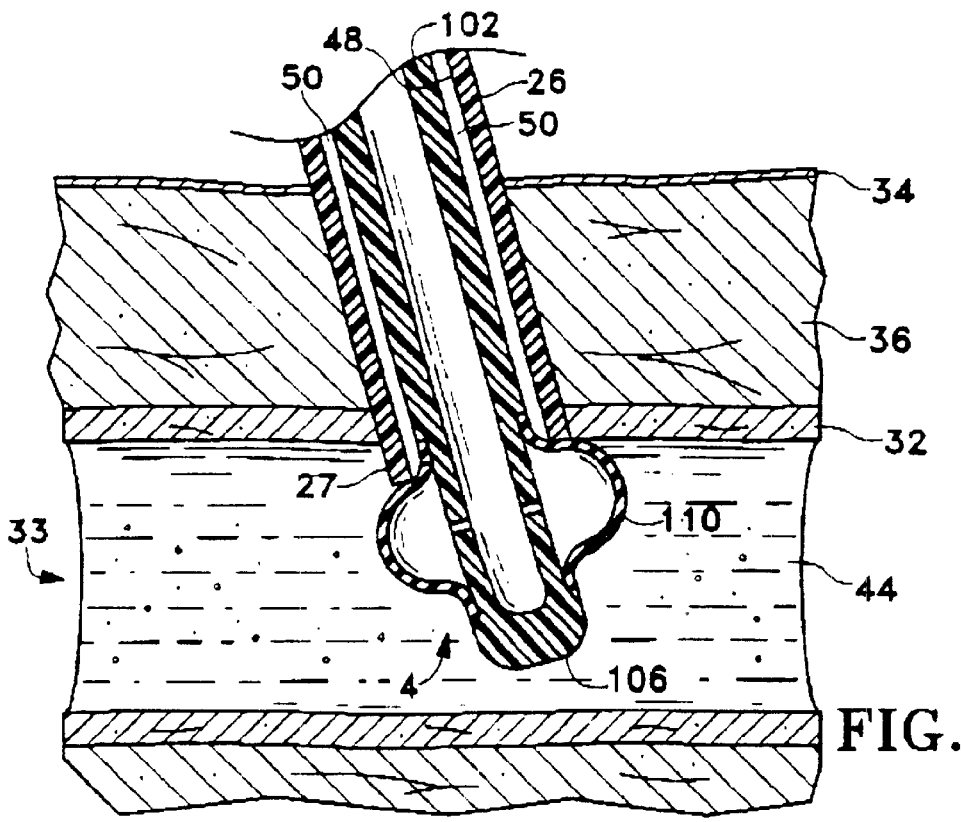

The positioning device 4 along with the introducer sheath 26 are then slowly retracted away from the artery 33 simultaneously. Again, during the retracting process, the operator (not shown) should feel a slight resistance when the balloon 110 gently collides with the artery wall 32 as shown in FIG. 20E. In this embodiment, the resistance forces felt by the operator (not shown) at various steps serve as feedback to the operator (not shown) in fathoming the position of the introducer sheath 26 with respect to the artery 33.

Figure 20F:
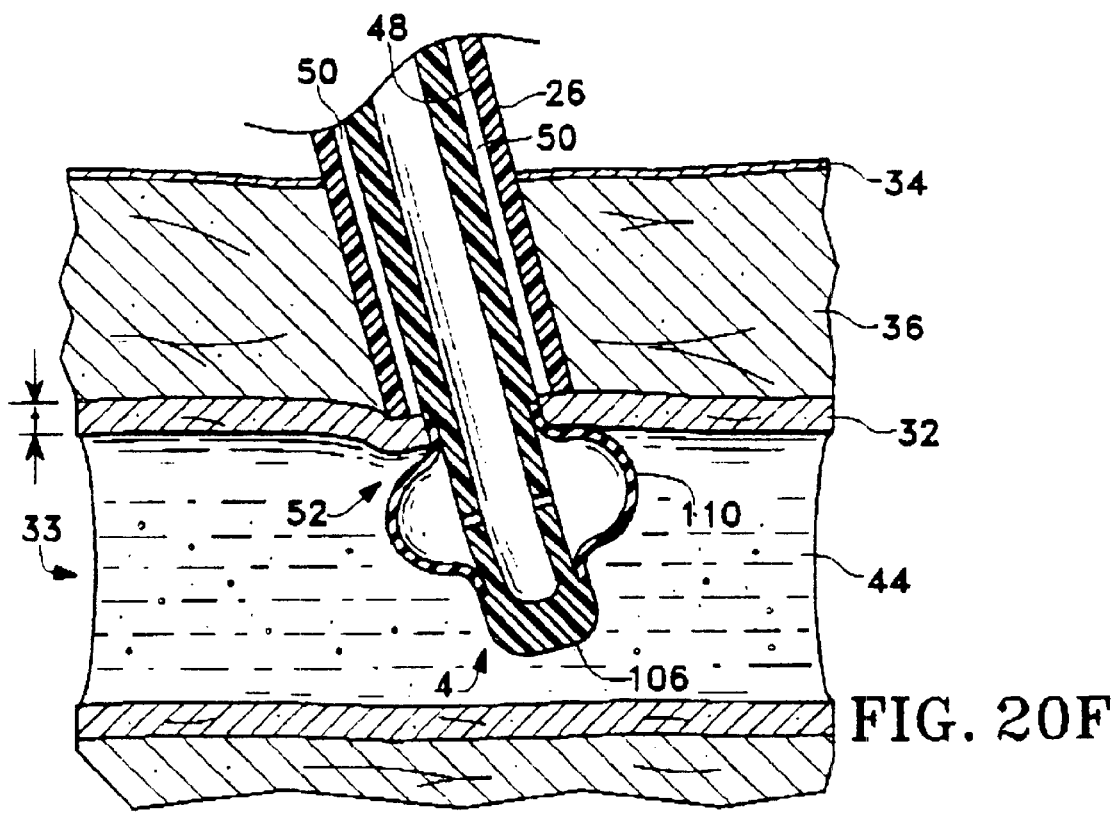

Thereafter, keeping the positioning device 4 stationary, the introducer sheath 26 is withdrawn further by a short distance t relative to the positioning device 4 as shown in FIG. 20F. In this case, t is the thickness of the artery wall 32 and is approximately 2 mm. Also shown in FIG. 20F is the opening of the artery wall 32 at the wound site 52 gripping onto the positioning device 4.

Figure 20G:
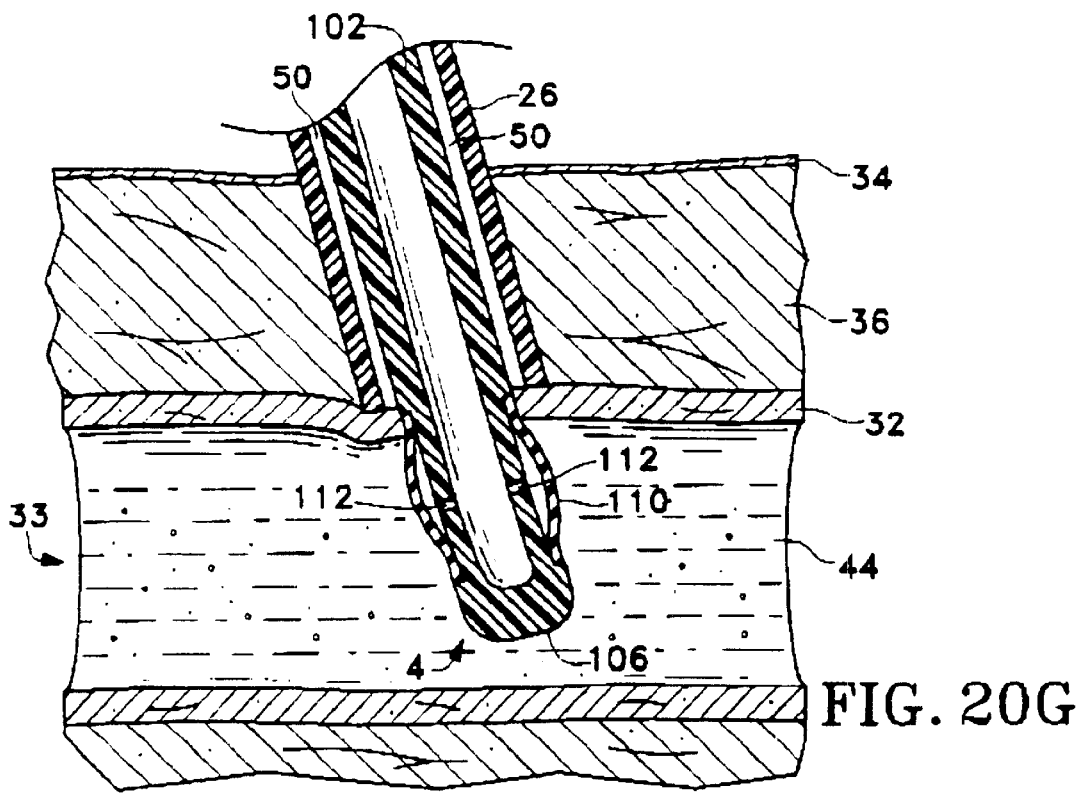

The balloon 110 is then deflated by exhausting the fluid, air in this case, through the fluid port 108 via the passageways 112 as shown in FIG. 20G. As a consequence, the positioning device 4 reverts back to its storage mode.

Figure 20H:
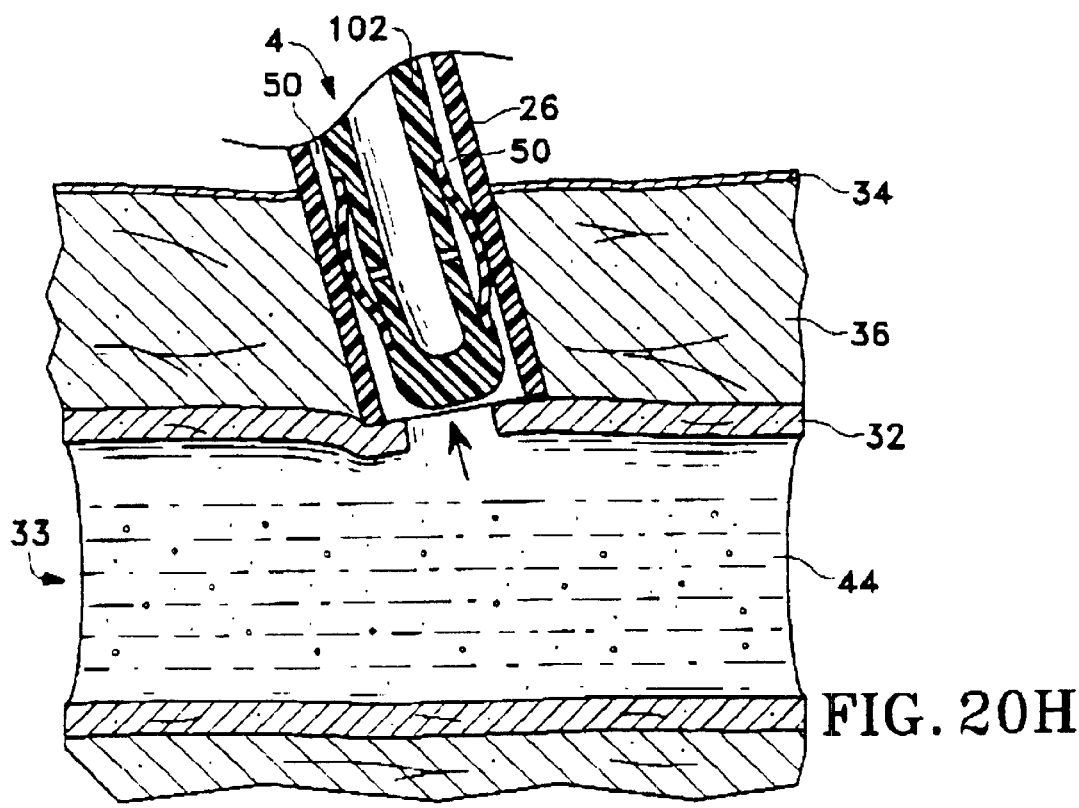

What follows is the step of withdrawing the position device 4. First, the introducer sheath 26 is held stationary, the positioning device 4 at its storage mode is then withdrawn from the introducer sheath 26. FIG. 20H shows the positioning device 4 as in the process of withdrawing.

Figure 20I:
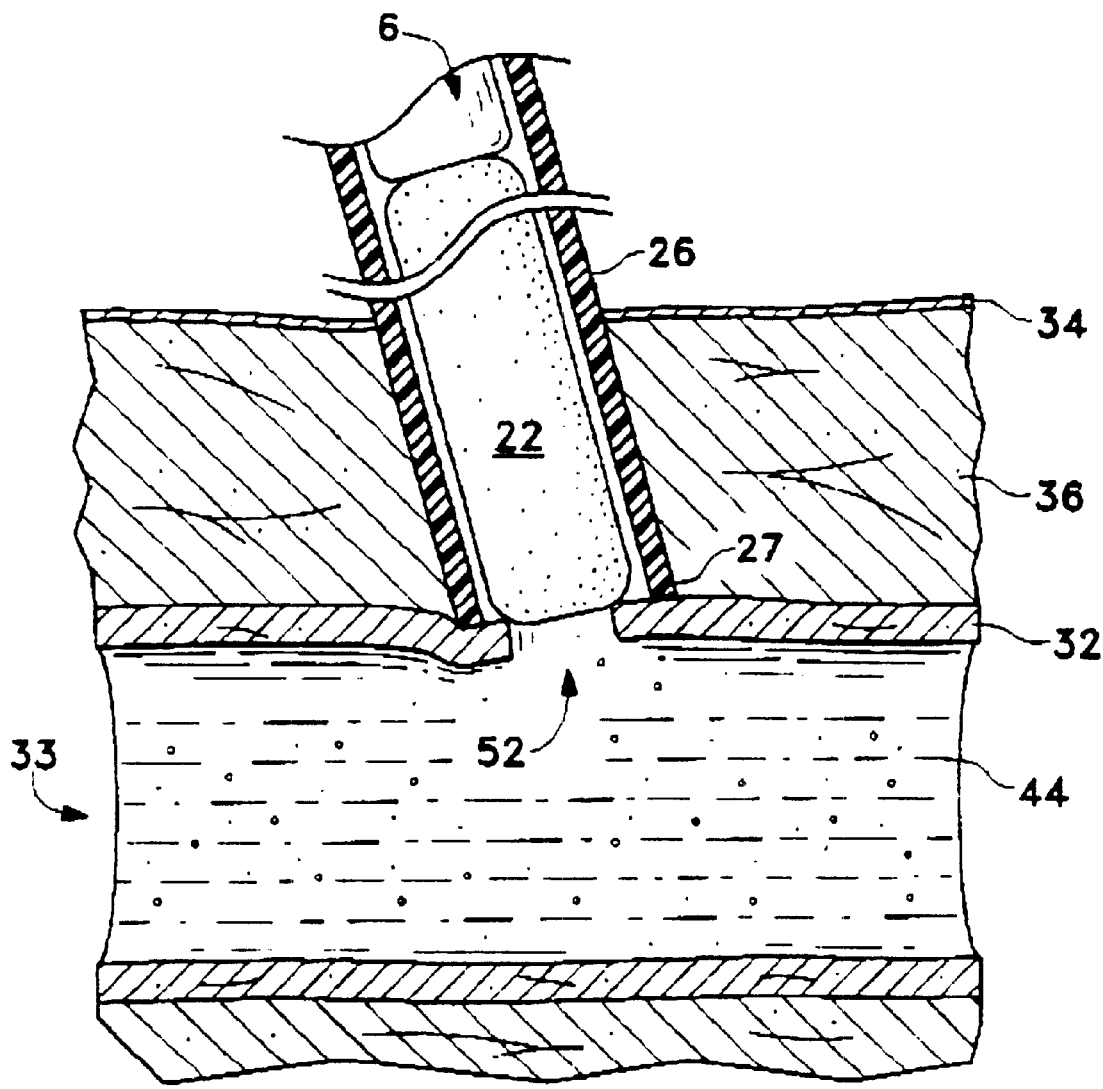

Thereafter, an implant 22 is delivered via the implant delivery device 6 in a manner substantially similar to the previous embodiments and as shown in FIG. 20I. For the sake of conciseness, the implant delivery step is not further repeated in here.

Figure 21:
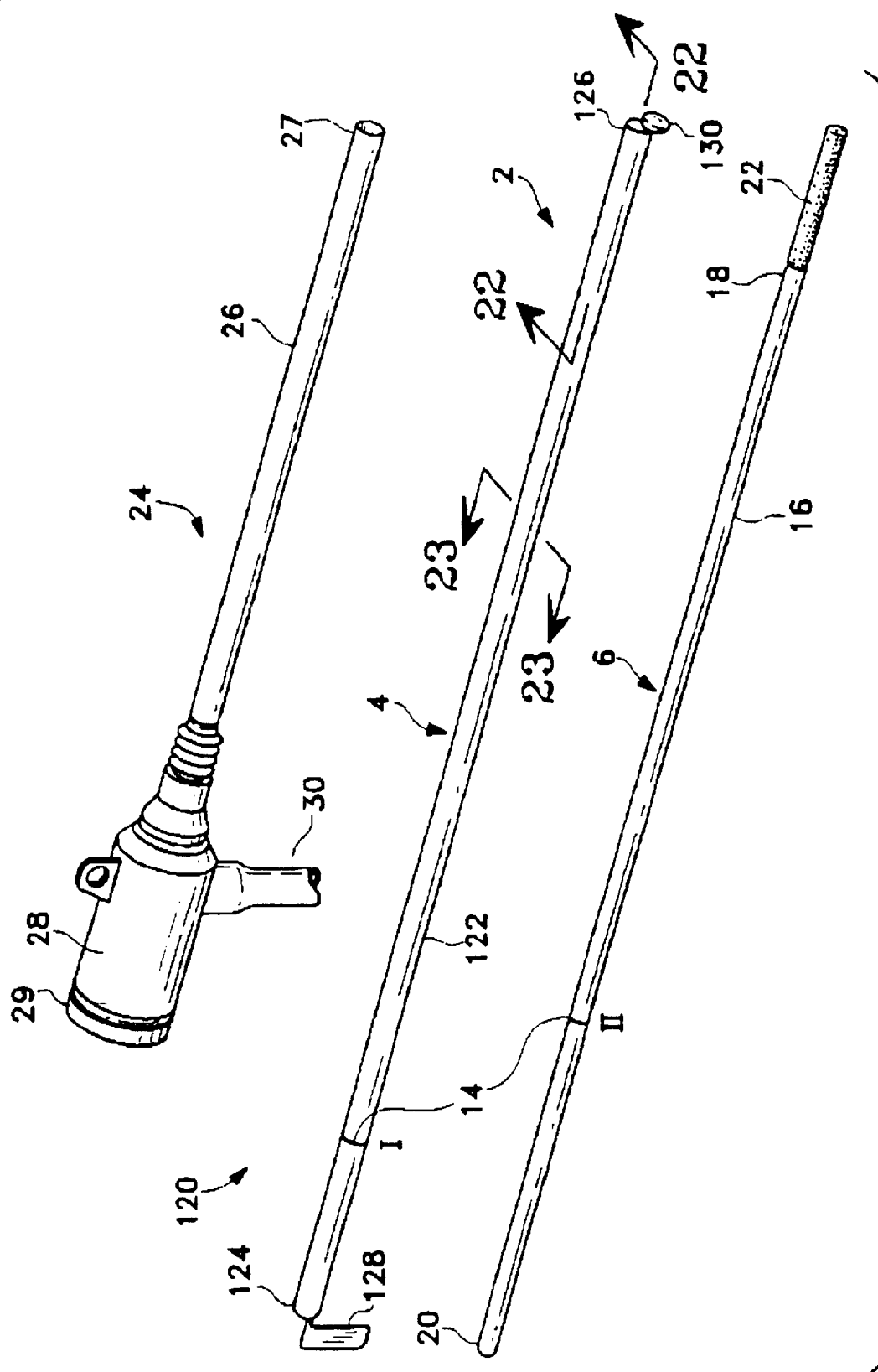
FIG. 21 is a perspective view of a fifth embodiment of the invention showing the various components.
Figure 22:
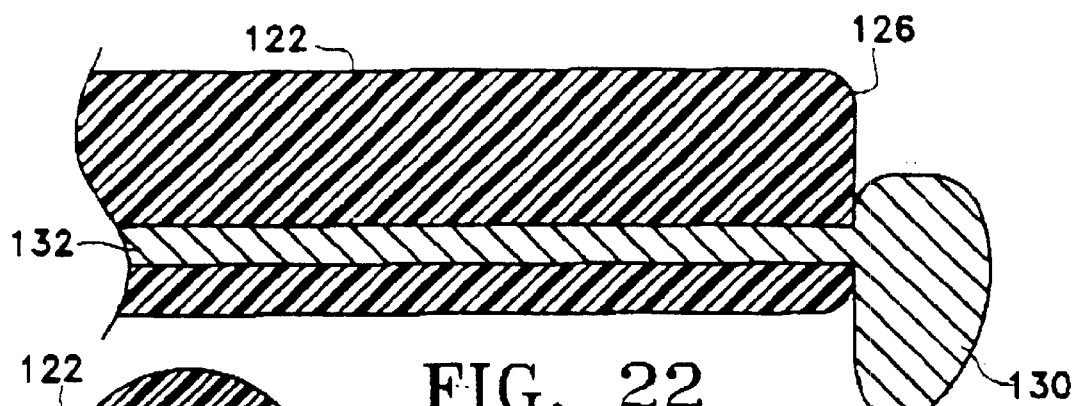
FIG. 22 is a cross-sectional view taken along the line 22—22 of FIG. 21.
Figure 23:
FIG. 23 is a cross-sectional view taken along the line 23—23 of FIG. 21.
Figures 25A, 25B:
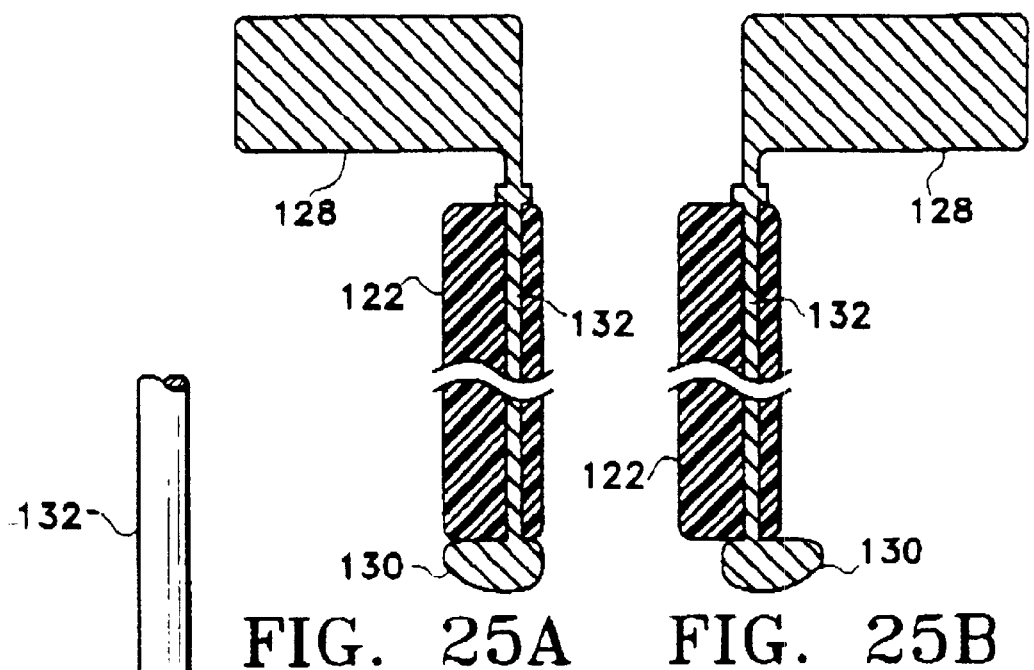
FIGS. 25A and 25B are cross-sectional view of the stopper member of the fifth embodiment at its respective storage and extended positions.
Figure 24:
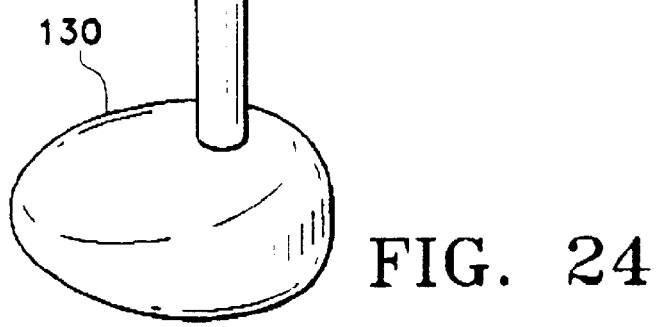
FIG. 24 is a perspective view of an eccentrically attached stopper member used in accordance with the fifth embodiment of the invention.

FIG. 21 shows a fifth embodiment of the invention generally signified by the reference numeral 120. The positioning device 4 in this embodiment comprises a housing member 122 having a proximal end 124 and a distal end 126. Disposed at the proximal end 124 and distal end 126 are respectively a steering flag 128 and a stopper member 130. The steering flag 128 and the stopper member 130 are fixedly connected together by a shaft 132 as partially shown in FIG. 22, which is a cross-sectional view taken along the line 22—22 of FIG. 21. FIG. 23 is another cross-sectional view taken along the line 23—23 of FIG. 21 showing the shaft 132 as positioned off-center with respect to the housing member 122. FIGS. 21–23 additionally and clearly show the shaft 132 as eccentrically disposed and rotatable within the housing member 122. In this specification and in the appended claims, the word "eccentrically" need not be confined to be used with objects that are cylindrical, spherical or circular. Thus, in this case, the housing member 122 can well assume other shapes such as triangular, hexagonal, or even irregular geometrical configurations. FIG. 24 is a perspective view having the housing member 122 removed showing the eccentric connection between the shaft 132 and the stopper member 130. The edges and corners of the housing member 122 at the distal end 126 and the stopper member 130 are preferably rounded off so as to minimize injury to a patient during normal operation. As arranged, the stopper member 130 assumes two modes of operation, namely, the storage mode when the flag 128 is turned to one direction as shown in FIG. 25A, and the extended mode when the flag 128 is turned to another direction as shown in FIG. 25B, respectively. The combination which includes the stopper member 130 connected to the shaft 132 housed in the housing member 122 forms part of a depth sensing mechanism as hereinafter explained.

Figure 26A:
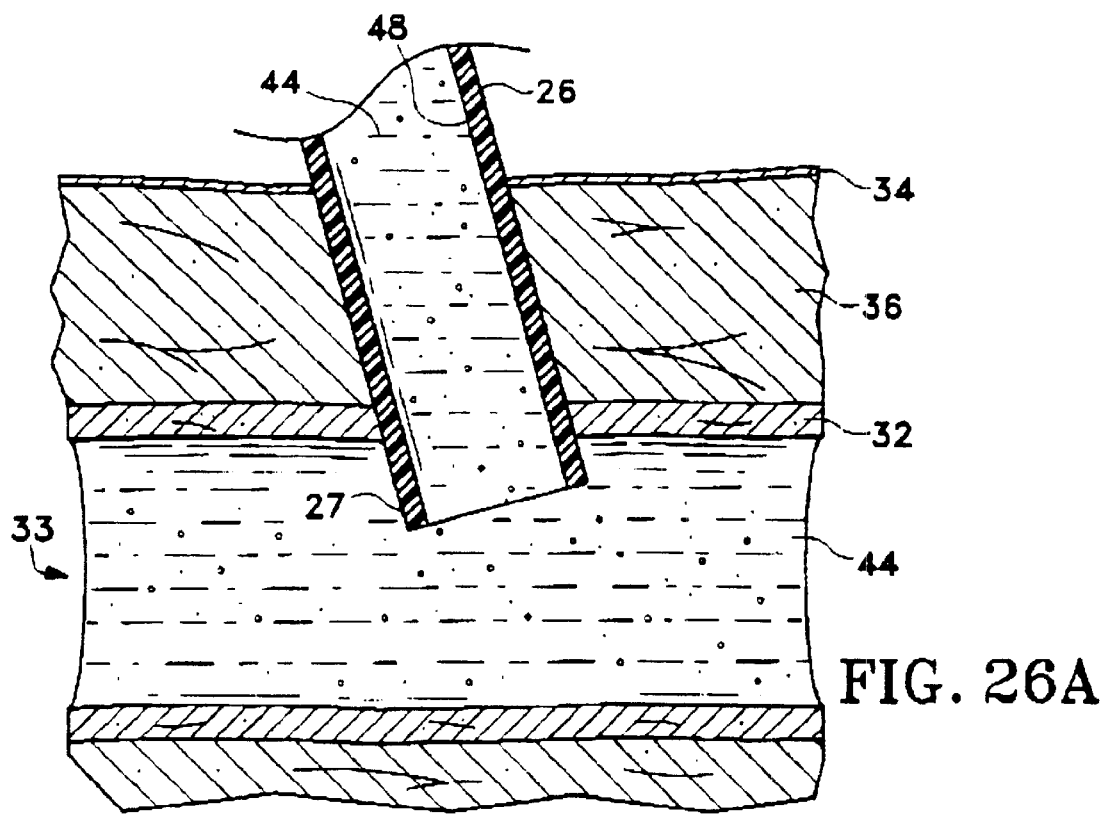
FIGS. 26A–26H are sequential views, shown in cross-section, the method of using the fifth embodiment of the invention.

FIGS. 26A–26H in conjunction with FIGS. 21–24, 25A and 25B illustrate the process of using the puncture wound sealing apparatus of this embodiment. As shown in FIG. 26A, the introducer sheath 26 remains inserted in the patient's artery 33 through the surface skin 34, the subcutaneous tissue 36 and the artery wall 32 after a PCTA procedure, for example. The puncture sealing process of the invention commences with the continued use and without removing the sheath 26 from the patient, thereby substantially eliminating intermediate steps and curtailing unnecessary bleeding.

Figure 26B:
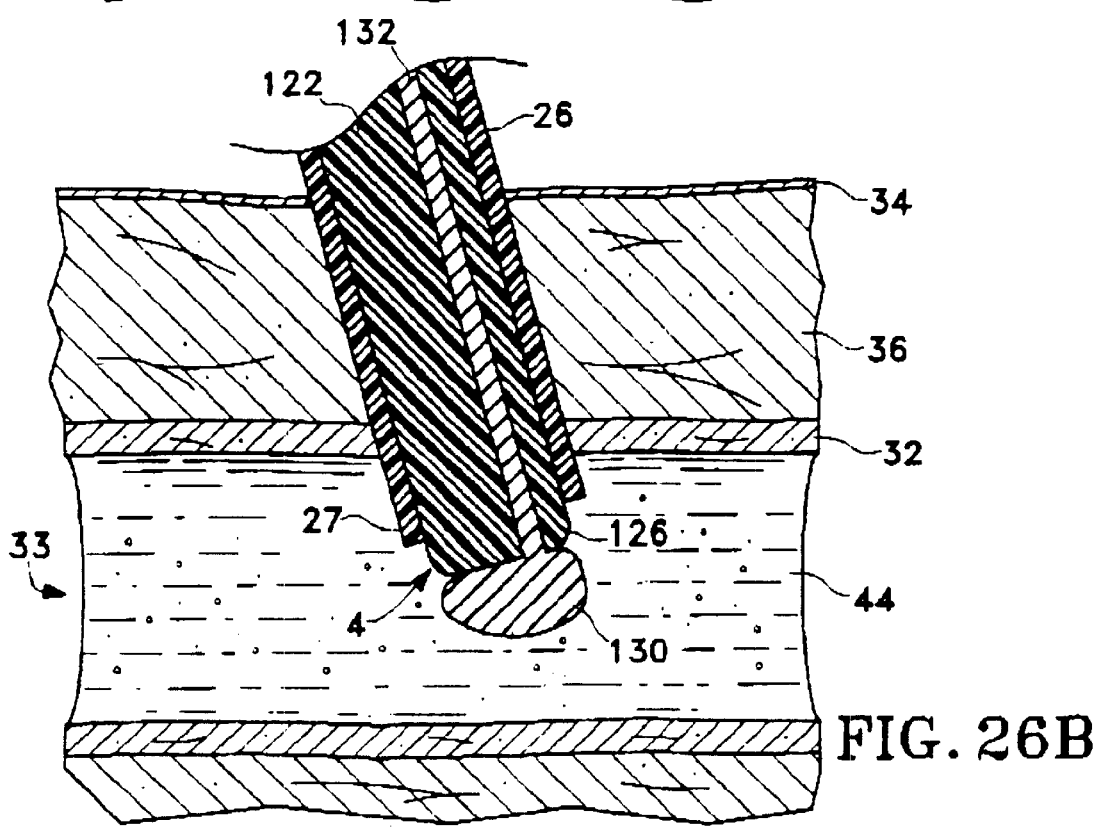

The stopper member 130 is then configured to the storage mode by rotating the steering flag 128 to a storage position as shown in FIG. 25A. The positioning device 4, the housing member 122 carrying the stopper member 130 in this case, is then inserted into the introducer sheath 26, as shown in FIG. 26B. The positioning device 4 can be inserted to a short distance extended beyond the distal end 27 of the introducer sheath 26 as shown in FIG. 26B. The initial depth of insertion of the positioning device 4 with respect to the sheath 6 can be approximately estimated by reading the pre-recorded marking 14 (FIG. 21) adjacent to the proximal end 124 of the housing member 122 with respect to the distal end 29 (FIG. 3) of the introducer 24 in a substantially similar manner as described previously.

Figure 26C:
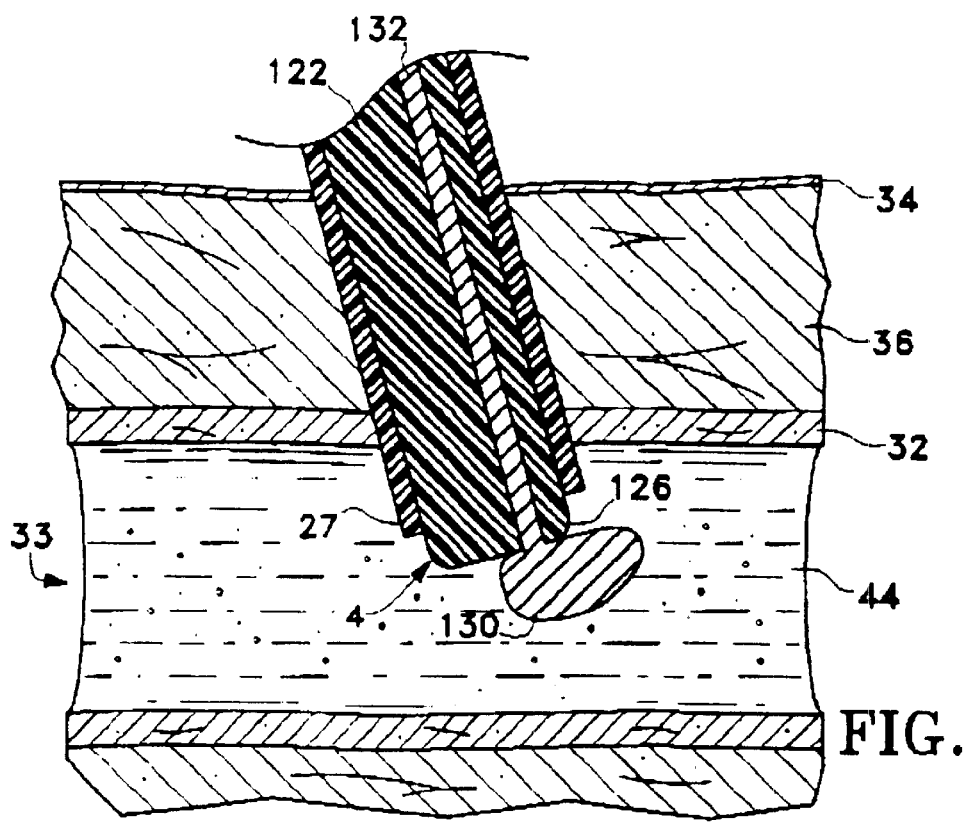

Then, the stopper member 130 is deployed to its extended mode position by rotating the steering flag 128 to the extended direction (FIG. 25B). The resultant structure operated inside the patient (not shown) up to this step is as shown in FIG. 26C.

Figure 26D:
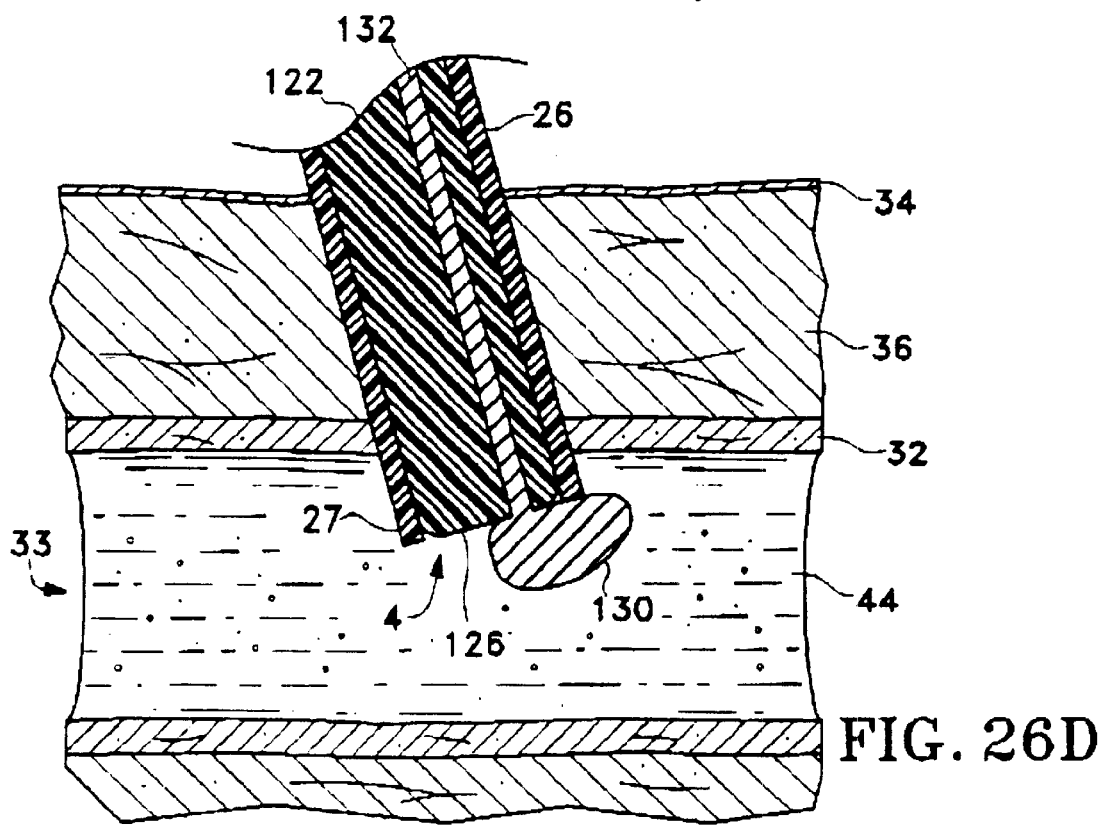

With the sheath member 26 held reasonably stationary, the housing member 122 carrying the stopper member 130 at its extended mode is gradually retracted. During the retracting process, the operator (not shown) at the distal end 124 (FIG. 21) of the elongated member should feel a slight resistance when the stopper member 130 is resisted from further advance by the distal end 27 of the introducer sheath 26 as shown in FIG. 26D.

Figure 26E:
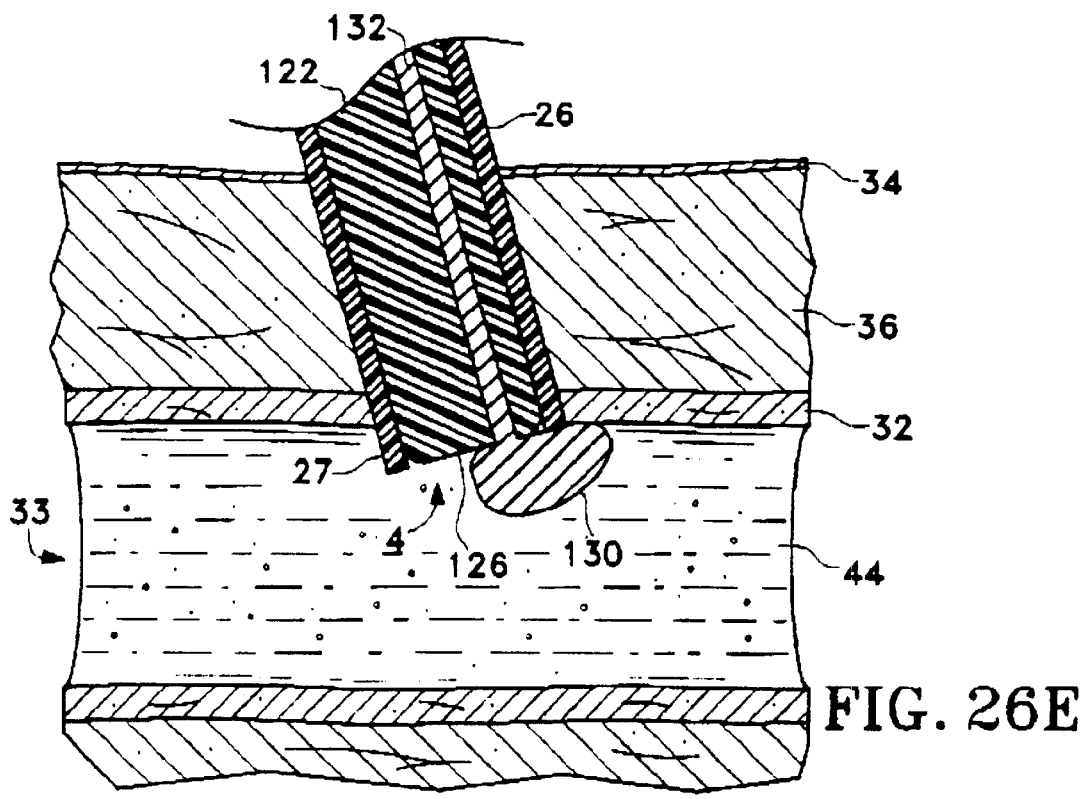

The positioning device 4 along with the introducer sheath 26 are then slowly and simultaneously withdrawn away from the artery 33. Again, during the retracting process, the operator (not shown) should feel another mild resistance when the stopper member 130 is in contact with the artery wall 32 as shown in FIG. 26E. The resistance forces experienced by the operator (not shown) at various stages constitute feedback to the operator (not shown) in fathoming the depth of the introducer sheath 26 with respect to the artery 33.

Figure 26F:
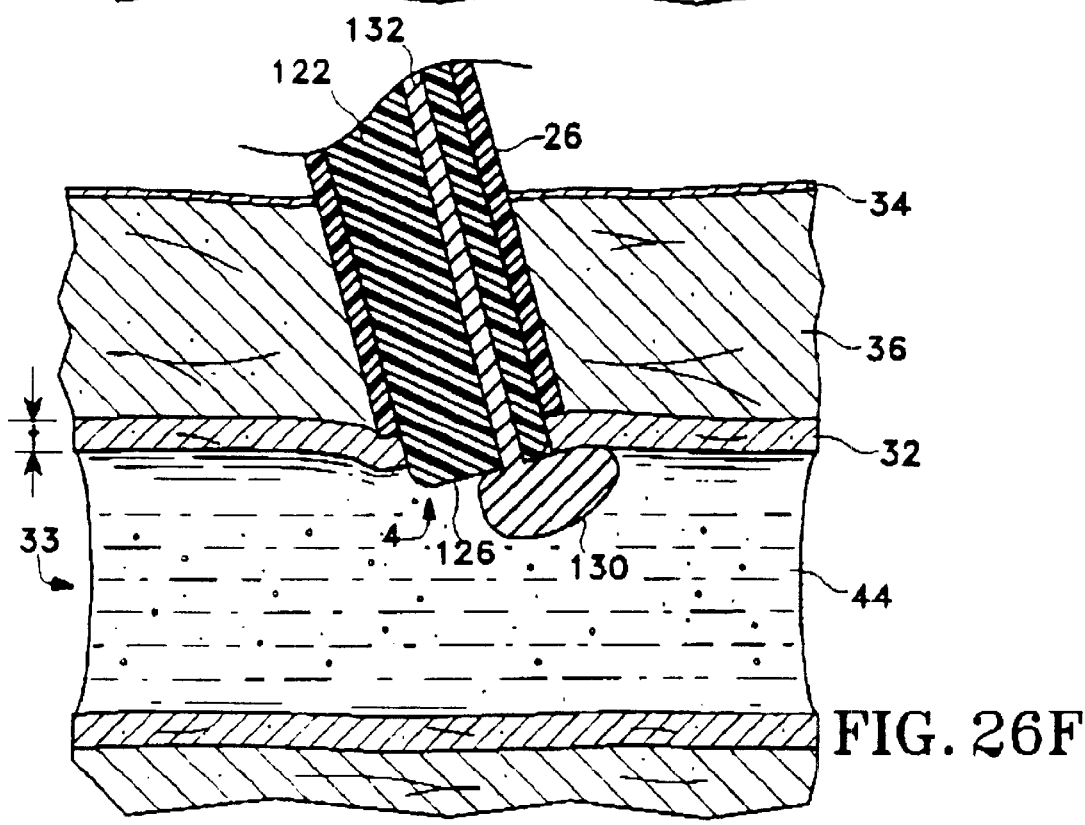

With the stopper member 130 remains at its extended mode position and with the positioning device 4 kept stationary, the introducer sheath 26 is withdrawn further by a short distance t relative to the positioning device 4 as shown in FIG. 26F. In this case, t is the thickness of the artery wall 32 and is approximately 2 mm. Also shown in FIG. 26F is the opening of the artery wall 32 at the wound site 52 gripping onto the positioning device 4.

Figure 26G:
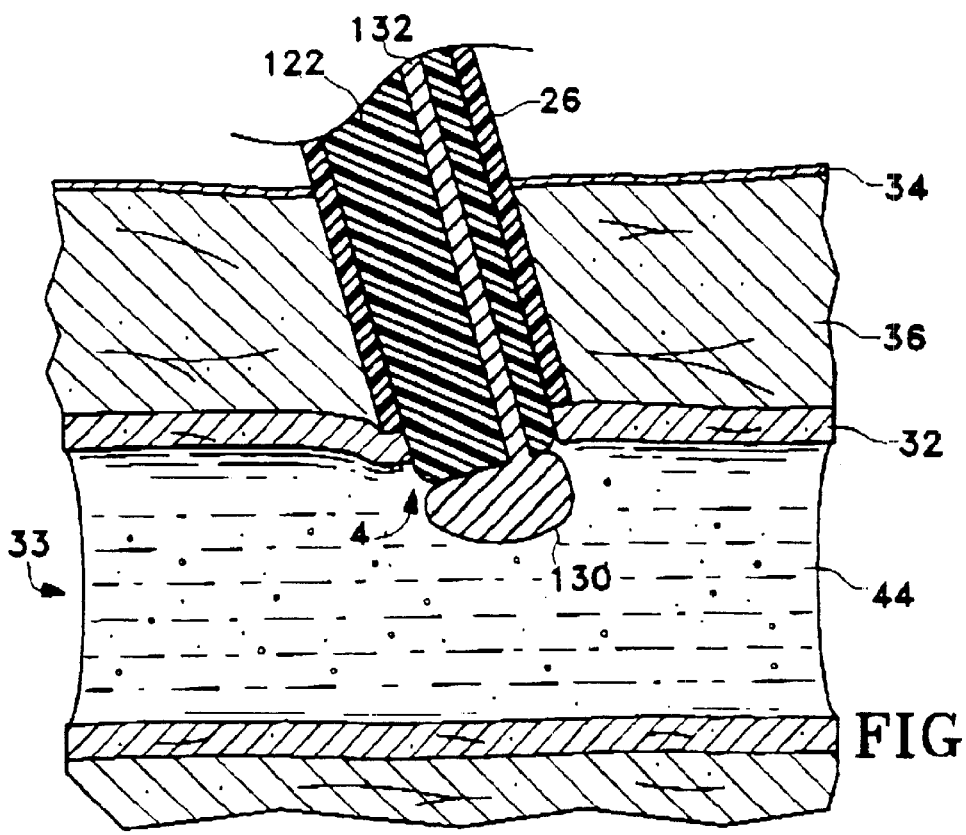

The next step is the withdrawal of the positioning device 4. The steering flag 128 is first rotated to the storage position resulting in the stopper member 130 reverted back to its storage mode as shown in FIG. 26G.

Figure 26H:
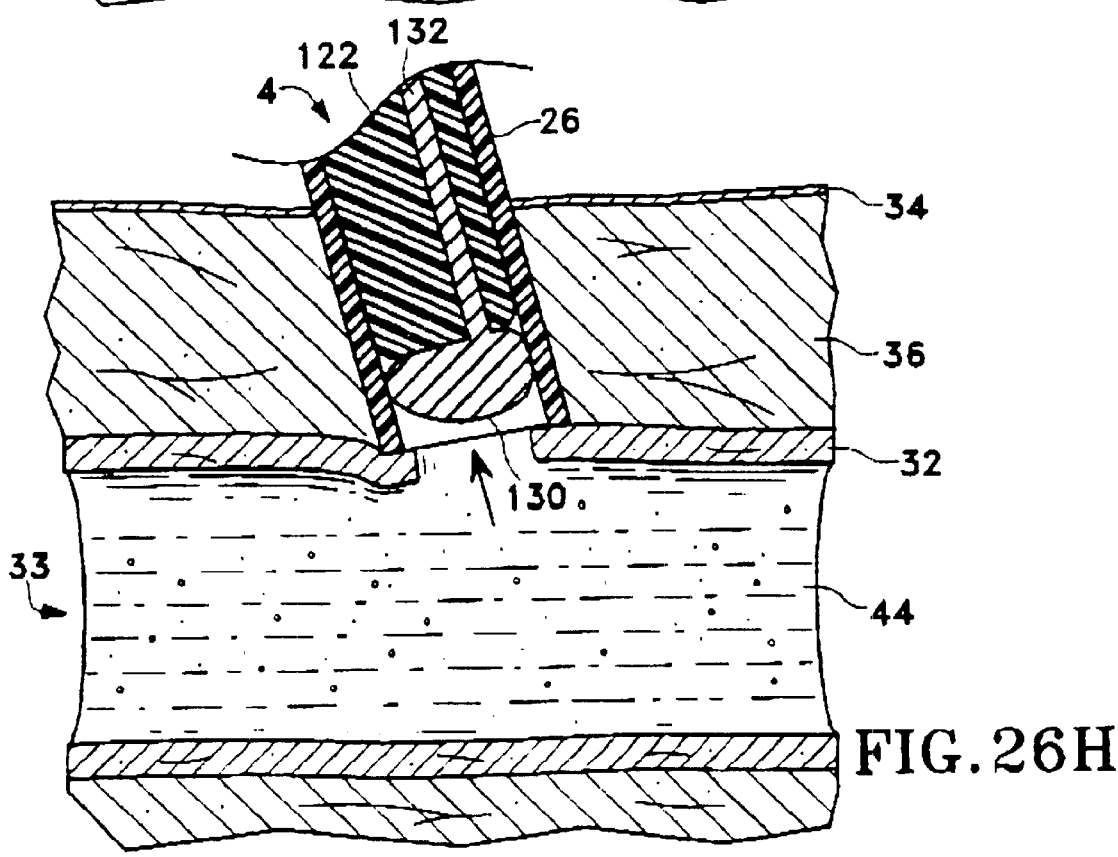

The introducer sheath 26 is held stationary, the housing member 122 carrying the stopper member 130 at its storage mode is withdrawn from the introducer sheath 26 completely. FIG. 26H shows the positioning device 4 as in the process of withdrawing.

The implant delivery step is substantially the same as the previous embodiments and is thus not further elaborated.

Finally, for all the embodiments as described, other changes are possible within the scope of the invention. For example, most of the components, such as the position guides 8, 92 and 102; the delivery rod 16 and the plunger 78; the tubular member 102; and the housing member 122 are depicted as cylindrical and elongated in shape. These components can well assume other geometrical configurations. In addition, in the first and third embodiments, the position guides 8 and 92 and the delivery rod 16 are described as solid rods, these components may very well be hollow. The balloon 110 need not be attached to the tubular member 102 in the manner as described. Other configurations are certainly possible. Furthermore, the stopper member 130 can include a shelf-expanding mechanism after the extended mode for the purpose of providing a larger stopper member 130 to serve the stopping function.

Numerous modifications may be made to the foregoing invention without departing from the basic teachings thereof. Although the present invention has been described in substantial detail with reference to one or more specific embodiments, those of skill in the art will recognize that changes may be made to the embodiments specifically disclosed in this application, yet these modifications and improvements are within the scope and spirit of the invention as set forth in the claims which follow. All publications, patents, and patent applications cited in this specification are incorporated herein by reference as if each such publication, patent, or patent application was specifically and individually indicated to be incorporated herein by reference.

EXAMPLES

Example 1

Implant Expansion

In this experiment, the expansion characteristics of three different implants were studied. The implants are prepared from 100% by weight PEG (polyethylene glycol) (A), 75% by weight PEG and 25% by weight gelatin (B), or 50% by weight PEG and 50% by weight gelatin (C) as follows:

A. 0.18 g of thiol-PEG (pentaerythritol poly(ethylene glycol) ether tetra-thiol, mol. wt. 10,000) is dissolved in 1.5 mL of 200 mM $Na_2CO_3$ adjusted with 200 mM $NaH_2PO_4$ to a pH of 8.3. To this mixture, 0.18 g of succinimidyl-PEG (pentaerythritol poly(ethylene glycol) ether tetra-succinimidyl glutarate, mol. wt. 10,000 is added and mixed. The mixture is injected into a 4.78 mm ID (inside diameter) mold and allowed to crosslink for 15 minutes. The mold is opened up and the wet implant matrix is allowed to dry at room temperature. The dried implant has a diameter of approximately 2.3 mm. As such, the implant shrank in size to 48% of the original diameter.

B. 0.471 g of thiol-PEG is added to a solution containing 4.81 g gelatin (prepared from denatured bovine fibrillar collagen at 65 mg/ml, denatured at 80° C. for 30 min., mol. wt. approximately 100,000) at a concentration of 65 mg/ml and placed in one syringe. 0.471 g of succinimidyl-PEG is dissolved in 3.75 mL of buffer ($Na_2HPO_4$ adjusted with $NaH_2PO_4$ to a pH of 6) and placed in another syringe. These two preparations are mixed together, and the mixture is injected into a 6.35 mm ID (inside diameter) mold and allowed to crosslink for 15 minutes. The mold is opened up and the wet implant matrix is allowed to dry at room temperature. The dried implant has a diameter of approximately 2.5 mm. As such, the implant shrank in size to 39% of the starting diameter.

C. 0.28 g of thiol-PEG is added to a solution containing 8.31 g gelatin at a concentration of 65 mg/ml and placed in one syringe. 0.28 g of succinimidyl-PEG is dissolved in 3.75 mL of buffer ($Na_2HPO_4$ adjusted with $NaH_2PO_4$ to a pH of 6) and placed in another syringe. These two preparations are mixed together, and the mixture is injected into a 7.7 mm ID (inside diameter) mold and allowed to crosslink for 30 minutes. The mold is opened up and the wet implant matrix is allowed to dry at room temperature. The dried implant has a diameter of approximately 2.6 mm. As such, the implant shrank in size to 34% of the starting diameter.

The implants are placed in a testing device with silicone tubing to simulate the tissue channel in which the implant is administered in vivo. There is a 1 mm gap between the plug and the tubing wall immediately after being placed in the device. After exposure to cow blood at 150 mm Hg, the time it takes for the implant to swell to seal the tubing is measured. The measured expansion times were as follows: Implant A=21–22 minutes, Implant B=11–12 minutes, and Implant C=11–12 minutes.

Example 2

Implant Burst Strength

The implants prepared in Example 1 are also tested as described therein for their ability to maintain their position in the tubing upon exposure to an increasing pressure. The "burst strengths" as measured by the amount of pressure which resulted in displacement of the plug were as follows: Implant A=400 mm Hg, Implant B=730 mm Hg, and Implant C=675 mm Hg.

Example 3

Elongation Characteristics

The implants prepared in Example 1 are also tested to evaluate the amount of elongation after exposure to cow blood. Too much elongation is undesirable, because it may result in partial or total occlusion of the vessel outside of which the implant is administered. After 6 days in cow blood, the % length gain of the implants was measured as follows: Implant A=>600%, Implant B=380%, and Implant C=320%. Unexpectedly, even though Implant A comprising PEG expanded slower initially as reported in Example 1, it elongated more after prolonged exposure to cow blood. This experiment confirms the desirability of implants made of not more than 75% PEG, and suggests that at least 25% gelatin may also be desirable.

Example 4

In Vivo Studies

This experiment tests the ability of an implant delivered into a femoral artery puncture hole to seal the puncture site following a catheterization procedure. Two dogs are used in this experiment and three catheterization access sites are created.

A dog femoral artery puncture hole model is used for this experiment. An introducer position guide, 7 Fr., is used to indicate the position of the tip of the introducer (8 Fr.). The guide is ~10 cm longer than the introducer for the procedure. An implant <8 Fr. (2.3–2.6 mm in OD), and 6.5–7.5 cm long is used The implant is prepared as follows: 180 mg thiol-PEG, dry powder is dissolved in 1.5 mL of 200 mM $Na_2CO_3$/200 mM $NaH_2PO_4$ pH 8.3 buffer and placed in a 3 mL syringe. 180 mg succinimidyl-PEG dry powder is loaded in another 3 mL. syringe. These two syringes are connected together and their contents are passed 20 times back and forth to dissolve the material with buffer and ant to mix thoroughly. The mixture is injected into a mold made of silicone tubing, 12 cm in length, 4.76 mm in ID, and 7.94 mm in OD. After five minutes polymerization time, the silicone tubing is peeled open. The wet implant matrix is removed from the tubing and dried at room temperature for 24 hr. To ensure the proper OD of the dried plug, pins ar used to pin down both ends of the wet gel. Pins are also used to support the side of the gel during drying. The dried implant is attached to a long plastic delivery rod by an adhesive.

At the end of the catheter procedure, the introducer (8 Fr.) is left in place inserted in the artery. The introducer position guide, 7 Fr., is inserted through the septum of the introducer to the mark on the guide to indicate that the tip of the position guide is ~2.5 cm outside of the tip of the introducer. The introducer is retrieved slowly out of the artery and stopped at just outside of the arterial wall indicated by ceasing of blood flow from the side arm of the introducer. The introducer position guide is retrieved with the introducer and did not change the marking position with the introducer.

A thumb pressure is applied on the artery at about 1 cm away from the arterial hole (not the needle hole on the skin) on the proximal end to stop the flow of blood in the artery. The introducer is secured on the skin. The guide is retrieved out of the introducer while holding the introducer steady. The expandable implant is inserted through the septum of the introducer to the mark on the delivery rod to indicate that the tip of the plug is at the tip of the introducer while holding the introducer steady. The introducer is pulled out of the skin while holding the delivery rod steady and keeping the tip of plug on top of the arterial hole. The portion of the plug outside of the skin is cut off. A thumb pressure was applied on the plug for 3 min. for allowing the plug to hydrate and swell.

The results indicated that the puncture site was sealed, and no hematoma was observed.

What is claimed is:

1. An apparatus for sealing a tissue puncture opening outside a blood vessel of a living being after a medical procedure in which a sheath member is inserted into said puncture opening, said apparatus comprising:

a positioning device adapted to be inserted into said sheath member, said positioning device having a depth sensing mechanism, said sheath member being cooperatively movable and capable of being positioned about said positioning device in response to feedback provided by said depth sensing mechanism so as to allow for accurate positioning of the sheath member and for accurate delivery of an implant into the tissue puncture opening; and an implant delivery device adapted to be inserted in said sheath member to deliver the implant into said tissue puncture opening outside said blood vessel.

2. The apparatus as set forth in claim 1 wherein during normal operation said sheath member is positioned proximally outside said blood vessel as a reference position for the delivery of said implant by said implant delivery device.

3. The apparatus as set forth in claim 1 wherein said sheath member includes a bore having a cross-sectional dimension, and said positioning device has a cross-sectional dimension smaller than the corresponding cross-sectional dimension of said bore of said sheath member, such that when said positioning device is inserted into said sheath member, a volume of gap space is formed therebetween allowing fluid communication therethrough, said depth sensing mechanism including means for monitoring fluid communication in said gap space.

4. The apparatus as set forth in claim 3 wherein said positioning device comprises a first elongated member and said implant delivery device comprises a second elongated member.

5. The apparatus as set forth in claim 4 wherein said positioning device includes a distal end having a cross-sectional dimension substantially the same as the corresponding cross-sectional dimension of said bore of said sheath member, such that when said distal end of said positioning device is inserted into said bore, said distal end sealingly fits into said bore.

6. The apparatus as set forth in claim 3 wherein said positioning device comprises a first tubular member, and said implant delivery device comprises a second tubular member and an elongated member which is slidable in said second tubular member.

7. The apparatus as set forth in claim 6 wherein said second tubular member includes a distal end having a slit formed therein to facilitate reception of an implant.

8. The apparatus as set forth in claim 1 wherein said positioning device includes a tubular member attached to a balloon, said tubular member being in fluid communication with said balloon.

9. The apparatus as set forth in claim 8 wherein said balloon is characterized by a deflated mode and an inflated mode, the cross-sectional dimension of said balloon during said inflated mode being larger than the corresponding cross-sectional dimension of said puncture opening, such that when said balloon is in said blood vessel during said inflated mode said balloon is prevented from passing through said puncture opening, said depth sensing mechanism including means for monitoring the location of said balloon along said sheath member.

10. The apparatus as set forth in claim 1 wherein said positioning device includes a housing member, a wire member having a distal end attached with a stopper member, said wire member being eccentrically disposed within said housing member.

11. The apparatus as set forth in claim 10 wherein said stopper member being characterized by a storage mode and an extended mode, said stopper member being in said storage mode when said wire member within said elongated member is rotated to a first position, and said stopper member being in said extended mode when said wire within said elongated member is rotated to a second position, the cross-sectional dimension of the distal end of said positioning device having said stopper member in said extended mode being larger than the corresponding cross-sectional dimension of said puncture opening, such that when said stopper member is in said vessel during said extended mode, said stopper member is prevented from passing through said puncture opening, said depth sensing mechanism including means for monitoring the location of said stopper member along said sheath member.

12. The apparatus as set forth in claim 1 further comprising an implant, wherein said implant comprises a dried polymer matrix.

13. The apparatus as set forth in claim 12, wherein said polymer matrix further comprises a natural or synthetic polymer.

14. The apparatus as set forth in claim 1 further comprising an implant, wherein the implant comprises a dried matrix of a mixture of a synthetic hydrophilic polymer and a protein selected from the group consisting of collagen and gelatin.

15. The apparatus as set forth in claim 14 wherein the synthetic hydrophilic polymer is polyethylene glycol.

16. The apparatus as set forth in claim 15 wherein the protein is gelatin.

17. The apparatus as set forth in claim 15 wherein the implant is formed by crosslinking the polyethylene glycol to the gelatin prior to drying.

18. The apparatus as set forth in claim 12 wherein the matrix further comprises an imaging agent.

19. The apparatus as set forth in claim 12 wherein the polymer is polyethylene glycol.

20. An apparatus for sealing a tissue puncture opening outside a blood vessel of a living being after a medical procedure in which a sheath member having a bore with a cross-sectional dimension is inserted into said puncture opening, said apparatus comprising:
a positioning device slidable in said sheath member, said positioning device having a cross-sectional dimension smaller than the cross-sectional dimension of said bore of said sheath member, such that when said positioning device is slid into said sheath member, a volume of gap space is formed therebetween allowing fluid communication therethrough so as to allow for accurate positioning of the sheath member and for accurate delivery of an implant into the tissue puncture opening.

21. The apparatus as set forth in claim 20 further including an implant delivery device adapted to be inserted into said sheath member to deliver an implant into said tissue puncture opening outside said blood vessel.

22. The apparatus as set forth in claim 21 wherein said positioning device comprises a first elongated member and said implant delivery device comprises a second elongated member.

23. The apparatus as forth in claim 22 wherein said first elongated member includes a distal end having a cross-sectional dimension substantially the same as the cross-sectional dimension of said bore of said sheath member, such that when said distal end of said first elongated member is inserted into said bore said distal end sealingly fits into said bore.

24. The apparatus as set forth in claim 21 wherein said positioning device comprises a first tubular member, and said implant delivery device comprises a second tubular member and an elongated member which is slidable in said second tubular member.

25. The apparatus as set forth in claim 24 wherein said second tubular member includes a distal end having a slit formed therein to facilitate reception of an implant.

26. The apparatus as set forth in claim 20 wherein the relative position of said sheath member with respect to said blood vessel during use is adjusted by monitoring the fluid communication in said gap space.

27. The apparatus as set forth in claim 20 further comprising a fluid monitoring section in fluid communication with said gap space.

28. The apparatus as set forth in claim 21 further comprising an implant, wherein the implant comprises a dried polymer matrix.

29. The apparatus as set forth in claim 28 wherein the implant further comprises a mixture of polyethylene glycol and gelatin.

30. An apparatus for sealing a tissue puncture opening outside a blood vessel of a living being after a medical procedure in which a sheath member is inserted into said puncture opening, said apparatus comprising:

a positioning device adapted to be inserted via its distal end in said sheath member, said positioning device being characterized by a storage mode and an extended mode, such that when said positioning device is at said storage mode, said positioning device is slidable along said sheath member, and such that when said positioning device is at said extended mode, the cross-sectional dimension of the distal end of said positioning device exceeds the corresponding cross-sectional dimension of said puncture opening and is stopped by said puncture opening; and an implant delivery device adapted to be inserted in said sheath member to deliver an implant into said tissue puncture opening outside said blood vessel, wherein the positioning device allows for accurate positioning of the sheath member and for accurate delivery of the implant into the tissue puncture opening.

31. The apparatus as set forth in claim 30 wherein said positioning device includes a tubular member attached to a balloon, said tubular member being in fluid communication with said balloon.

32. The apparatus as set forth in claim 31 wherein said storage mode corresponds to said balloon being deflated and said extended mode corresponds to said balloon being inflated.

33. The apparatus as set forth in claim 30 wherein said positioning device includes a housing member, a wire member having a distal end attached with a stopper member, said wire member being eccentrically disposed within said elongated member.

34. The apparatus as set forth in claim 33 wherein said storage mode corresponds to said wire member within said elongated member being rotated in one direction, and said extended mode corresponds to said wire member within said elongated member being rotated in another direction, the cross-sectional dimension of the distal end of said positioning device having said stopper member during said extended mode being larger than the corresponding cross-sectional dimension of said puncture opening, such that when said stopper member is in said vessel during said extended mode, said stopper member is stopped by said puncture opening.

35. The apparatus as set forth in claim 30 further comprising an implant, wherein the implant comprises a dried polymer matrix.

36. The apparatus as set forth in claim 30, wherein the matrix further comprises a natural or synthetic polymer.

37. The apparatus as set forth in claim 30 further comprising an implant, wherein the implant comprises a dried matrix of a mixture of a synthetic hydrophilic polymer and a protein selected from the group consisting of collagen and gelatin.

38. The apparatus as set forth in claim 37 wherein the synthetic hydrophilic polymer is polyethylene glycol.

39. The apparatus as set forth in claim 38, wherein the protein is gelatin.

40. A method of sealing a tissue puncture opening outside a blood vessel of a living being after a medical procedure in which a sheath member having a bore is inserted into and remains inside said puncture opening, said sheath member being in fluid communication with said blood vessel, said method comprising the steps of:

(a) providing a positioning device having a depth sensing mechanism;

(b) inserting said positioning device in said sheath member;

(c) actuating said depth sensing mechanism for providing feedback;

(d) positioning said sheath member along said positioning device in response to said feedback so as to allow for accurate delivery of an implant into the tissue puncture opening;

(e) withdrawing said positioning device from said sheath member; and (f) delivering an implant through said sheath member into said tissue puncture opening outside said blood vessel.

41. The method as set forth in claim 40 wherein step (d) includes positioning said sheath member outside of said blood vessel and proximally adjacent to said blood vessel.

42. The method as set forth in claim 40 wherein step (a) includes providing said positioning device having a cross-sectional dimension smaller than the corresponding cross-sectional dimension of said bore of said sheath member, such that when said positioning device is inserted in said sheath member, a volume of gap space is formed therebetween allowing fluid communication therethrough, and wherein step (c) includes monitoring fluid communication in said gap space.

43. The method as set forth in claim 42 wherein step (a) further includes providing a first elongated member and step (f) includes the substeps of:

(i) providing a second elongated member having a proximal end and a distal end;

(ii) attaching said implant to said distal end of said second elongated member; and (iii) delivering said implant by inserting said second elongated member with said implant attached through said sheath member.

44. The method as set forth in claim 43 wherein step (a) further includes providing said first elongated member with an enlarged distal end having a cross-sectional dimension substantially the same as the corresponding cross-sectional dimension of said bore.

45. The method as set forth in claim 42 wherein step (a) includes providing a first tubular member and step (f) includes the substeps of:

providing a second tubular member;

(ii) providing an elongated member having a proximal end and a distal end;

(iii) inserting said elongated member and said implant in said second tubular member with said distal end abutting said implant;

(iv) inserting said second tubular member in said first tubular member before step (b); and (v) withdrawing said elongated member and said second tubular member after step (e).

46. The method as set forth in claim 40 wherein step (a) includes providing said positioning device having a tubular member attached to a balloon, said tubular member being in fluid communication with said balloon.

47. The method as set forth in claim 46 wherein said balloon is further characterized by having a deflated mode and an inflated mode, the cross-sectional dimension of said balloon during said inflated mode being larger than the corresponding dimension of said puncture opening, such that when said balloon is in said blood vessel during said inflated mode said balloon is stopped by said puncture opening, and wherein step (c) includes monitoring the location of said balloon along said sheath member being stopped by said puncture opening.

48. The method as set forth in claim 40 wherein step (a) includes providing said positioning device having a housing member, a wire member having a distal end attached with a stopper member, said wire member being eccentrically disposed within said elongated member.

49. The method as set forth in claim 48 wherein said stopper member is further characterized as having a storage mode and an extended mode, said stopper member being in said storage mode when said wire member within said elongated member is rotated to one direction, and said stopper member being in said extended mode when said wire within said elongated member is rotated to another direction, the cross-sectional dimension of the distal end of said positioning device having said stopper member in said extended mode being larger than the corresponding dimension of said puncture opening, such that when said stopper member is in said vessel during said extended mode, said stopper member is stopped by said puncture opening, and wherein step (c) includes monitoring the location of said stopper member along said sheath member being stopped by said puncture opening.

50. A method of sealing a tissue puncture opening outside a blood vessel of a living being after a medical procedure in which a sheath member having a bore is inserted into and remains inside said puncture opening, said sheath member being in fluid communication with said blood vessel, said method comprising the steps of:
 (a) providing a positioning device having a cross-sectional dimension smaller than the corresponding cross-sectional dimension of said bore of said sheath member, such that when said positioning device is inserted in said sheath member, a volume of gap space is formed therebetween allowing fluid communication therethrough;
 (b) inserting said positioning device in said sheath member;
 (c) gradually withdrawing said sheath member relative to said positioning device by monitoring the fluid flow in said volume of gap space;
 (d) terminating step (c) when the fluid flow in said gap space is substantially reduced so as to allow for accurate delivery of an implant into the tissue puncture opening;
 (e) withdrawing said positioning device from said sheath member; and
 (f) delivering an implant through said sheath member to said puncture opening thereby sealing said opening.

51. The method as set forth in claim 50 wherein step (a) includes providing a first elongated member and step (f) includes the sub-steps of:
 (i) providing a second elongated member having a proximal end and a distal end;
 (ii) attaching said implant to said distal end of said second elongated member; and
 (iii) delivering said implant by inserting said second elongated member with said implant attached through said sheath member.

52. The method as set forth in claim 50 wherein step (a) further includes providing an elongated member with an enlarged distal end having a crosssectional dimension substantially the same as the corresponding cross-sectional dimension of said bore, such that when said distal end is inserted into said bore, said distal end sealingly fits into said bore.

53. The method as set forth in claim 50 wherein step (a) includes providing a first tubular member and step (f) includes the sub-steps of:
 (i) providing a second tubular member;
 (ii) providing an elongated member having a proximal end and a distal end;
 (iii) inserting said elongated member and said implant in said second tubular member with said distal end abutting said implant;
 (iv) inserting said second tubular member in said first tubular member before step (b); and
 (iii) withdrawing said elongated member and said second tubular member after step (e).

54. An implant adapted for sealing a tissue puncture opening outside a blood vessel of a living being, wherein said implant comprises a dried, swellable, resorbable matrix of a synthetic hydrophilic polymer and a protein.

55. A method of sealing a tissue puncture opening in a living being that extends from an external puncture opening in a skin surface percutaneously through said tissue to a depth X, comprising the steps of:
 (a) inserting an elongated implant having a length greater than X into said tissue puncture opening to a depth of X, wherein said implant comprises a dried, swellable, resorbable matrix; and
 (b) removing that portion of the implant that extends outside the external puncture opening.

56. A method for sealing a tissue puncture opening outside a blood vessel of a living being comprising the steps of:
 (a) delivering a swellable, resorbable biocompatible liquid or gel implant through the tissue puncture opening to a position outside the blood vessel through the use of a positioning device adapted for use to accurately deliver the implant into the tissue puncture opening; and
 (b) allowing the implant to seal the opening by forming or continuing to form a matrix after administration.

* * * * *